United States Patent
Sabeti et al.

(10) Patent No.: US 11,600,392 B2
(45) Date of Patent: Mar. 7, 2023

(54) HEALTH DATA AGGREGATION AND OUTBREAK MODELING

(71) Applicants: THE BROAD INSTITUTE, INC., Cambridge, MA (US); PRESIDENT AND FELLOWS OF HARVARD COLLEGE, Cambridge, MA (US)

(72) Inventors: Pardis Sabeti, Cambridge, MA (US); Andres Colubri, Cambridge, MA (US); Todd Brown, Cambridge, MA (US)

(73) Assignees: The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/102,901

(22) Filed: Nov. 24, 2020

(65) Prior Publication Data

US 2021/0151198 A1 May 20, 2021

Related U.S. Application Data

(63) Continuation of application No. 16/936,278, filed on Jul. 22, 2020.

(Continued)

(51) Int. Cl.
*G16H 50/80* (2018.01)
*G16H 50/50* (2018.01)
(Continued)

(52) U.S. Cl.
CPC .......... *G16H 50/80* (2018.01); *G06N 7/005* (2013.01); *G16H 50/50* (2018.01); *G16H 50/70* (2018.01); *H04W 4/023* (2013.01); *H04W 4/80* (2018.02)

(58) Field of Classification Search
CPC .................................................... G16H 60/70
See application file for complete search history.

(56) References Cited

U.S. PATENT DOCUMENTS 9,460,263 B2 * 10/2016 Holmes .................. G16Z 99/00
2014/0133656 A1 * 5/2014 Wurster ................ H04W 4/023
380/270

(Continued)

FOREIGN PATENT DOCUMENTS

CA        2936876 A1     1/2017

OTHER PUBLICATIONS https://silo.zone/synPop.html (Year: 2018).*
Eskild Petersen et al. "Comparing SARS-CoV-2 with SARS-CoV and influenza pandemics." www.thelancet.com/infection. vol. 20, Aug. 2020. Published Jul. 3, 2020. https://doi.org/10.1016/S1473-3099(20)30484-9 (Year: 2020).*

(Continued)

*Primary Examiner* — Robert A Sorey
*Assistant Examiner* — Kristine K Rapillo
(74) *Attorney, Agent, or Firm* — F. Brent Nix, Esq.; Johnson, Marcou, Isaacs & Nix, LLC; Scott Hendrix, Esq.

(57) ABSTRACT

The technology uses aggregated health data and outbreak models to conduct differential diagnosis and provide risk assessments that indicate a likelihood of contracting COVID-19. A healthcare organization server provides COVID-19 diagnostic kits and health applications to participating computing devices that log user health data and registers contacts with other participating users via wireless interactions. The organization compares received data with data received from computing devices from a plurality of other users and identifies common occurrences. The server creates an outbreak model of a geographic region based on the data. The server communicates a determined likelihood (Continued)

of contracting COVID-19 of the user to the user computing device. The server provides the outbreak model to the user, healthcare workers, or others for use in responding to the outbreak.

30 Claims, 20 Drawing Sheets

Specification includes a Sequence Listing.

Related U.S. Application Data

(60) Provisional application No. 62/877,754, filed on Jul. 23, 2019, provisional application No. 62/877,773, filed on Jul. 23, 2019.

(51) Int. Cl.
*G16H 50/70* (2018.01)
*H04W 4/80* (2018.01)
*G06N 7/00* (2023.01)
*H04W 4/02* (2018.01)

(56) References Cited

U.S. PATENT DOCUMENTS

| | | |
|---|---|---|
| 2017/0316324 A1* | 11/2017 | Barrett ............... G06N 20/20 |
| 2017/0352119 A1 | 12/2017 | Pittman et al. |
| 2020/0294680 A1 | 9/2020 | Gupta et al. |
| 2020/0357510 A1 | 11/2020 | Bhavani et al. |
| 2020/0381092 A1 | 12/2020 | Granvold et al. |
| 2021/0005324 A1 | 1/2021 | Bostic et al. |

OTHER PUBLICATIONS

"International Search Report and Written Opinion for PCT/US2020/043140", issued by the European Patent Office (EPO), as international searching authority, dated Oct. 30, 2020.

Hashemian, et al., "FLUNET: Automated Tracking of Contacts During Flu Season", Modeling and Optimization in Mobile, Ad Hoc and Wireless Networks (WIOPT), 2010 Proceedings of the 8th International Symposium on, IEEE, XP31714608, ISBN: 978-1-4244-7523-0, pp. 348-353, May 31, 2010.

Shah, et al., "Containing the Spread of Infectious Disease on College Campuses", medRxiv, pp. 1-33, Dec. 24, 2020.

Wohl, et al., "Combining genomics and epidemiology to track mumps virus transmission in the United States", PLOS Biology, 18(2): e3000611, pp. 1-28, Published: Feb. 11, 2020.

"International Preliminary Report on Patentability for PCT/US2020/043140", issued by The International Bureau of WIPO dated Feb. 3, 2022.

"The Safe Blues Experiment at UoA", Safe Blues | 2021 Experiment, https://safeblues.org/experiment/ [Online], pp. 1-4, Retrieved Apr. 22, 2022.

Dandekar, et al., "Safe Blues: The case for virtual safe virus spread in the long-term fight against epidemics", Perspective, vol. 2, Issue 3, 100220, Mar. 12, 2021.

Firth, et al., "Combining fine-scale social contact data with epidemic modelling reveals interactions between contact tracing, quarantine, testing and physical distancing for controlling COVID-19", Medrxiv, pp. 1-26, Posted: Jul. 2, 2020.

Klepac, et al., "Contagion! The BBC Four Pandemic—The model behind the documentary", Epidemics, vol. 24, pp. 49-59, Sep. 2018.

Yoneki, et al., "EpiMap: Towards quantifying contact networks for understanding epidemiology in developing countries", Ad Hoc Networks, vol. 13, Part A, pp. 83-93, Feb. 2014.

* cited by examiner

HEALTH DATA AGGREGATION AND OUTBREAK MODELING

CROSS REFERENCE TO RELATED APPLICATIONS

This application is a Continuation of U.S. Non-Provisional application Ser. No. 16/936,278 filed Jul. 22, 2020, which claims the benefit of U.S. Provisional Application Nos. 62/877,773 filed Jul. 23, 2019 and 62/877,754 filed Jul. 23, 2019. The entire contents of the above-identified applications are hereby fully incorporated by reference.

REFERENCE TO AN ELECTRONIC SEQUENCE LISTING

The contents of the electronic sequence listing ("BROD-4300US_ST25.txt"; Size is 1,387 bytes (4 KB on disk) and it was created on Sep. 29, 2020) is herein incorporated by reference in its entirety.

TECHNICAL FIELD

The technology disclosed herein is related to using aggregated health data and outbreak models to conduct differential diagnosis and provide risk assessments. Particular examples relate to using data from user computing device applications and wireless communication technology to understand both virtual and actual outbreaks and provide user-health assessments based on user health data, user histories, and the outbreak model.

BACKGROUND

Public health policies are directed toward conducting infectious disease outbreak surveillance, implementing diagnosis methods, and establishing containment strategies. User-specific diagnoses are not capable of using user location histories or user contacts. Current technologies do not integrate information flows that connect user histories, healthcare providers, vulnerable populations, and third-party actors that may be responsible in quarantine, treatment, information dissemination, and logistical activities. Healthcare providers, administrators of hospital information systems, genomic researchers, public health officials, quarantine and logistics personnel, and affected populations perform independent assessments and follow uncoordinated approaches to public health. Current technology only provides collected data from previous outbreaks or poorly performed computer extrapolations based on that limited data. The slow responses to a pending health concern may result in greater risk to the public.

Citation or identification of any document in this application is not an admission that such a document is available as prior art to the present invention.

SUMMARY

The technology described herein includes computer-implemented methods, computer program products, and systems to use aggregated health data and outbreak models to provide risk assessments. In some examples of the technology, a healthcare organization computing system server or device receives, from a user computing device associated with a user, a communication comprising user health data and user history data. Based in part on comparing user health data and user history data with health data and user histories from the plurality of other users, the server identifies a subset of users from a plurality of other users having a connectivity score above a threshold connectivity score. The server identifies common health data attributes from the user health data and the health data from the subset of other users and determines a health status of the user based at least in part on the connectivity score and common health data attributes. The server communicates the health status of the user to the user computing device to display to the user.

The healthcare organization computing system server receives one or more disease event parameters, from the outbreak organizer, dictating characteristics of a simulated outbreak of a simulated pathogen and a notification that a particular user computing device is participating in the disease event simulation. The server generates a set of user parameters associated with the particular user computing device participating in the simulated disease event, the set of parameters being based at least in part on the received parameters and comprising characteristics of the virtual pathogen and characteristics of the simulated user. The server communicates the set of user parameters to the particular user computing device and receives data regarding a spread of the virtual pathogen from the particular user computing devices. The server presents a user interface display of a model of the simulated disease event based on the received data.

The healthcare organization computing system server integrates monitoring of disease outbreak patterns and mechanisms with overall healthcare data aggregation that is shared among individual healthcare providers, public health officials, and researchers to more efficiently support surveillance, detection, and treatment activities.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 13 illustrates Panel A (left): Ebola 2018 simulation and Panel B (right): SARS-like 2019 simulation.

Figure 1:
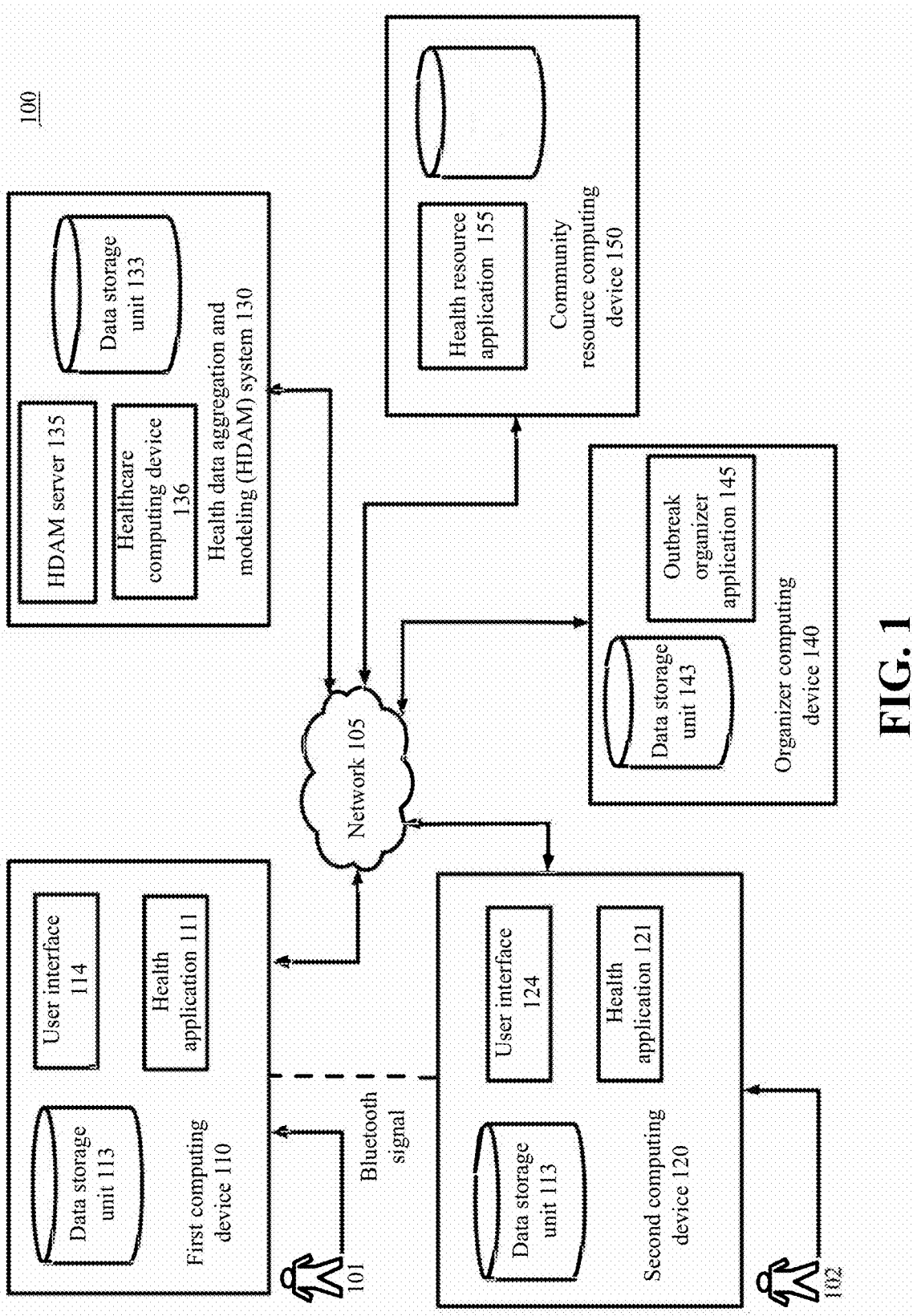
FIG. 1 is a block diagram depicting a portion of a simplified communications and processing architecture of a typical system to use aggregated health data and outbreak models to provide risk assessments, in accordance with certain examples of the technology disclosed herein.

The figures herein are for illustrative purposes only and are not necessarily drawn to scale.

DETAILED DESCRIPTION OF THE EXAMPLE EMBODIMENTS

Overview

In one aspect, technologies herein provide methods to automate health data extraction and diagnosis processes, and disease outbreak modeling that would allow individual users, healthcare providers, public health officials, and genomic and computational researchers to obtain, share, and interpret aggregate patient data faster and more efficiently, which may shorten the times between surveillance, detection, and treatment activities. In all these applications, the spatio-temporal modeling of the disease is critical to understand risk factors associated with transmission and, through this, adjust the magnitude and timing of the interventions in order to maximize their chance of success. In particular, predicting the epidemic risk of individuals to contract the disease over space and time can help to identify subpopulations under increased risk and to inform interventions such as quarantine. Most importantly, being able to promptly identify who, in a system, is at risk of infection during an outbreak is key to the efficient control of the epidemic. However, developing such models is challenging in a situation like the current pandemic, due to the uncertainty in the epidemiological parameters of a novel pathogen and also to the urgency with which interventions and tools are needed.

In one aspect, technology includes health applications for users to operate on user computing devices. The health application may be a downloadable application or application programming interface for use on a smartphone or other user computing device that receives health data and other data from a user. The data may include demographic data, contact data, location data, health data, and other suitable user data. The health data may include symptoms indicating an illness, such as an elevated temperature, coughing, congestion, or other symptoms of an illness. The location data may include the locations to which the user has traveled recently with the user computing device. The contact data may include the people the user interacts with and comes into contact with, whether via work, school, socially, or otherwise.

In another aspect, the technology includes applications and systems to model disease outbreaks. In certain example embodiments, the outbreak modeling may constitute a simulated event. For example, applications may be provided to individual users capable of communicating through wireless means and record interactions with other users in the simulation as well as interaction with other elements within the simulated environment. For example, application on the user computing device may use a wireless communication protocol, such as Bluetooth, to pass and receive "contact" with other user computing devices operating the health application or other wireless devices located within the simulated environment. Initial parameters regarding the pathogen and initial outbreak conditions can be defined and the outbreak modeled based on feedback provided for individual interactions recorded and shared with a centralized or de-centralized computing device. In other example embodiments, the individual interactions and initiation parameters may be based on real-world conditions and interactions between individuals in a given geographic area.

Further, the two aspects described above, are complementary and may be used in combination with one another. Thus, in yet another aspect, technologies disclosed herein provide methods for users to integrate monitoring of disease outbreak patterns and mechanisms with overall healthcare data aggregation that is shared among individual healthcare providers, public health officials, and researchers to more efficiently support surveillance, detection and treatment activities.

The terms "disease," "disease event," "outbreak," "epidemic," "pathogen," and other related terms are used interchangeably herein to describe a situation in which a contagion or other disease is spreading through a population. The disease spreads based on factors such as the type of pathogen, the contact between users, the locations or environmental conditions of users, and other suitable factors described herein.

The user may be required to enter an authorization—that is, provide affirmative input—to allow for utilization of the data. The user may opt to restrict the data from any uses, including uses that are part of the present technology or any other third-party uses. The user may apply any other restrictions to the use of the data to protect the privacy of the user and the data of the user.

Example Systems Architectures

Turning now to the drawings, in which like numerals represent like (but not necessarily identical) elements throughout the figures, example embodiments are described in detail.

FIG. 1 is a block diagram depicting a portion of a simplified communications and processing architecture of a typical system to use aggregated health data and perform outbreak modelling to provide risk assessments, in accordance with certain examples. In some embodiments, a user, such as user 101 or 102, associated with a user computing device 110 or 120 respectively, must install an application, such as health application 111 or 121, and/or make a feature selection to obtain the benefits of the techniques described herein.

As depicted in FIG. 1, the system 100 includes network computing devices 110, 120, 130, 140, and 150 that are configured to communicate with one another via one or more networks 105 or via any suitable communication technology.

Each network 105 includes a wired or wireless telecommunication means by which network devices (including devices 110, 120, 130, 140, and 150) can exchange data. For example, each network 105 can include a local area network ("LAN"), a wide area network ("WAN"), an intranet, an Internet, a mobile telephone network, storage area network ("SAN"), personal area network ("PAN"), a metropolitan area network ("MAN"), a wireless local area network ("WLAN"), a virtual private network ("VPN"), a cellular or other mobile communication network, Bluetooth, near field communication ("NFC"), ultra-wideband, or any combination thereof or any other appropriate architecture or system that facilitates the communication of signals, data. Throughout the discussion of example embodiments, it should be understood that the terms "data" and "information" are used interchangeably herein to refer to text, images, audio, video, or any other form of information that can exist in a computer-based environment. The communication technology utilized by the devices 110, 120, 130, 140, and 150 may be similar networks to network 105 or an alternative communication technology.

Each network computing device 110, 120, 130, 140, and 150 includes a computing device having a communication module capable of transmitting and receiving data over the network 105 or a similar network. For example, each network device 110, 120, 130, 140, and 150 can include a server, desktop computer, laptop computer, tablet computer, a television with one or more processors embedded therein and/or coupled thereto, smartphone, handheld or wearable computer, personal digital assistant ("PDA"), wearable devices such as smartwatches or glasses, or any other wired or wireless, processor-driven device. In the example embodiment depicted in FIG. 1, the network devices 110, 120, 130, 140, and 150 are operated by user 101, another participating user 102, healthcare organization operators, organizer operators, and community resource operators, respectively.

The user 101 can use a communication application on a user computing device 110, which may be, for example, a web browser application or a stand-alone application, to view, download, upload, or otherwise access documents or web pages via a distributed network 105. The user computing device 110 can interact with web servers or other computing devices connected to the network 105, including a web server of the healthcare organization system 130. In another example, the user computing device 110 communicates with devices in the healthcare organization system 130 via NFC or other wireless communication technology, such as Bluetooth, WiFi, infrared, or any other suitable technology.

The user computing device 110 uses a wireless technology to communicate with any other computing device participating in the outbreak model, such as second computing device 120. The wireless technology may be via NFC or other wireless communication technology, such as Bluetooth, WiFi, infrared, or any other suitable technology. The communication may be conducted even when different providers have provided the health applications 111, 121 or the user devices 110, 120. For example, the healthcare organization 130 may provide the health application 111, while a third-party provided the health application 121 on the second computing device 120. The two devices 110, 120 may still perform the methods herein because the two health applications 111, 121 are configured to recognize and communicate with other application types and other device types. Any provider of health applications 111, 121 may configure the health applications 111, 121 to communicate with each other, with the healthcare organization 130, or with any other suitable party or device.

The user computing device 110 includes a user interface 114 that is used to display a graphical user interface and other user interfaces. The user interface 114 may be used to display the health application 111 to the user 101.

The health application 111 provides information to the user 101 to allow the user 101 to interact with a second computing device 120, the healthcare organization system 130, a community resource computing device 150, and others. The health application 111 receives user input for health data and demographic data and displays results to the user 101. In certain examples, the health application 111 may be managed by the healthcare organization system 130. The health application 111 may be accessed by the user computing device 110. The health application 111 may display a webpage managed by the healthcare organization system 130. In certain examples, the health application 111 may be managed by a third-party server configured for the purpose. In certain examples, the health application 111 may be managed by the user computing device 110 and be prepared and displayed to the user 101 based on the operations of the user computing device 110. Any suitable application format may be utilized.

The health application 111 may be used to display a graphical user interface to the user 101 to receive health data and provide notifications to the user 101, as described herein.

The user computing device 110 also includes a data storage unit 113 accessible by the user interface 114, the health application 111, or other applications. The example data storage unit 113 can include one or more tangible computer-readable storage devices. The data storage unit 113 can be stored on the user computing device 110 or can be logically coupled to the user computing device 110. For example, the data storage unit 113 can include on-board flash memory and/or one or more removable memory accounts or removable flash memory. In certain embodiments, the data storage unit 113 may reside in a cloud-based computing system.

A user 102 represents one or more other users that interact with the user 101, lives in a geographic region with the user 101, participates in the outbreak model with the user 101, or performs any other actions in conjunction with the user 101. The one or more users 102 are each associated with one or more participating computing devices 120. Throughout the specification, the user 102 and the second computing device 120 are represented as either one particular user, multiple users, or a group of users. When described as a single user 102, the specification should be interpreted to describe how the user 101 interacts with one other participating user 102 or with multiple participating users 102.

The user 102 can use a communication application on a second computing device 120, which may be, for example, a web browser application or a stand-alone application, to view, download, upload, or otherwise access documents or web pages via a distributed network 105. The second computing device 120 can interact with web servers or other computing devices connected to the network 105, including a web server of the healthcare organization system 130. In another example, the second computing device 120 communicates with devices in the healthcare organization system 130 via NFC or other wireless communication technology, such as Bluetooth, WiFi, infrared, or any other suitable technology.

The second computing device 120 uses a wireless technology to communicate with any other computing device participating in the outbreak model, such as user computing device 110. The wireless technology may be via NFC or other wireless communication technology, such as Bluetooth, WiFi, infrared, or any other suitable technology.

The second computing device 120 includes a user interface 124 that is used to display a graphical user interface and other user interfaces. The user interface 124 may be used to display the health application 121 to the user 102.

The health application 121 performs functions substantially similar to the health application 111 of the user computing device. The health application 121 may be provided by the same provider as the health application 111, or the health application 121 may be configured to interact with health application 111. For example, the health application 121 may be provided by a different health organization, application provider, or outbreak modeling system, while still being configured to be compatible with health application 111.

The second computing device 120 also includes a data storage unit 123 accessible by the user interface 124, the health application 121, or other applications. The example data storage unit 123 can include one or more tangible computer-readable storage devices. The data storage unit 123 can be stored on the second computing device 120 or can be logically coupled to the second computing device 120. For example, the data storage unit 123 can include on-board flash memory and/or one or more removable memory accounts or removable flash memory. In certain embodiments, the data storage unit 123 may reside in a cloud-based computing system.

The organizer computing device 140 may include a data storage unit 143 and an outbreak organizer application 145. The example data storage unit 143 can include one or more tangible computer-readable storage devices, or the data storage unit may be a separate system, such as a different physical or virtual machine or a cloud-based storage service. In example herein, the organizer computing device 140 may be used by an organizer operator or other user. In other examples, the community resource operator may be a member of any other suitable body, such as a government entity, a private contractor, a private individual, or any other type of community resource operator. The organizer operator may or may not be associated with the healthcare organization 130.

The outbreak organizer application 145 provides information to an organizer operator to allow the organizer operator to interact with the healthcare organization system 130, the user computing device 110, and others. The outbreak organizer application 145 receives outbreak modeling data from the healthcare organization system 130 and other sources. In certain examples, the outbreak organizer application 145 may be managed by the healthcare organization system 130. The outbreak organizer application 145 may be accessed by the organizer computing device 140. The outbreak organizer application 145 may display a webpage managed by the healthcare organization system 130. In certain examples, the outbreak organizer application 145 may be managed by a third-party server configured for the purpose. In certain examples, the outbreak organizer application 145 may be managed by the organizer computing device 140 and be prepared and displayed to the health resource operator based on the operations of the organizer computing device 140. The functions of the outbreak organizer application 145 may be performed by any other computing device or system of the organizer computing device 140 or by the organizer computing device 140 itself.

The outbreak organizer application 145 may be used to display a graphical user interface to the organizer operator to configure, manage, and report an outbreak simulation, as described herein.

A health data aggregation and modeling (HDAM) system 130 may comprise a health data aggregation and modeling (HDAM) server 135, a healthcare computing device 136, and a data storage unit 133. In examples, the HDAM server 135 communicates with the user computing device 110, second computing device 120, organizer devices 140, and the community resource computing device 150 to transmit and receive health data and other useful data. The HDAM server 135 analyzes health data from users 101 and other sources, aggregates the data, builds models of infection outbreaks, determines location profiles of outbreaks, detects health trends, or performs any other suitable tasks.

The healthcare organization system 130 may employ healthcare computing device 136 to interact with one or more healthcare organization operators or users. The healthcare computing device 136 may be used to display a graphical user interface, such as an outbreak user interface, to the outbreak organizer or other operator to receive outbreak data and provide notifications to the outbreak organizer, as described herein. The healthcare computing device 136 may be a traditional computing device or only a user interface that is associated with the HDAM server 135.

In an example, the data storage unit 133 can include any local or remote data storage structure accessible to the healthcare organization system 130 suitable for storing information. In an example embodiment, the data storage unit 133 stores encrypted information.

In the examples herein, the healthcare organization system 130 is described as hosting or providing the HDAM server 135, the healthcare computing device 136, or other devices or applications. Alternatively, other third-party providers may host or provide these devices or applications. For example, a third-party server may be employed to operate the HDAM server 135 and report the model outcomes to the healthcare organization 130. In another example, the outbreak organizer may be a third-party organizer and not a part of the healthcare organization 130. In certain examples, a distributed organization, a group of organizations, or unrelated organizations may be represented herein by the actions of the healthcare organization 130. A single healthcare organization 130 is used for illustrative purposes.

The community resource computing device 150 may include a data storage unit 157 and a health resource application 155. The example data storage unit 157 can include one or more tangible computer-readable storage devices, or the data storage unit may be a separate system, such as a different physical or virtual machine, or a cloud-based storage service.

The health resource application 155 provides information to the health resource application 155 to allow a health resource operator to interact with the healthcare organization system 130, the user computing device, and others. The health resource application 155 receives updates on community health concerns from the healthcare organization system 130 and other sources. In certain examples, the health resource application 155 may be managed by the healthcare organization system 130. The health resource application 155 may be accessed by the health resource computing device 150. The health resource application 155 may display a webpage managed by the healthcare organization system 130. In certain examples, the health resource application 155 may be managed by a third-party server configured for the purpose. In certain examples, the health resource application 155 may be managed by the health resource computing device 150 and be prepared and displayed to the health resource operator based on the operations of the health resource computing device 150. The functions of the health resource application 155 may be performed by any other computing device or system of the health resource computing device 150 or by the health resource computing device 150 itself.

The health resource application 155 may be used to display a graphical user interface to the health resource operator to receive health data and provide notifications to the health resource operator, as described herein.

Throughout the application, actions taken by a user 101 on a user computing device 110, or one or more users 102 on one or more participating computing devices 120 may be examples representing any number of users or computing devices. The model may include 1, 10, 1000, or many more computing devices participating in the model development. The examples herein may include an interaction between a single user computing device 110 and a single second computing device 120, but the model may be created or modified based on many hundreds or thousands of interactions between computing devices.

It will be appreciated that the network connections shown are examples, and other means of establishing a communications link between the computers and devices can be used. Moreover, those having ordinary skill in the art having the benefit of the present disclosure will appreciate that the healthcare organization system 130, community resource computing devices 150, the second computing device 120, the organizer computing device 140, and the user computing device 110 illustrated in FIG. 1 can have any of several other suitable computer system configurations. For example, a user computing device 110 embodied as a mobile phone or handheld computer may not include all the components described above.

Figure 9:
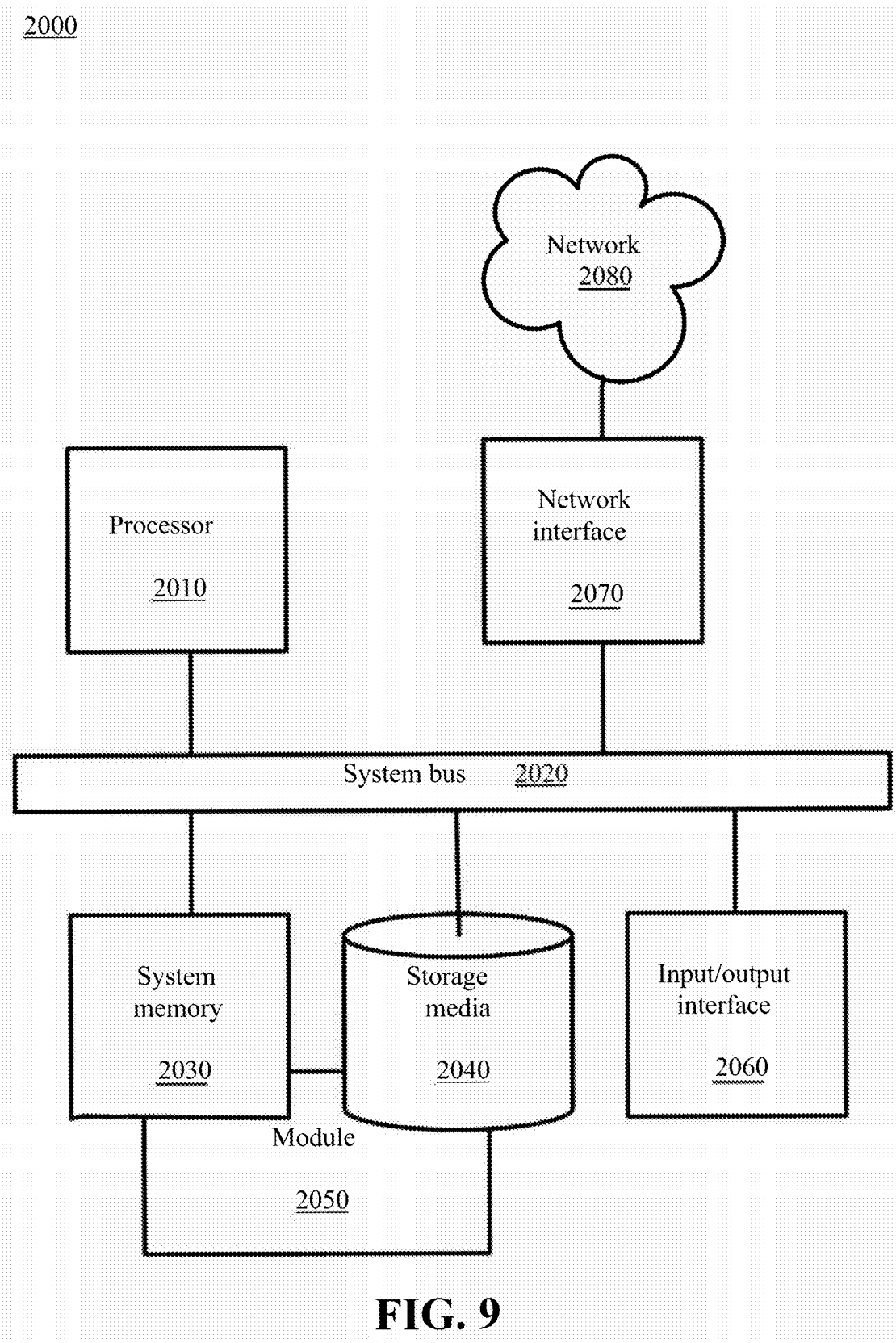
FIG. 9 is a block diagram depicting a computing machine and modules, in accordance with certain examples of the technology disclosed herein.

In example embodiments, the network computing devices and any other computing machines associated with the technology presented herein may be any type of computing machine such as, but not limited to, those discussed in more detail with respect to FIG. 9. Furthermore, any modules associated with any of these computing machines, such as modules described herein or any other modules (scripts, web content, software, firmware, or hardware) associated with the technology presented herein may be any of the modules discussed in more detail with respect to FIG. 6. The computing machines discussed herein may communicate with one another as well as other computer machines or communication systems over one or more networks, such as network 105. The network 105 may include any type of data or communications network, including any of the network technology discussed with respect to FIG. 9.

EXAMPLE PROCESSES

The example methods illustrated in FIGS. 2-5 are described hereinafter with respect to the components of the example architecture 100. The example methods also can be performed with other systems and in other architectures including similar elements.

User Health Care Data Aggregation

Figure 2:
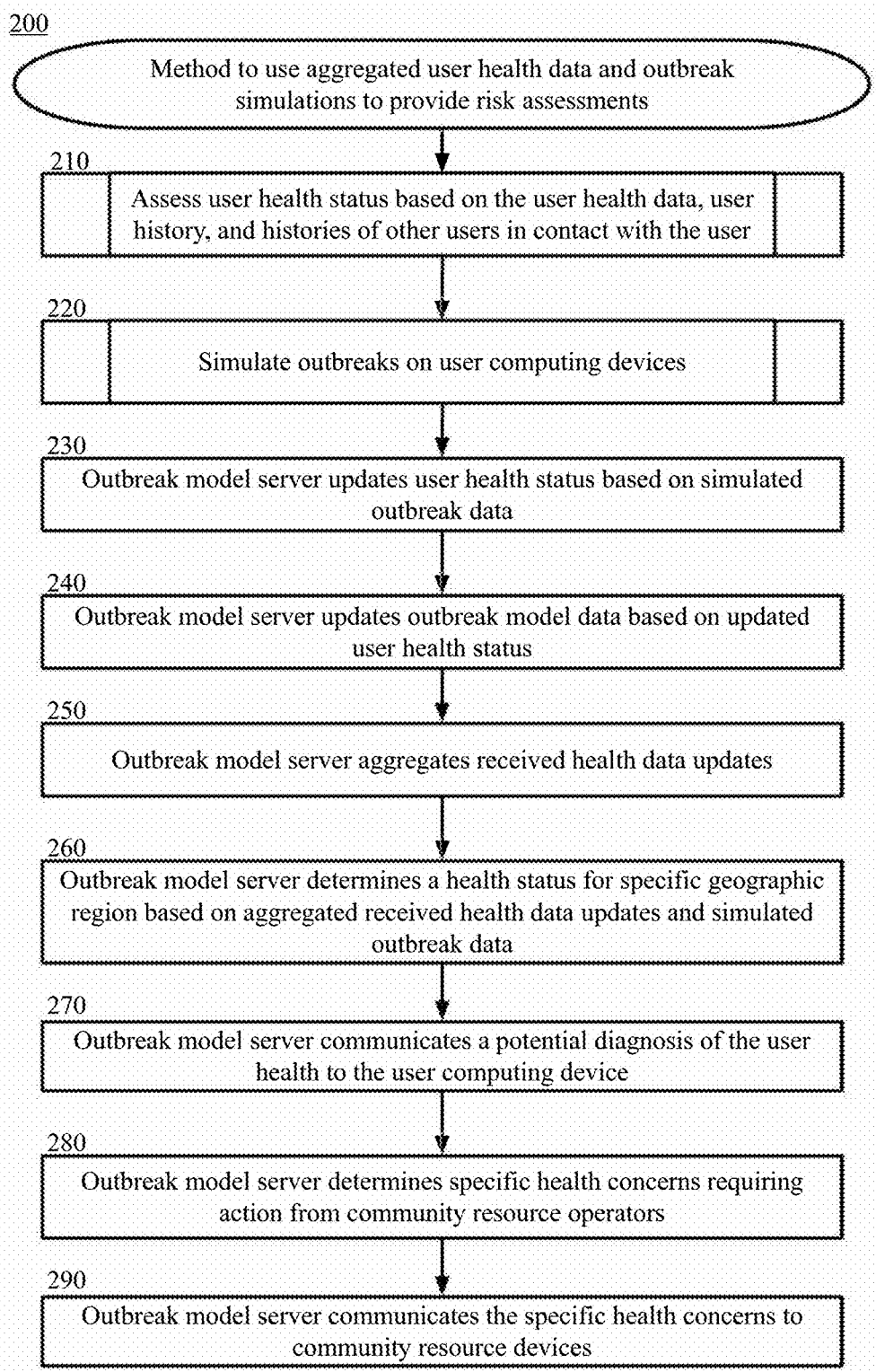
FIG. 2 is a block diagram depicting methods to use aggregated user health data and outbreak simulations to provide risk assessments, in accordance with certain examples of the technology disclosed herein.

Referring to FIG. 2, and continuing to refer to FIG. 1 for context, a block diagram illustrates methods 200 to use aggregated health data to provide health assessments, in accordance with certain examples of the technology disclosed herein.

In block 210, the healthcare organization 130 accesses user health status based on the user health data, user history, and histories of other users in contact with the user. Block 210 is described in greater detail with respect to FIG. 3.

Figure 3:
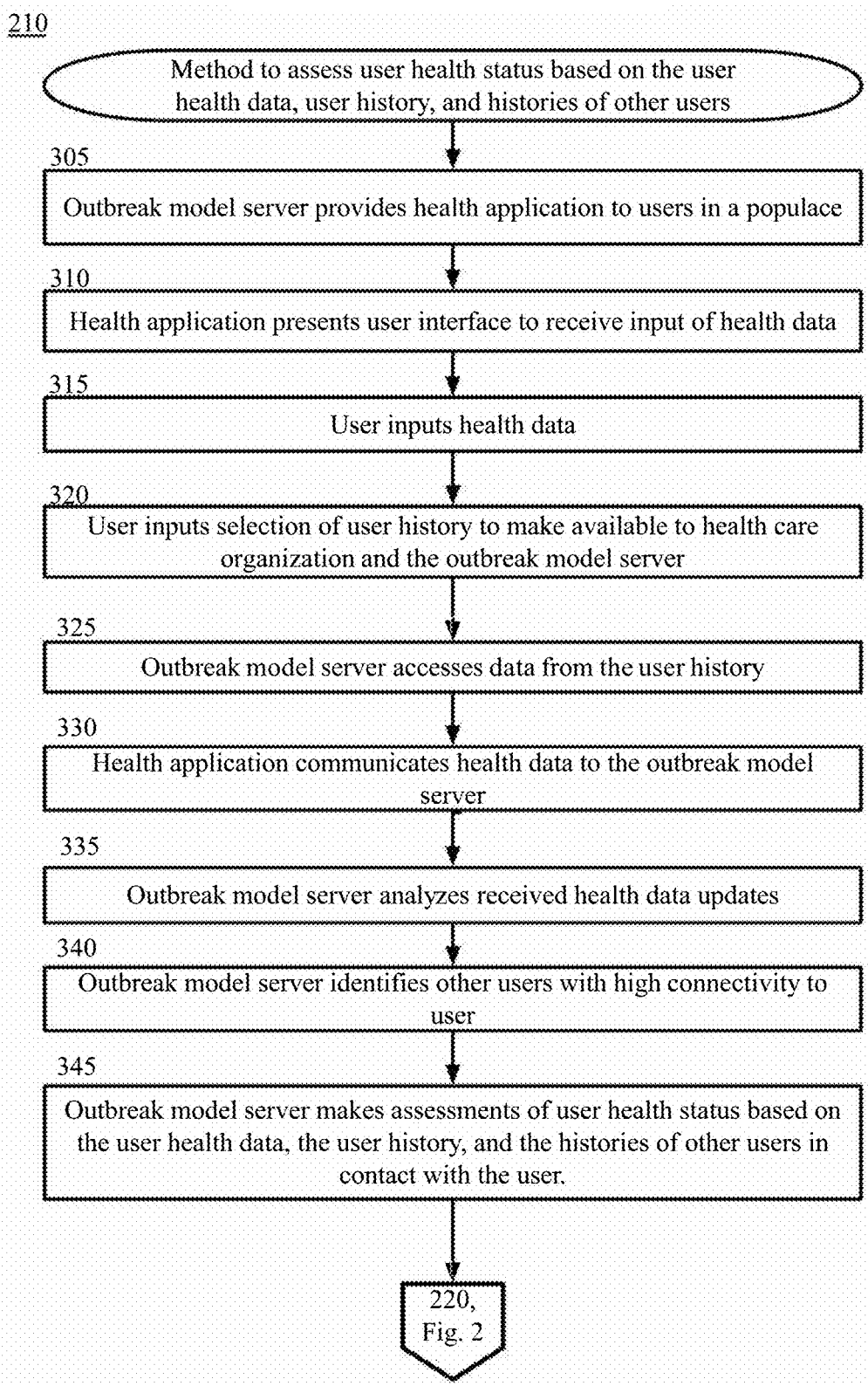
FIG. 3 is a block diagram depicting methods to assess user health status based on the user health data, user history, and histories of other users, in accordance with certain examples of the technology disclosed herein.

FIG. 3 is a block diagram illustrating methods 210 to access user health status based on the user health data, user history, and histories of other users in contact with the user, in accordance with certain examples of the technology disclosed herein.

In block 305, the HDAM server 135 of a healthcare organization 130 provides a health application 111 to users 101 for use in conjunction with the simulation. The health application 111 allows the HDAM server 135 to use actual health data of a user 101 in the simulation.

In the examples herein, the HDAM server 135 provides the health application 111 and performs a described health analysis of the user 101. However, this function could be provided by any suitable service, such as a health organization, a hospital, a doctor's office, a government organization, or any suitable organization.

The health application 111 may be downloaded to a user computing device 110 from any available source, such as the HDAM server 135, an application provider associated with the user computing device provider, a network service provider, or a third-party server. The health application 111 may be an application that operates on the user computing device 110 or the health application 111 may be a function of a webpage of the HDAM server 135 or another suitable party.

In block 310, the health application 111 presents a user interface 114 to a user 101 to receive input of health data. In an example, the health application 111 presents a series of data entry screens that allow the user 101 to input data about the user 101 and the health of the user 101. The health application 111 may be initiated when a user 101 actuates a visual icon or otherwise performs an action to initiate the health application 111. The health application 111 may utilize text entry, point and click entry, voice entry, gesture entry, or any other suitable data entry format.

In block 315, the user 101 inputs health data. The user 101 enters health-related data to be used in the diagnosis or prognosis of an illness. For example, the user 101 may enter symptoms of an illness such as elevated temperature, coughing, congestion, headache, vomiting, or other symptoms of an illness. The entry may be based on a pull-down list from which the user 101 selects entries on the user interface 114. In another example, the user 101 enters the data via a text entry. In another example, a series of symptoms are provided in a checklist from which the user 101 checks relevant symptoms. The entry of the symptoms may be in any other suitable manner, such as voice recognition. The health application 111 may continuously or periodically update the list of symptoms as other symptoms are entered. For example, the first symptom entered may trigger other possible symptoms to be added to the list of options.

In block 320, the user inputs a selection of user history, which may be in the form of a drop-down menu or other suitable visual presentation, to make available to the HDAM server 135. The user history data may include demographic data, contact data, location data, health data, and other suitable user data. The location data may include the locations at which the user has been recently with the user computing device 110 based on GPS data, user-inputted data, or any other suitable location determining data. The contact data may include the people the user 101 interacts with and comes into contact with, whether via work, school, socially, or otherwise. For example, the contact data may be extracted from user email lists, social media data, or other suitable locations. The user 101 may be requested to allow permission for any data extracted by the health application 111. For example, the health application 111 may request permission to interact with a particular social media account of the user 101.

In an alternate or additional example, the HDAM server 135 may identify and use data from an outbreak model. The creation and use of the outbreak model are described in greater detail in the method 220 of FIG. 3. In this alternate or additional example, any data, such as the predictions, patterns, and analyses that the outbreak model provides, may be used to bias or inform the assessment of the user-health status. For example, the knowledge that the HDAM server 135 identifies regarding the likely infectivity rates of various simulated diseases may be used to predict if the user 101 has been exposed to an actual disease by using the model of user movements, interactions, and location history. The use of the outbreak model as an input in the method 210 herein is merely an example of data that may be used in the user-health status assessment.

The user history data may include a diagnosis history. Diagnosis history may comprise health data such as a clinical diagnosis derived from a variety of sources. In an aspect, the data can be derived from results of diagnostics and information collected, including at point-of-care analyses and real-time data collection, via self-testing, hospital and other clinical and healthcare testing, field data, and other related information sources. In an aspect, collected data can be combined with other user data, epidemiological, genomic (e.g. genotyping, whole genomic sequencing of target pathogen), location, self-assessments, and other data for input into the models and inputs of the present invention. Exemplary user history data can be as described in Gire et al., Science 12 Sep. 2014: 1369-1372, incorporated herein by reference, where genomic surveillance can be utilized to identify outbreak sources and transmission. In a preferred aspect, the surveillance can be for SARS-CoV-2 outbreaks, see, Metsky et al., "CRISPR-based COVID-19 surveillance using a genomically-comprehensive machine learning approach" doi 10.1101/2020.02.26.967026, incorporated herein by reference. SARS-CoV-2 is an example viral infection which can be detected, see, Broughton, et al. CRISPR-Cas12-based detection of SARS-CoV-2. Nat Biotechnol (2020), doi: 10.1038/s41587-020-0513-4 (DETECTR detection); however, one of skill in the art will appreciate the applicability of the current invention to a variety of applications, see, e.g. Gootenberg et al., Science. 2018 Apr. 27; 360(6387):439-444. doi: 10.1126/science.aaq0179 (multiplexing lateral flow platform for point-of-care diagnostics); and Chen, et al., Science. 2018 Apr. 27; 360(6387):436-439. doi: 10.1126/science.aar6245 (Cas12 detection), each of which is incorporated by reference. Similarly, data from field deployable technologies can be utilized in accordance with the present invention. See, Myrhvold et al., Science 27 Apr. 2018: 360:6387, pp. 444-448; doi:10.1126/science.aas8836 (field deployable viral diagnostics), incorporated herein by reference. Point-of-care testing is a preferred data source and may include population-scale diagnostics. See, e.g. Joung et al., Point-of-care testing for COVID-19 using SHERLOCK diagnostics" doi: 10.1101/2020.05.04.20091231; Schmid-Burgk, et al., "LAMP-Seq: Population-Scale COVID-19 Diagnostics Using Combinatorial Barcoding," doi: 10.1101/2020.04.06.025635, each of which is incorporated herein by reference. Screening results for multiple pathogens may also be included in the diagnosis history. See, International Patent Publication WO2020102610, describing diagnostic systems and methods for detection of high throughput multiplex detection of multiple pathogens, incorporated herein by reference.

In another example, the user history data may include family history or genetic data. For example, the user may provide access to results of a commercial genetic history program. The data may include a summary of the user's genetic origins or even a full genetic profile of the user 101. The user 101 may limit the access to only the portions of the genetic data in the interests of privacy. The family history may include specific health data about the family members of the user 101 or more generic family history, such as the ethnic or racial background of the user 101.

The user 101 may input demographic data to assist the healthcare organization system 130 with creating models and predicting trends. The demographic data may include the user location, age, gender, occupation, or any other suitable data. The user 101 may opt out of entering any data that is considered private or personal. In examples, the healthcare organization 130 may anonymize the user data or otherwise take steps to protect sensitive information (such as using a HIPAA compliant platform) of the user 101.

The user 101 may input permission to include user data in an outbreak model such as the one described herein. The user 101 may input authorization into a user interface 114 of the user computing device 110 for the healthcare organization 130 to use the data in modeling an outbreak on the HDAM server 135 or in any other suitable manner.

In block 325, the HDAM server 135 accesses data from the user history. The health application 111, the user device 110, or any suitable party allows access to the user history for each of the allowed user history applications. For example, if the user 101 allowed access to the GPS location data of the user device 110, the HDAM server 135 requests the data from the user computing device 110 and receives a communication of the location data. Alternatively, the user may allow access to contact beacon data. The user 101 may allow access to data obtained in an outbreak model. The outbreak model may be created as described in detail with respect to the method 220 of FIG. 4. The data received, created, or obtained by the HDAM server 135, the data and predictions from the model, user locations, user movements, user interactions, and any other suitable data from the method 220 of FIG. 4 may be received or retrieved by the HDAM server 135 for use in the method 210 as part of the user history.

In block 330, the health application 111 communicates health data to the HDAM server 135. After sufficient data is collected from the user inputs, the health application 111 transmits the data to the HDAM server 135 via any suitable technology. For example, the health application 111 may transmit the data to the HDAM server 135 via a network connection over the Internet, via a cellular signal, or via any other suitable technology. The health application 111 may require an affirmative input from the user 101 before communication of the data.

In block 335, the HDAM server 135 analyzes received health data updates. The HDAM server 135 extracts relevant data from the communications with the health application 111 to input into a triage algorithm, machine learning processor, or other triage system.

In block 340, the HDAM server 135 identifies other users with high connectivity to the user 101. For example, based on the received health data, the health organization system 130 identifies a subset of users from a plurality of other users having a connectivity score above a threshold connectivity score. That is, the HDAM server 135 examines the user contacts, location data, social network data, and other data to identify other users that are connected to the user 101. The HDAM server 135 assigns a connectivity score to each other user based on the connections to the user 101, such as the number of instances of communications between the user 101 and the other user, the amount of time spent in the same location, the number of different contact or social media applications in which the user 101 and the other user are connected, the number of similar symptoms the user 101 and the other user share, or any other type of connections between the two.

In an example, the HDAM server 135 may increase a connectivity score if a user 101 spends a greater amount of time in a certain location with another user. Further, the score may increase if the location in which the two were co-located is known to have been at a greater risk for infection, such as a location with a high volume of traffic or a higher percentage of infected.

In another example, each other user may have multiple connectivity scores based on different suspected diseases or infections. That is, if the healthcare organization 130 suspects that the user 101 may have been exposed to a highly contagious airborne pathogen, then a short contact with another user may have been sufficient for transmittal. If the health organization system 130 suspects that the user 101 may have been exposed to a pathogen that is only transmitted through contact with bodily fluids, then a long contact period in a suitable location with another user would be needed for transmittal. Therefore, the same other user may have a different score for each contagion or situation. If the other user was with the user 101 for 20 minutes at a coffee shop, then the other user may have a relatively high connectivity score for the highly contagious pathogen, but a relatively low score for the pathogen that is only transmitted through contact with bodily fluids.

In block 345, the HDAM server 135 makes assessments of user-health status based on the user health data, the user history, and the histories of other users in contact with the user. The HDAM server 135 extracts the data from the communication and determines if the user 101 has a likely illness or other condition, such as by comparing the data to a database of symptoms related to one or more illnesses. In an example, the HDAM server 135 enters the symptoms into an algorithm that generates a likely illness. In another example, the HDAM server 135 enters the symptoms into a machine learning model that generates a likely illness. Any other suitable manner of interpreting the symptoms and determining a likely illness may be employed by the HDAM server 135. In an example, if a user 101 entered health data that indicated that the user 101 was experiencing throat pain, painful swallowing, swollen tonsils, red spots on the roof of the mouth, and fever, then the healthcare organization 130 algorithm or model will determine that strep throat is a likely diagnosis. Different symptoms may return a different likely diagnosis.

In one example embodiment, a method for calculating an individual likelihood of infection is further described in Example 1, an individual-level model ("ILM") framework that enables an HDAM server 135 of a healthcare organization 130 to express the probability of a susceptible individual being infected as a function of their interactions with the surrounding infectious population while also allowing the HDAM server 135 to incorporate the effect of individually-varying risk factors (e.g., age, pre-existing conditions) in calculating an individual likelihood of infection. In the example, the HDAM server 135 first applies the formalism for ILMs to derive an expression for the marginal probability of individual risk of infection as a function of parameters with straightforward epidemiological interpretation and initial estimation. The HDAM server 135 incorporates symptoms and other individual-level data to update the risk of infection based on this new information. The HDAM server 135 then constructs a population-level compartmental SIR epidemic model, where the rate of infection can be estimated from the individual-level probabilities given a random sample of individuals from the population. This allows the system to express the population-level parameters as a function of the individual-level parameters, and to use partially observed data (overall case counts, and individual risk factors and contacts) to apply Maximum Likelihood Estimate (MLE) within a Partially Observed Markov Process (POMP) framework. The POMP framework enables us to solve a computationally more tractable MLE problem thanks to iterated filtering, an efficient computational method that's based on a sequence of filtering operations which are shown to converge to a maximum likelihood parameter estimate. As result of this approach, the HDAM server 135 arrives at estimates of individual-level parameters that can be used to predict risk of infection.

The HDAM server 135 compares the health data of the user 101 to health data of the user's contacts to scan and identify trends or common occurrences of medical and/or epidemiological importance. In an example, only other users with connectivity scores over the threshold are used in the analysis. For example, if the user 101 and a user's contact have similar symptoms, the user 101 and the contact have been in contact with one another, and the contact has been diagnosed with a particular illness, then the HDAM server 135 may use that data to bias a triage outcome for the user 101. The HDAM server 135 may determine that the user 101 is more likely to have the particular illness based on the contact's diagnosis.

The HDAM server 135 may use any received data from any usable source to improve the triage results. For example, if the location data of user 101 indicates that the user 101 has been working in a lab in which four other workers have been diagnosed with an illness, then the health organization system 130 takes that data into account when performing triage on the user data. The data may increase the likelihood that the user 101 has the same illness as their co-workers. The location data may further indicate that the user 101 has traveled through a known "hot spot" for a certain disease. For example, if the user data indicates that the user 101 went on a vacation and stopped over at an airport that had been identified as a likely transmission point for a certain infectious disease, then the health organization system 130 may use that information to bias the assessment of the user's health. The hot spot may be identified by cross-referencing the user locations against a list of hot spots or other high-risk locations that is maintained by a health monitoring organization, such as the Centers for Disease Control, the World Health Organization, or any other suitable organization.

In another example, the HDAM server 135 may use social media history of the user 101 to determine that six family members of the user 101 have been suffering similar symptoms and that all six of the family members ate together at the same restaurant the previous night, then the health organization system 130 may bias the triage to use this information when diagnosing the user 101. In this example, the HDAM server 135 may determine that the likelihood of food poisoning is increased due to this information.

In another example, many pathogens, particularly viruses, evolve rapidly as they infect the cells of the host. This is due, in part, to a high mutation rate for the virus. On a per-site level, viruses typically have mutation rates on the order of $10e^{-8}$ to $10e^{-4}$ substitutions per nucleotide site per cell infection (s/n/c). This genomic mutation rate is a parameter that researchers utilize in population genetic simulations. In the context of realistically simulating an outbreak, single-site mutations may resolve transmission chains and reconstruct the phylogeny of the pathogen during the outbreak. The parameters may mimic pathogen evolution in the simulation by incorporating a simple intra-host mutation model where the simulation seeds the outbreak with an ancestral genome, as part of the parameters of the simulation. This ancestral genome will correspond to a real reference genome for an existing viral or bacterial pathogen, and with each infection event during the simulation, the genome will be transmitted from the infected individual to susceptible individuals. Once the pathogen infects a new individual, the pathogen genome will undergo several single-site mutation rounds, according to the known mutation rate for that pathogen. Thus, single-nucleotide polymorphism or whole-genome sequence information may be used by the HDAM server 135 in the assessment. The HDAM server 135 may use this information to not only reconstruct phylogeny but further identify virus transmission chains and number of independent outbreak events.

Based on any or all of the described factors, the HDAM server 135 determines a likely or possible illness, disease, or other condition of the user 101.

In one example embodiment, where outbreak modeling is used to further help determine a health status of a geographic region as further described in blocks 260-290, the method 210 returns to block 220 of FIG. 2. In other example embodiments, where outbreak modeling is not incorporated, method 210 proceeds directly to block 250. Usage of the user-health status and data in the outbreak simulation is discussed in greater detail in block 240 in FIG. 2.

Outbreak Modeling

In block 220, the healthcare organization system 130 simulates outbreaks on user computing devices. Block 220 is described in greater detail in the method 220 of FIG. 4. It should be understood, that in certain example embodiments, the outbreak simulation noted in block 220 and described in FIG. 4 may be run independently of method 200 as a separate and stand-alone embodiment for modeling outbreaks, real or simulated.

Figure 4:
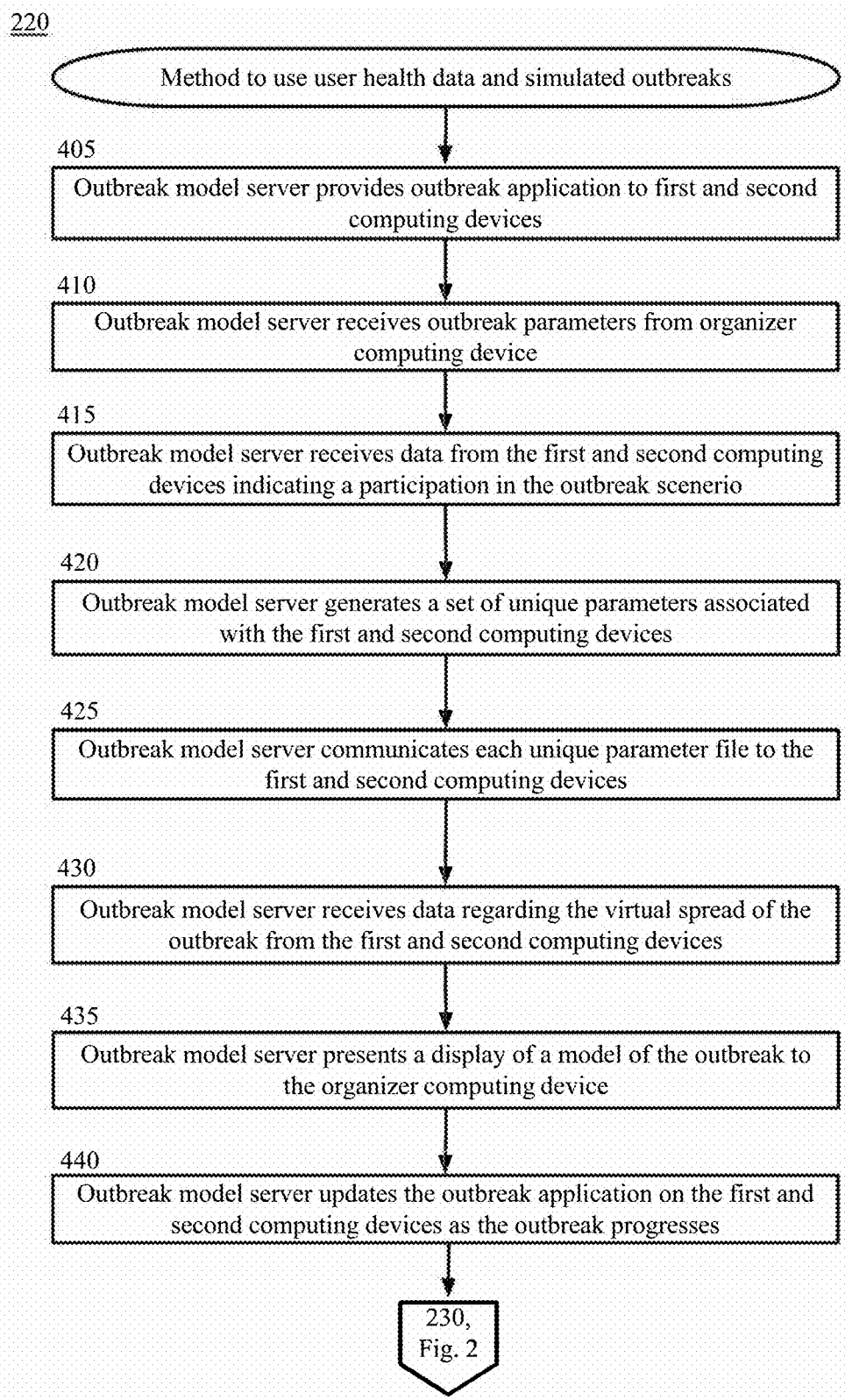
FIG. 4 is a block diagram depicting methods to simulate outbreaks on user computing devices, in accordance with certain examples of the technology disclosed herein.

FIG. 4 is a block diagram illustrating methods to simulate outbreaks on user computing devices, in accordance with certain examples of the technology disclosed herein.

In block 405 of FIG. 4, the HDAM server 135 provides a health application 111, 121 to users computing devices 110, 120 in a populace. The health application 111, 121 may be downloaded to a user computing device 110, 120 from any available source, such as the HDAM server 135, an application provider associated with the user computing device provider, a network service provider, or a third-party server. The health application 111, 121 may be an application that operates on the user computing device 110, 120 or the health application 111, 121 may be a function of a webpage of the HDAM server 135 or another suitable party. Where block 220 is carried out in the context of method 200, the health application 111, 121 may combine outbreak functionality with the data aggregation functionality described above. In examples herein, the multiple user computing device 110, 120 and other user computing devices of other participants may be represented by the single user computing device 110. In examples herein, the multiple health application 111, 121 and other outbreak applications of other participants may be represented by the single health application 111. The health application 111 is represented as being the same health application 111 used with respect to the methods of FIGS. 2 and 3. The functions of the health application 111 may be performed by the same health application 111 or by a separate application.

In one example embodiment, where outbreak modeling is used as a stand-alone embodiment independent of health data aggregation, the HDAM server 135 receives outbreak parameters from organizer computing device 140 at block 410. When a new simulation is desired, an organizer enters parameters on a computing device, such as the organizer computing device 140, operating an outbreak organizer application, such as outbreak organizer application 145. Alternatively, parameters can be assigned by the application or other third-party. The outbreak organizer application 145 presents a display to an organizer with options to configure parameters of a simulated outbreak. The display may be a presentation of the outbreak organizer application 145 on a user interface of the community resource computing device 150. The display may be a presentation of a list of parameters for configuring the outbreak organizer application 145 with the parameters being presented in a pull-down or drop-down list, a list of blanks to be populated, a pick list, or any suitable display that allows selections of parameters to be input by the organizer. The outbreak organizer application 145 receives the parameter selections from the organizer and communicates the parameters to HDAM server 135.

The organizer may enter parameters that include the type of infectious disease in the simulation, how contagious the disease is, how pathogenic the disease is, how the infectious disease is transmitted, how deadly the disease is, how long the recovery period is, how long a person is infectious, how much contact is required to transmit, and any other suitable factors. Detailed pathogen parameters may be included to more accurately simulate different types of pathogens and outbreak mechanics. For example, many pathogens, particularly viruses, evolve rapidly as they infect the cells of the host. This is due, in part, to a high mutation rate for the virus. On a per-site level, viruses typically have mutation rates on the order of $10^{-8}$ to $10^{-4}$ substitutions per nucleotide site per cell infection (s/n/c). This genomic mutation rate is a parameter that researchers utilize in population genetic simulations. In the context of realistically modeling an outbreak, single-site mutations may resolve transmission chains and reconstruct the phylogeny of the pathogen during the outbreak. The parameters may mimic pathogen evolution in the modeling by incorporating a simple intra-host mutation model where the simulation seeds the outbreak with an ancestral genome, as part of the parameters of the simulation. This ancestral genome will correspond to a real reference genome for an existing viral or bacterial pathogen, and with each infection event during the simulation, the genome will be transmitted from the infected individual to susceptible individuals. Once the pathogen infects a new individual, the pathogen genome will undergo several single-site mutation rounds, according to the known mutation rate for that pathogen.

In an additional or alternate example of the method 220, the HDAM server 135 may use any or all of the received data and assessed user health data described in greater detail in the method 210 of FIG. 3 in the creation or assignment of the parameters of the outbreak. That is, instead of receiving a set of or artificially defined outbreak parameters, the HDAM server 135 may use some or all of the actual inputted or collected user health data and/or epidemiological data from an actual disease outbreak. The usage of the actual user health data and/or epidemiological data from an actual disease outbreak is an alternative example embodiment and is not required in all example embodiments. The actual user health data and epidemiological data from an actual disease outbreak is merely one example of data that may be utilized to create the parameters of the outbreak. For example, if the outbreak model is being used to conduct a simulated outbreak, such as in a classroom environment, then the user-defined parameters may be used. If the outbreak model is being used to model an actual real-world outbreak, then the HDAM server 135 may use identified parameters associated with that particular outbreak, similar outbreaks or with models directed to the particular disease. The method 220 may be performed in either a real or simulated environment or in a virtual space. A combination of real and fictional parameters may also be used to create other models.

The organizer may enter environmental factors, such as how many treatment facilities are available in the region of the simulation, how many of the users are vaccinated, which pieces of personal protective equipment, such as a mask, are available, or any other suitable environmental factors. The organizer may enter operational factors such as the starting and stopping times, the number of participants, the geographic region of the simulation, or any other suitable factors. Each of these factors may dictate how, and if, a user 101 contracts or transmits the modeled disease to other users, such as user 102.

The organizer may input a parameter to determine if the outbreak simulation will be conducted in a virtual space or a physical space. For example, instead of using mobile devices that the user transports on his or her person, the model simulation may be conducted in a virtual space, such as a video game or other simulation of a virtual space. The simulated user is associated with an avatar or other representation of a person in the virtual space. The simulation occurs as the avatar moves about the virtual space and encounters avatars of other users. Each of the other features and functions of the simulation are performed as described herein, except the features and functions are performed in the virtual space with virtual characters.

In certain examples, the organizer is an actual person, or, optionally, a group of actual persons, that configures the outbreak simulation. In other examples, the organizer is a virtual organizer, such as a program, application, or other software or hardware technology that provides the organization parameters to configure the application. The virtual organizer may provide parameters randomly, following a certain schedule, or in any other suitable manner.

The outbreak organizer application 145 communicates the parameters to HDAM server 135. The outbreak organizer application 145 may transmit the data to the HDAM server 135 via a network connection over the Internet, via a cellular signal, or via any other suitable technology. The outbreak organizer application 145 may require an affirmative input from the organizer before communication of the data.

In block 415, the HDAM server 135 receives data from the first user computing device 110 and second user computing device 120 indicating a participation in the outbreak scenario. For example, a user 101 and a user 102 indicate that they are participating in the outbreak simulation via an input to the respective user computing device 110, 120. The user computing devices 110, 120 communicate the participation to the HDAM server 135 via any suitable communication technology, such as a network connection over the Internet.

The first user computing device 110 and second user computing device 120 represent any number of user computing devices in the simulation. In practice, the outbreak scenario may employ any suitable number of user computing devices associated with a corresponding number of users. For example, 20 user computing devices may be a minimum number of user computing devices to obtain an accurate model. In another example, a minimum of 100 or 1000 user computing devices may be required. A greater number of user computing devices in an outbreak simulation would create a more accurate model. Throughout the specification, a first user computing device 110 and second user computing device 120 represent a plurality of user computing devices.

In block 420, the HDAM server 135 generates a set of user parameters for a simulated user associated with each of the first user computing device 110 and the second user computing device 120. The set of user parameters is based on a simulation of a person in an outbreak. The set of user parameters describes a set of characteristics that a simulated person in the outbreak may encounter in an outbreak simulation. For example, the simulated characteristics might include a susceptibility of the user 101, 102 to the particular disease, a health status of the user 101, 102, a vaccination status of the user 101, 102, likelihood that a contact with the disease would be fatal, an initial outbreak status of the user 101, 102, or any other characteristic of a simulated user 101, 102.

In an example, the set of user parameters for user 101 in a simulated outbreak may include an initial status of a "not infected," healthy, non-vaccinated, or other suitable initial status. With these conditions, the user 101 may require a full exposure to the disease, and after contact the user 101 would have an 80% survival rate. In the example, user 102 includes an initial status of an "infected," non-vaccinated, elderly person with compromised health. With these conditions, the user 102 may expose anyone in contact to the disease, and the user 102 would have a 20% survival rate after the start of the simulation.

The set of user parameters may include other factors to allow the first user computing device 110 and second user computing device 120 to participate. For example, the set of user parameters may include start and stop times for the simulation, geographic boundaries of the simulation, and a description of the category of person that the user 101, 102 is representing in the simulation. In an example, the set of user parameters may include a list of activities the user 101, 102 is expected to perform during the simulation. For example, the user 101 may be instructed to perform the activities of an office worker during the simulation. The user 101 would take public transportation to an office building and perform simulated duties. Any other suitable daily activities may be simulated by the user 101 to obtain the goals of the simulation.

In another example, the set of user parameters in a simulated outbreak may include data related to the time that is elapsed during the simulation. For example, time may be temporally accelerated in the simulation to 10 times the normal rate of the disease progression. For example, if the disease normally takes two (2) days to become infectious after contraction, then the temporally-accelerated simulation would make a person infectious after 4.8 hours.

In an example, the set of user parameters is part of a unique parameter file for each user in the simulation. That is the set of user parameters are included in a file and associated with each user, such as user 101.

In block 425, the HDAM server 135 communicates each set of user parameters to the associated first user computing device 110 and second user computing device 120. The HDAM server 135 communicates the set of user parameters to the first user computing device 110 and second user computing device 120 via any suitable communication technology, such as a network connection over the Internet.

Each user 101 may initiate the wireless communication technology of the user computing device 110, such as a Bluetooth signal, NFC signal, WiFi signal, or other wireless signal. When the simulation begins, a user computing device 110 determines the initial outbreak status of the simulated user 110. For example, the user computing device 110 determines if the user 101 is initially sick, infected, healthy, or otherwise. The user 101 keeps the user computing device 110 on the user's person as the outbreak commences such that the user computing device 110 comes into contact with others, such as user 102 with user computing device 120, just as the user 101 does. When the user computing device 110 comes within range of another computing device 120, the wireless communication technologies of the two user computing devices 110, 120 communicate with each other. Additionally, the model logs a history of the location of the participating user computing devices 110, 120. The location data may provide an additional indication that one or more users, such as 101 and 102, have come into contact with each other.

The parameters of the disease as configured by the organizer dictate how close the two user computing devices 110, 120 must be before the disease is transmitted by one user computing device to the other. The parameters may dictate other requirements for transmission, such as how long the user computing devices 110, 120 must be within range of each other. If the user computing device 110 meets the requirements for transmission, the disease may be virtually transmitted from a user computing device 110 with the disease to a user computing device 120 that does not have the disease. In the examples wherein the simulation occurs in a virtual space, the disease may be transmitted when the avatars of two users are proximate to each other, in contract with each other, or in any other way able to transmit the disease.

When the outbreak model is being used to conduct a simulated outbreak, such as in a classroom environment, then the health application 111 for each user 101 may provide a display of a status of the user 101. The fictional status of the user 101 may indicate that the user 101 is healthy, has been exposed to the disease, has the disease, has suffered a fatality from the disease, or is recovered from the disease. The details of the display to the user 101 on the user computing device 110 are described in greater detail in the method 500 and FIGS. 5-8. At any health status, the health application 111 determines if the user 101 is infectious to other users 102. For example, a user 101 that has recovered from the disease—or is vaccinated—may no longer be susceptible to the disease, but may still be able to transmit the disease by, for example, co-interacting with an infected virtual object.

If the outbreak model is being used to model an actual outbreak, then the HDAM server 135 may use the outbreak model to assess and identify the health status of the user 101 as described in the method 200 of FIG. 2, such as described in block 270. If the outbreak model is used to assess an actual user health status, the HDAM server 135 may still utilize the display method as described in method 500 and FIGS. 5-8. In this example, instead of a fictional health status from a simulation, an actual health status as determined by the HDAM server 135 may be represented by the described displays or other suitable displays.

For simulated outbreaks, outbreak model may employ Bluetooth beacons or other wireless transmitters, such as NFC-based technology, to represent environmental factors in the geographic region. For example, a user may have to find a beacon to recover a virtual mask or vaccination. The beacon may indicate a hospital location or any other suitable location. In another example, in addition to a beacon, the outbreak simulation may employ a QR code or other machine-readable code to represent environmental factors in the geographic region. The user computing device 110 can scan a code and receive game add-ons, such as a virtual mask or vaccination. When the outbreak simulation is occurring in a virtual space, the beacon or the QR code may be represented by any virtual element to provide the environmental factors. For example, a facemask may be represented by a virtual facemask that the avatar identifies, secures, and actually places on the avatar's virtual face.

In block 430, the HDAM server 135 receives updated data regarding the spread of the outbreak from the first user computing device 110 and the second computing device 120. The health applications 111, 121 communicate updates of the user health continuously or periodically to the HDAM server 135. For example, the health application communicates a notification to the HDAM server 135 when the user 101 becomes "infected" by another user computing device 102. The communication may include the user computing device 102 that infected the user 101, the location of the infection, and the time of the infection. Other suitable details may be communicated to help build the model of the outbreak.

In examples wherein a genomic mutation rate parameter is set at a higher level, the simulation can use a simple model to estimate a number of cell infections per unit of simulation time, based on the biology of the pathogen. Thus, the pathogen's genome will be slightly different after each transmission event during the simulation. The outbreak application will allow specific users in the simulation (such as those playing as "health responders") to collect a virtual sample from infected individuals and retrieve the pathogen's genome to conduct computational analyses such as sequence-based diagnostics, BLAST alignments, contact tracing, and phylogeny reconstruction, all of which directly correlate with real-life scientific activities during an outbreak.

In block 435, the HDAM server 135 presents a display of a model of the outbreak to the organizer computing device 140. The HDAM server 135 aggregates the data and creates a model of the spread of the outbreak. The model is able to use the natural movements of the users and the interactions of the users to model real-life interactions and transmissions of a disease. By processing and analyzing the communications from the user computing devices 110, 120, the HDAM server 135 can model the speed, the geographic spread, the penetration in a populace, and other indicators of the outbreak.

The HDAM server 135 communicates the model to the organizer computing device 140. The communication may be via any suitable communication technology, such as a network connection over the Internet. The communication may include the raw data from the model for the organizer computing device 140 to interpret and present to the organizer. Alternatively, the HDAM server 135 may construct a suitable display of the model that is communicated directly to the organizer computing device 140 for display. Any other user or operator may receive a display of the model data on a computing device, such as a community resource operator on a community resource operator computing device 150.

When the outbreak model is being used to conduct a simulated outbreak, such as in a classroom environment, then the model simulates the outbreak that would happen under the configured conditions. The model is displayed to the organizer or any other party that desires to understand the mechanics and operations of the outbreak. If the outbreak model is being used to model an actual outbreak, then the HDAM server 135 may use the outbreak model in the process to assess and identify the health status of the user 101 as described in the method 200 of FIG. 2, such as described in block 270. The model may be used as an input for one or more parameters, factors, or other model characteristics in the assessment.

In block 440, the HDAM server 135 updates the health application 111, 121 on the first and second computing devices 110, 120 as the outbreak progresses. In one example the updates may include changes to the level of pathogenicity and transmissibility of the disease as it mutates or changes. In another example, the user profile may be updated to include a new vaccination or health status. Any suitable updates relevant to the outbreak may be communicated. When the outbreak model is being used to conduct a fictional outbreak, such as in a classroom and broader school environment, then the model may be provided with helpful analysis of the outbreak and useful tips for the user 101. For example, the model may be displayed to the user 101 to illustrate the importance of following proper protocols in an outbreak and suggested practices the user 101 should employ. If the outbreak model is being used to model an actual outbreak, then the HDAM server 135 may use the outbreak model to inform the user of the spread and dangers of the outbreak. For example, as described in blocks 270 and 280 of the method 200 of FIG. 2, the model may be used to inform the user 101 and/or health resource operators of the dangers of the outbreak and suitable actions to take.

In one example embodiment, where method 220 is run as a stand-alone embodiment, the method terminates at block 440. In another example embodiment, where method 220 is integrated within method 200, from block 440, the method 220 returns to block 230 of FIG. 2.

Integration of Aggregated Health Data and Modeling Data

In block 230, the HDAM server 135 updates user health status assessments based on modeled outbreak data. When the HDAM server assesses a user health status based on the user health data, user history, and histories of other users in contact with the user, the HDAM server may use data from outbreak model that is described in FIG. 4. The predictions, patterns, and analysis that the outbreak model provides may be used to bias or inform the assessment of the user health status. For example, the knowledge that the HDAM server 135 identifies regarding the likely spread rates of various simulated diseases may be used to predict if the user 101 has been exposed to an actual disease by using the model of user movements, interactions, and location history, and other suitable indicators.

In an example, the outbreak model may have data suggesting typical travel patterns on weekdays of a user 101. The data may have been obtained during an outbreak simulation in which the user 101 participated. The HDAM server 135 may use the information on movement patterns of the user 101 to help predict whether the user 101 is more or less likely to have contacted an infected person in a real outbreak. In another example, the HDAM server 135 does not have data for the user 101, but does have data for other users that are similarly situated to the user 101. The knowledge of travel patterns or other data of the other users may be used to predict the actions and likely diagnosis of the user 101. In another example, a model that predicts the spread rate of a particular disease may be used to determine if a user 101 was likely exposed to a disease in the case of an actual outbreak. The HDAM server 135 may use this prediction in the assessment of the user health status.

The use of the outbreak model as an input in the method 210 or in block 230 is merely an example of data that may be used in the user health status assessment. The method 210 may be performed in certain examples without input from the outbreak model.

In block 240, the HDAM server 135 updates outbreak model data based on the updated user health status. The HDAM server 135 may use actual health status data provided by the users 101, 102 to update and improve the outbreak model in real time. When the HDAM server 135 receives inputs of the actual spread of diseases as illustrated by the actual health status data that is provided based on the analysis as described in FIG. 3, the HDAM server 135 incorporates the inputs and uses the inputs to refine the model. For example, if the HDAM server 135 uses a machine-learning algorithm or process to create the model, the actual health status data may be used as training data for updating the outbreak model and creating new outbreak models.

In an example, the set of user parameters used to create the model may be based on actual characteristics of the user 101 as assessed with respect to FIG. 3. That is, the HDAM server 135 uses the health application 111 or other application on the user computing device 110 to allow users 101, 102 to provide actual health and user history data when participating in the outbreak simulation. The HDAM server 135 may use some or all of the user data in the set of parameters for the user 101. For example, the HDAM server 135 may use the age, health status, and location in the parameter data for the user simulation. The HDAM server 135 sets the user's parameters to reflect the actual user data. By using the user's actual data in the simulation, the user 101 will be able to correlate the results of the simulation to future actions of the user 101 when an actual outbreak occurs. The simulation will be more personal and applicable to the user 101 than by role-playing characters with different data. In some examples, the user parameters will consist of only actual user data, while in other examples the actual user data is combined with simulated user parameters.

When data is received during or after an actual outbreak, the data provided from the user 101 allows the outbreak model to be further trained with accurate data. The more accurately trained HDAM server 135 will create more accurate models in future simulations. Continued updates from users 101 allow the model to compare actual outcomes to predicted likelihoods to determine the progression of the outbreak and more accurately assess additional parameters of the outbreak. For example, if a user 101 had a long period of contact with an infected person but did not subsequently become infected, then the model may note that contact in a calculation to determine the contagiousness of the disease or in future models.

The use of the user health status as an input in the method 220 or in block 240 is merely an example of data that may be used in the outbreak model. The method 220 may be performed in certain examples without input from the user health status.

In block 250, the HDAM server 135 aggregates received health data updates. The HDAM server 135 combines the healthcare data and/or the determined likely illnesses to generate aggregated results. For example, the HDAM server 135 aggregates the assessments of the health status of the user 101, the user 102, and any other suitable number of users.

In an example, if a high percentage of users report the same symptoms, then the HDAM server 135 may determine that a single outbreak of a particular illness is likely and appropriate responses are needed. In another example, if users report many different symptoms that are unrelated, then the HDAM server 135 may determine that a single outbreak of a particular illness is not likely and appropriate responses are not needed. Any suitable method for aggregating the data may be utilized, such as entering the data into a database or by using a machine learning model. The aggregated statuses may be based on factors such as location, an age of users, or another common attribute of the users. For example, the HDAM server 135 may aggregate data from all users that are students of a particular school.

In block 260, the HDAM server 135 determines a health status for a specific geographic region based on aggregated received health data updates and simulated outbreak data. The healthcare organization 130 may determine a specific geographic region by selecting a region on a map program or algorithm. The healthcare organization 130 may determine a specific geographic region by identifying a particular city, zip/postal code, state, or other geographic regions, such as a college campus or a corporate facility.

The healthcare organization 130 identifies users 101 in that geographic region and determines if any of the identified users 101 have submitted health data. Based on the health data from the identified users 101, the healthcare organization 130 determines if any outbreak trends or other health data concerns are associated with the geographic region. For example, if a number of users 101 greater than a threshold are determined to have a specific infectious illness, then the geographic region is classified as experiencing an outbreak. If the number of users 101 with a specific infection illness is trending upwards, then the healthcare organization 130 may determine that an outbreak is imminent if a critical number of users 101 have the illness. In another example, the healthcare organization 130 determines that the geographic region is safe from a likely outbreak because the number of users 101 with a particular illness is below a threshold or because the determined illnesses for the users 101 are unrelated to one another.

In block 270, the HDAM server 135 communicates a potential diagnosis of the user health to the user computing device 110. Based on the determination of the likely illness of the user 101, the HDAM server 135 communicates the diagnosis to the user computing device 110. The HDAM server 135 transmits the data to the user computing device 110 via any suitable technology. For example, the HDAM server 135 may transmit the data to the user computing device 110 via a network connection over the Internet, via a cellular signal, or via any other suitable technology. The HDAM server 135 may require an affirmative input from the user 101 before communication of the data.

The HDAM server 135 may communicate the likely diagnosis along with a determined likelihood that the diagnosis is correct. Because many illnesses have similar symptoms and user input data may not be completely accurate, the HDAM server 135 may determine that two or more illnesses are possible. For example, the HDAM server 135 may communicate a notification that a diagnosis of influenza is 60% likely while a diagnosis of a common cold is 30% likely.

The user 101 may make an informed decision about appropriate steps to take based on the diagnosis. For example, if the likelihood of influenza is high, then the user 101 may elect to go to the healthcare organization 130 to receive treatment. If the likelihood is high that the illness is a common cold, the user 101 may elect to treat the cold with over-the-counter medicines.

In addition to the likely health status of the user 101, the HDAM server 135 communicates the geographic health status to the user computing device 110. The HDAM server 135 transmits the data to the user computing device 110 via any suitable technology. The communication may be in any suitable format to provide the user 101 with a health status of the geographic area to allow the user 101 to make an informed decision about appropriate actions to take. For example, the HDAM server 135 may inform the user 101 that the local town in which the user 101 lives has an outbreak of measles that is localized at the local elementary school. If the user 101 is not vaccinated against measles, then the user 101 can make a decision to avoid the school until the outbreak is contained. In another example, the HDAM server 135 informs the user 101 that 20% of the population of a college campus is likely to have influenza.

The user 101 may elect to stay home instead of attending classes until the outbreak ends.

The health status of the geographic area may be displayed to the user 101 in any suitable format. In an example, the health status is displayed on a map. The map may illustrate areas with higher-than-normal instances of an outbreak by highlighting that area or changing the color gradation of the area. In another example, the map may illustrate individual people that are ill by placing a pin over the residence of each individual. In another example, the map may draw a border around an area with higher-than-normal instances of an outbreak. In another example, a list of neighborhoods or streets with higher than normal instances of an outbreak may be displayed in a list. Any other suitable illustrative technique may be employed.

In block 280, the HDAM server 135 determines specific health concerns requiring action from community resource operators. Based on the aggregated data and the determination of a health status for a specific geographic region, the HDAM server 135 determines if actions need to be taken by community resource operators involved in the management and treatment of infectious diseases or other community health concerns, such as healthcare providers, administrators of hospital information systems, genomic researchers, public health officials, quarantine and logistics personnel, and affected populations.

The HDAM server 135 determines if actions are required based on factors such as the type of illness or contagion in the determined outbreak, the number of infected people in the population, the rate that the outbreak is increasing or decreasing, the time of year, events happening in the geographic region, or other suitable factors. Another example factor is the likely resistance to the illness of the population based on factors such as the age of the populace, the interactions of the populace with one another, the percentage of the populace with vaccinations, and other suitable factors.

Actions that may be required of the community resource operators include quarantining infected persons, educating the public, increasing staffing and clinical infrastructure at treatment locations, briefing government officials, notifying a populace of the situation, administering vaccines, and any other suitable actions.

In block 290, the HDAM server 135 communicates the specific health concerns to community resource computing devices 150. The community resource computing devices 150 utilize a health resource application 155 that may have similar functions as the health application 111. That is, the health resource application 155 may display to the community resource operator a status of the health of the geographic region. The health resource application 155 may have options to display specific actions that each community resource operator should take due to the current status. The health resource application 155 may display a list of options that community resource operators should take, which allows each operator to perform any or all of the actions. The health resource application 155 may display specifics of the health status that allow each community resource operator to make decisions about appropriate actions to take. Any suitable display that allows the community resource operators to take appropriate actions to the updated health status of the community may be employed.

The community resource operators take appropriate action in response to the specific health concerns. The community resource operators respond to the notification and take actions that help contain the outbreak, assist those affected, prevent further spread of a contagion, or perform any other suitable actions.

Integration between self-reporting applications, diagnostic analysis by healthcare organizations, and healthcare responders will lead to faster and cheaper detection of outbreaks and more engagement of the general public with infectious disease responses. Any of these features alone, or any combination of the features, would achieve faster and facile healthcare diagnoses and/or suitable responses. Receiving the user health data, analyzing the data, aggregating the data, and providing responses in real-time or near real-time achieves numerous benefits, namely alleviating suffering and reducing loss of human life. For example, users would receive faster diagnosis of a possible illness and health data of the local area around the user. The user can use this information to make more informed decisions about whether to go to work or school, or to stay home and possibly avoid contact with the pathogen. Healthcare responders receiving updated and real-time public healthcare data are able to make faster and more informed decisions about what actions should be taken to contain an outbreak. Health care organizations can use the real-time data to more effectively detect outbreaks and use more appropriate treatments and action plans. The integration of this data will allow outbreaks to be detected earlier, contained more effectively, and ended sooner.

Example 1 in the Working Examples section below provides one embodiment for how individual healthcare data may be aggregated to classify individual risk levels.

User Computing Device Simulation Health Displays

Figure 5:
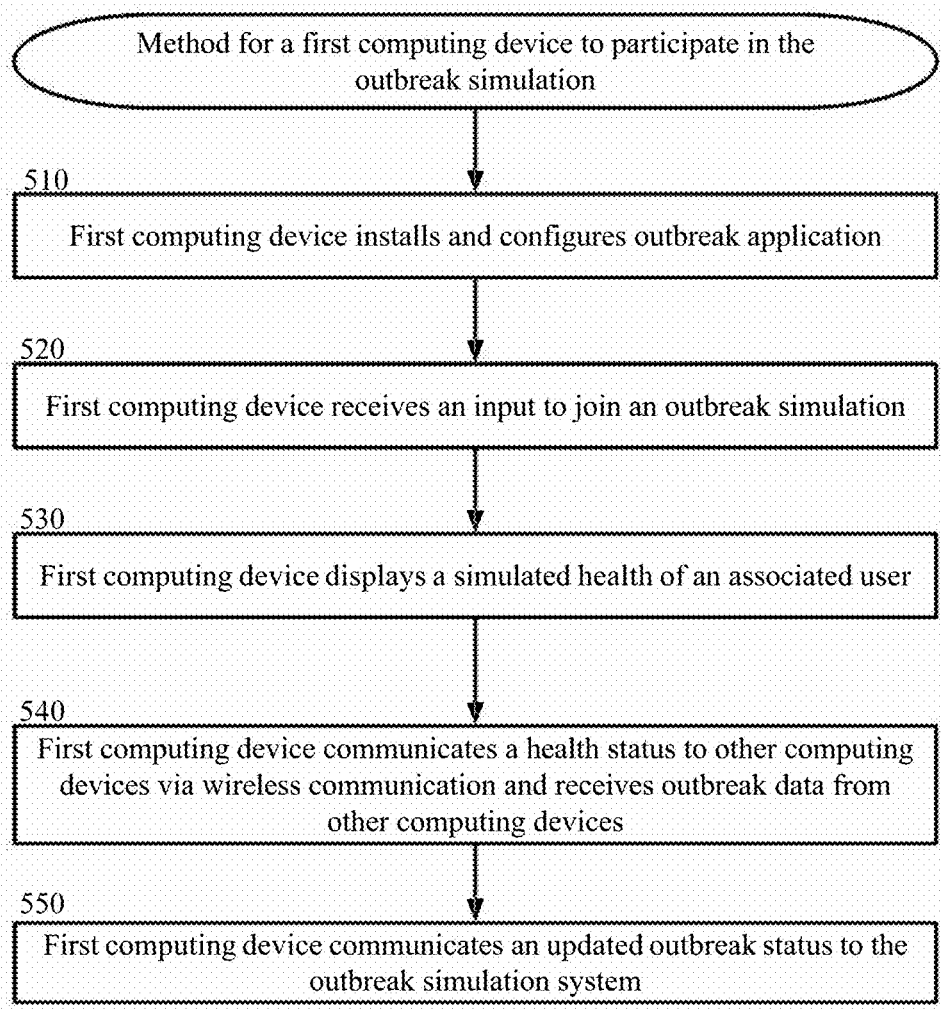
FIG. 5 is a block diagram depicting methods for a first computing device to participate in the outbreak simulation, in accordance with certain examples of the technology disclosed herein.

FIG. 5 is a block diagram illustrating methods for a first user computing device 110 to participate in the outbreak simulation or in a depiction of an actual outbreak scenario, in accordance with certain examples of the technology disclosed herein.

In block 510, the first user computing device 110 and the second user computing device 120 install and configure the health application 111, 121, as described herein. The functions of the devices 110, 120 and the health applications 111, 121 may be used interchangeably herein. That is, some actions described as being performed by the device 110 may be performed by the health application 111 and vice versa.

In block 520, the first user computing device 110 and the second user computing device 120 receive inputs to join an outbreak simulation. The input may be a voice command, a selection of an interface object, or any other suitable input.

In block 530, the first user computing device 110 and the second user computing device 120 display a simulated health of an associated user 101, 102. The simulated health may be in any suitable format. For example, the display may be a visual indication, such as a cartoon indication of a healthy person, a sick person, or a deceased person. The display may be color coded, such as a green background for a healthy person, yellow for a sick person, and red for a deceased person. The display may be a text display of the status or any other suitable display to communicate the status in a simple, clear format.

Illustrations of example depictions of the simulated health display are shown and described with reference to FIGS. 6-8 herein.

In block 540, the first user computing device 110 and the second user computing device 120 communicate a health status to other computing devices via wireless communication and receive outbreak data from other computing devices. In this continuing example, the actions are illustrated as being performed by the user computing device 110, however, the actions are being performed by each of the other user computing devices in the simulation. When the simulation begins, the user computing device 110 determines the initial outbreak status of the simulated user 101. For example, the user computing device 110 determines if the user 101 is initially sick, infected, healthy, or otherwise. The user 101 carries the user computing device 110 on the person of the user 101 as the outbreak commences. When the user computing device 110 comes within range of another computing device 102, the wireless communication technologies of the two user computing devices 110, 120 communicate with each other. The parameters of the disease as configured by the organizer dictate how close the two user computing devices 110, 120 must be before the disease is transmitted by one user computing device 110 to the other user computing device 120. The parameters may dictate other requirements for transmission, such as how long the user computing devices 110, 120 must be within range of each other and how strong the signal is between user computing devices 110, 120, using standard signal strength measures (e.g., received signal strength indicator). If the user computing device 110 meets the requirements for transmission, the disease may be transmitted from a user computing device 110 with the disease to a user computing device 120 that does not have the disease.

In another example, in addition to the wireless connection transmission, the user computing 110 may communicate or contract the disease based on a location of the user computing device 110 and other user computing devices. For example, if the user computing devices 110, 120 are close to each other based on a GPS location from each user computing device 110, 120, then the transmission of the disease may be assumed.

In an example wherein the simulation occurs in a virtual space, the user avatars contract or spread the disease based on factors such as how close the avatars get to each other or whether they come into contact with each other. Each of the examples listed above that are directed to the physical user interactions may be used in the virtual space. For example, if the disease parameters require that a user 101 be in contact with an infected user 102 for three seconds to contract the disease, then the virtual space may require the same degree of contact between avatars for three seconds to contract the disease.

In block 550, the first user computing device 110 and the second user computing device 120 communicate an updated outbreak status to the outbreak simulation system server 135. The outbreak applications 115, 125 communicate updates of the user health continuously, by way of 'push' notification or suitable notification technology, or periodically to the outbreak simulation system server 135. The updates may be communicated periodically or continuously. For example, the health application 111 communicates a notification to the HDAM server 135 when the user 101 becomes "infected" by another user computing device 102. The communication may include the user computing device 102 that infected the user 101, the location of the infection, and the time of the infection. Other suitable details may be communicated to help build the model of the outbreak.

Figure 6:
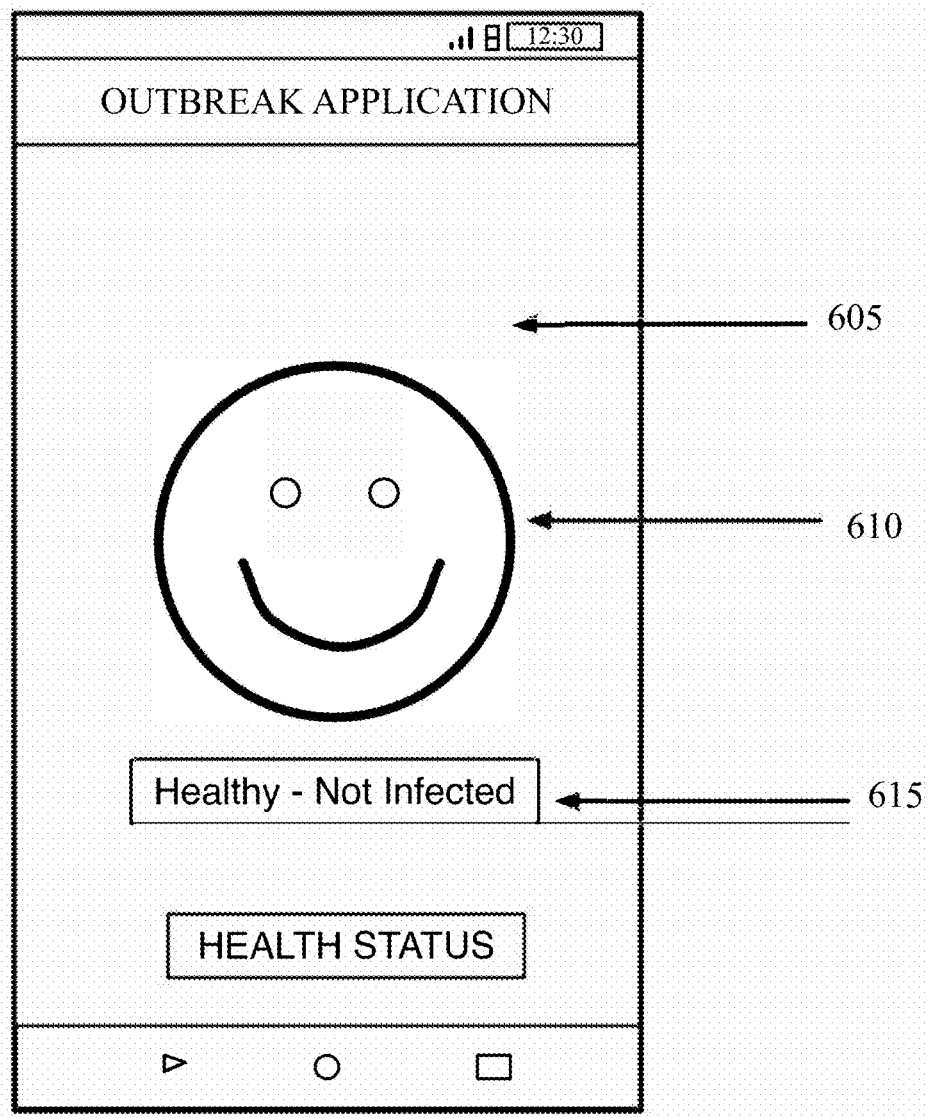
FIG. 6 is an illustration of a user computing device displaying a health status of healthy, in accordance with certain examples of the technology disclosed herein.
Figure 7:
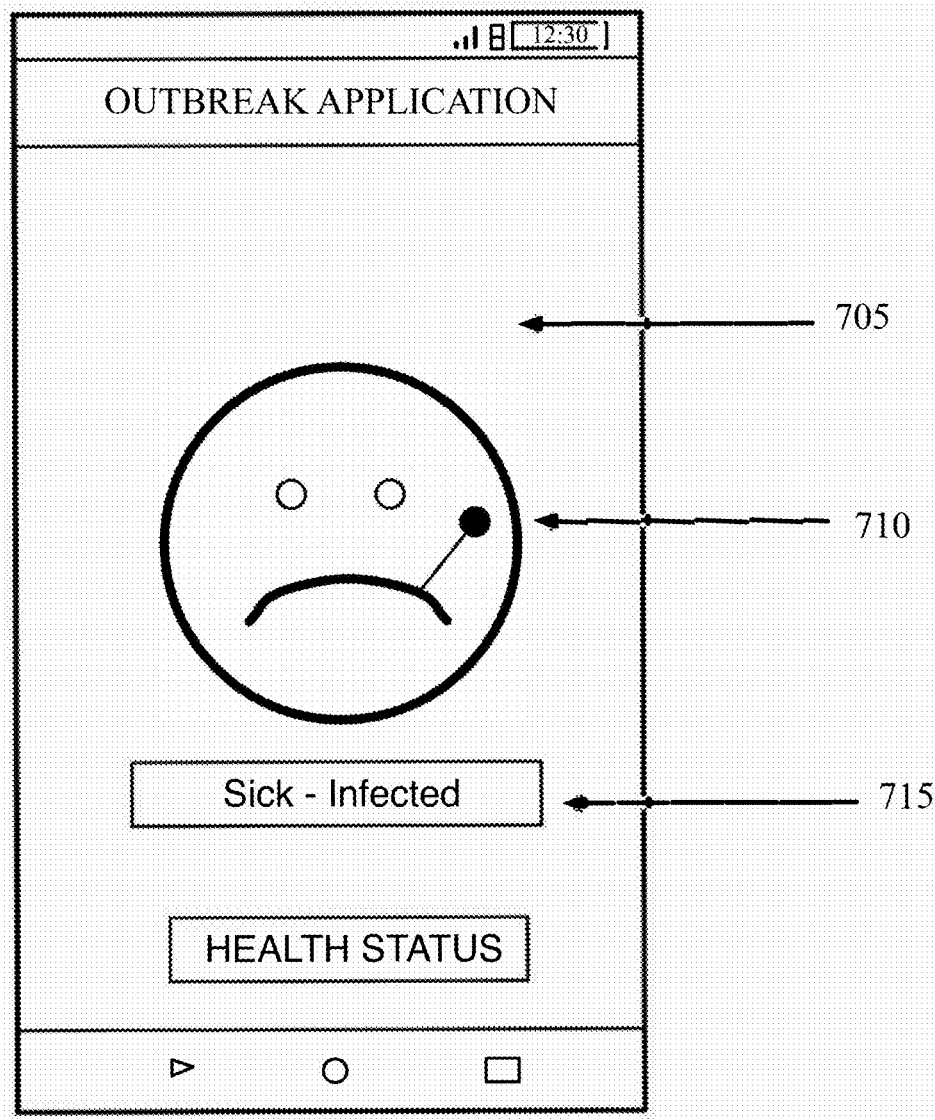
FIG. 7 is an illustration of a user computing device displaying a health status of infected, in accordance with certain examples of the technology disclosed herein.
Figure 8:
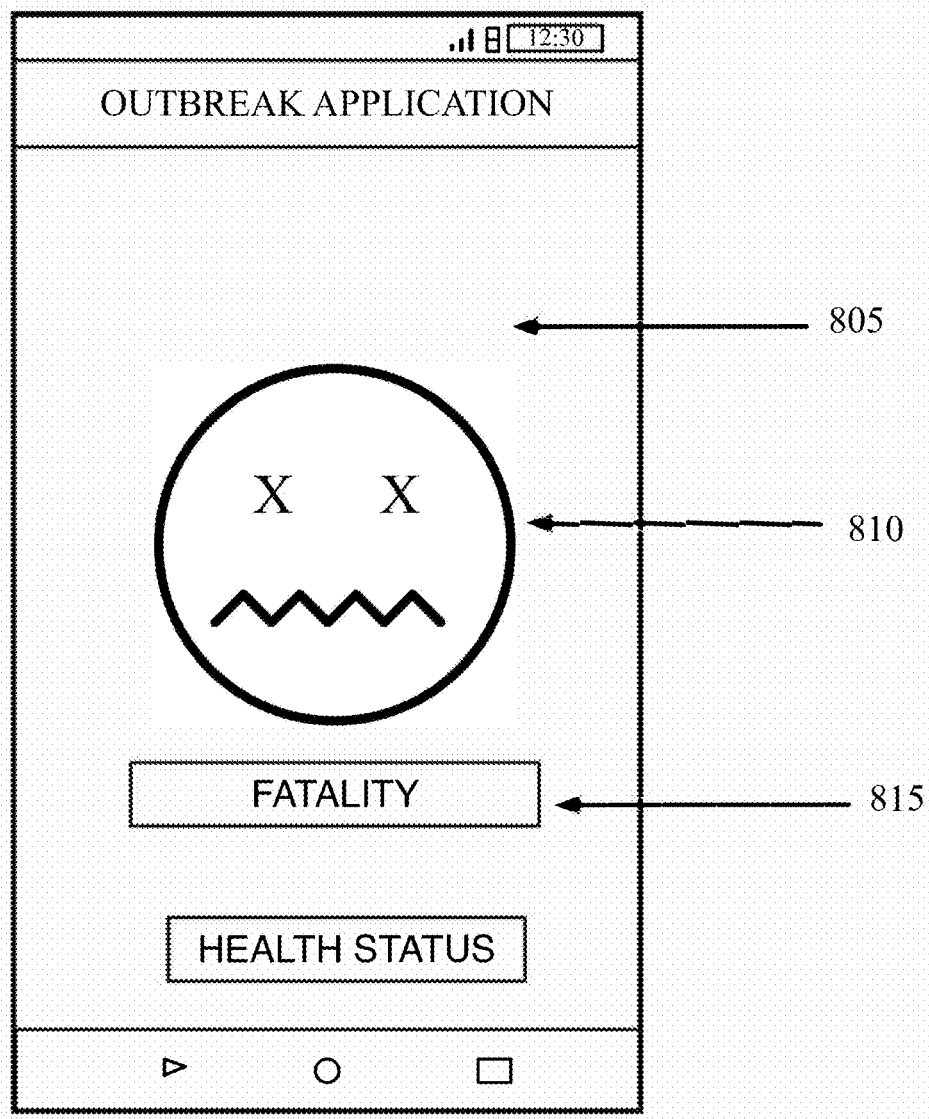
FIG. 8 is an illustration of a user computing device displaying a health status of deceased, in accordance with certain examples of the technology disclosed herein.

FIGS. 6-8 depict example illustrations of the simulation health displays.

FIG. 6 is an illustration 600 of a user computing device displaying a health status of healthy, in accordance with certain examples of the technology disclosed herein. In FIG. 6, a smartphone displays a user interface with a display of the health application. In the display, a smiley face 610 depicts a representation of a healthy user. The status is further illustrated by a text output 615 that specifies that the user is "healthy—not infected." Further, the health of the user may be indicated by a color in the background 605 of the illustration. For example, a healthy user may have a green background.

FIG. 7 is an illustration 900 of a user computing device displaying a health status of infected, in accordance with certain examples of the technology disclosed herein. In FIG. 7, a smartphone displays a user interface with a display of the health application. In the display, a sad face 710 with a thermometer in its mouth depicts a representation of an infected user. The status is further illustrated by a text output 715 that specifies that the user is "sick—infected." Further, the health of the user may be indicated by a color in the background 705 of the illustration. For example, a sick user may have a yellow background.

FIG. 8 is an illustration 800 for use in certain virtual modeling embodiments of a user computing device displaying a health status of deceased, in accordance with certain examples of the technology disclosed herein. In FIG. 8, a smartphone displays a user interface with a display of the health application. In the display, a face 810 with a cartoon depiction of a deceased person depicts a representation of a healthy user. The status is further illustrated by a text output 815 that specifies that the user is "Fatality." Further, the health of the user may be indicated by a color in the background 805 of the illustration. For example, a deceased user may have a red background.

FIG. 19-FIG. 27 are example illustrations of user interface displays for use in certain virtual modeling embodiments of a user computing device displaying a health status.

Figure 19:
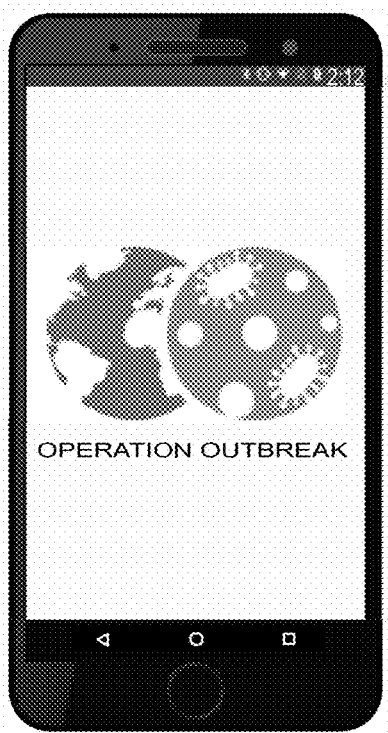
FIG. 19 is an example illustration of a user interface display of a start or overview screen of the health application.

FIG. 19 is an example illustration of a user interface display of a start or overview screen of the health application.

Figure 20:
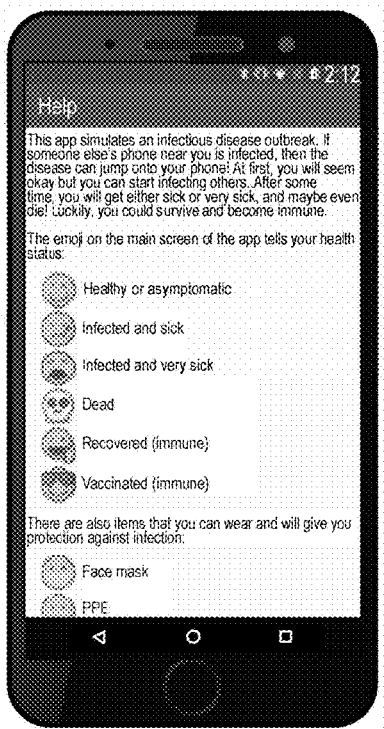
FIG. 20 is an example illustration of a user interface display of a help screen of the health application.

FIG. 20 is an example illustration of a user interface display of a help screen of the health application. The help screen includes general information for use of the health application. The help screen includes definitions of the icons that may be displayed on the user interface. Any other suitable data associated with operating the health application may be provided on the help screen.

Figure 21:
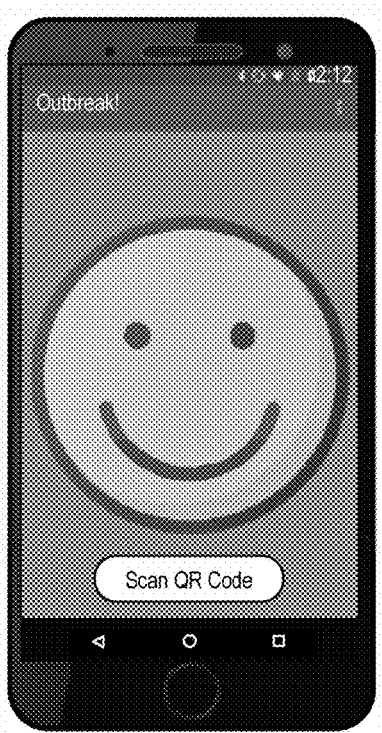
FIG. 21 is an example illustration displaying a health status of healthy or asymptomatic, in accordance with certain examples of the technology disclosed herein.

FIG. 21 is an example illustration displaying a health status of healthy or asymptomatic, in accordance with certain examples of the technology disclosed herein.

Figure 22:
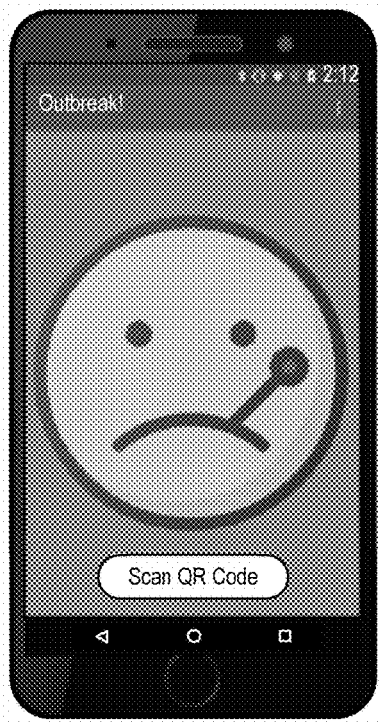
FIG. 22 displaying a health status of infected and sick, in accordance with certain examples of the technology disclosed herein.

FIG. 22 displaying a health status of infected and sick, in accordance with certain examples of the technology disclosed herein.

Figure 23:
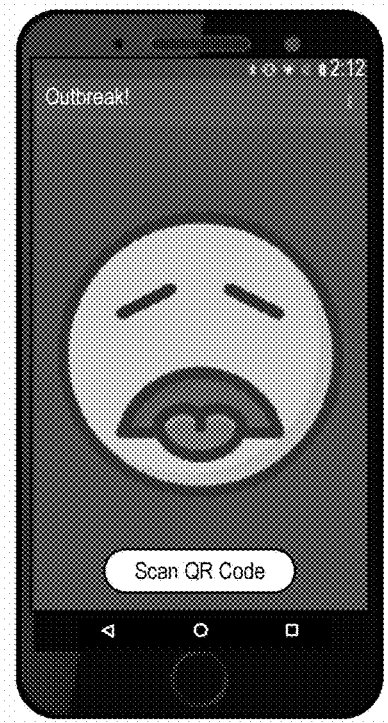
FIG. 23 displaying a health status of infected and very sick, in accordance with certain examples of the technology disclosed herein.

FIG. 23 displaying a health status of infected and very sick, in accordance with certain examples of the technology disclosed herein.

Figure 24:
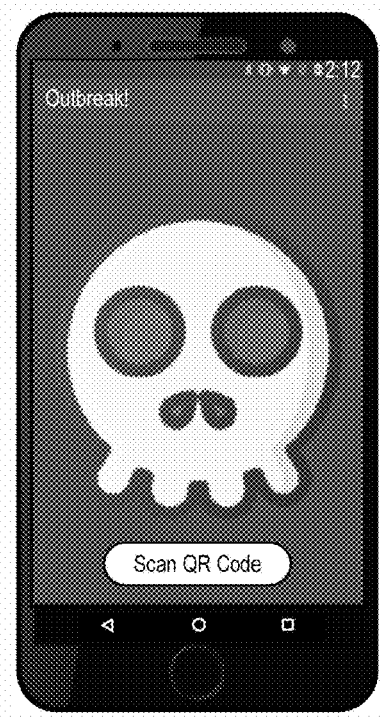
FIG. 24 displaying a health status of dead, in accordance with certain examples of the technology disclosed herein.

FIG. 24 displaying a health status of dead, in accordance with certain examples of the technology disclosed herein.

Figure 25:
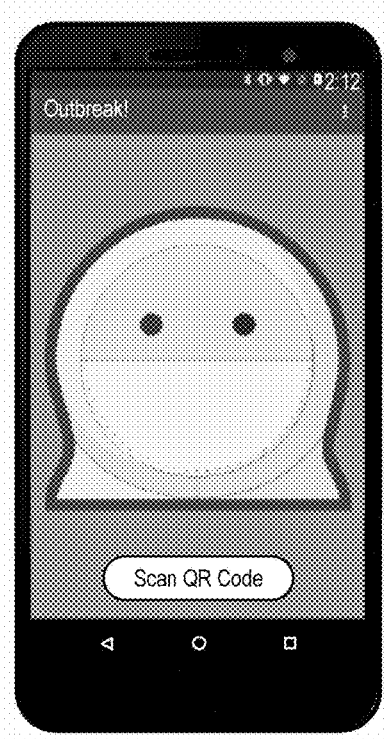
FIG. 25 displaying an icon associated with a facemask or other personal protective equipment, in accordance with certain examples of the technology disclosed herein.

FIG. 25 displaying an icon associated with a facemask or other personal protective equipment, in accordance with certain examples of the technology disclosed herein. For example, this screen may inform the user that the character is wearing appropriate protective equipment.

Figure 26:
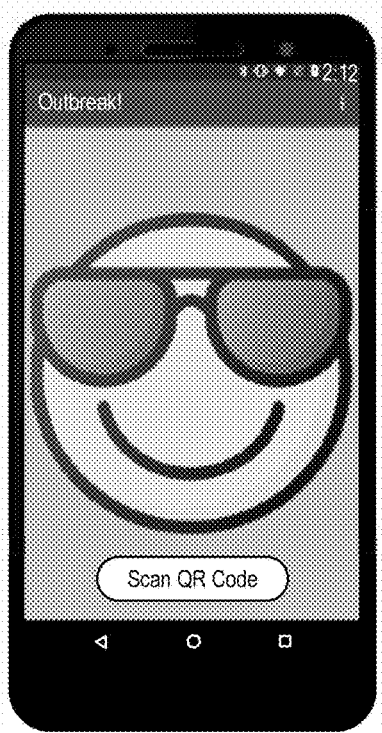
FIG. 26 displaying a health status of vaccinated, in accordance with certain examples of the technology disclosed herein.

FIG. 26 displaying a health status of vaccinated, in accordance with certain examples of the technology disclosed herein.

Figure 27:
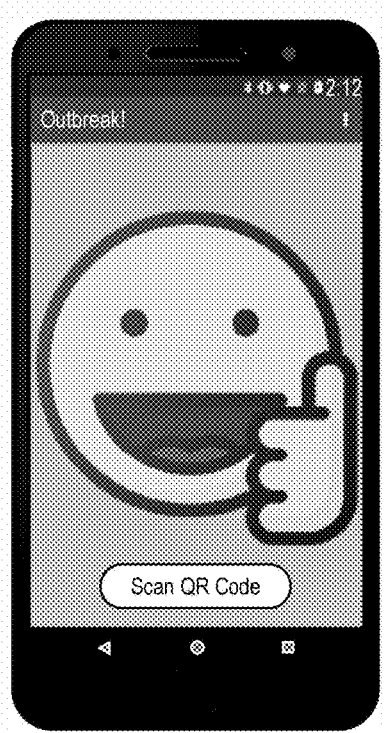
FIG. 27 displaying a health status of recovered from an infection, in accordance with certain examples of the technology disclosed herein.

FIG. 27 displaying a health status of recovered from an infection, in accordance with certain examples of the technology disclosed herein.

Other Examples

FIG. 9 depicts a computing machine 2000 and a module 2050 in accordance with certain examples. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a router or other network node, a vehicular information system, one or more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain examples, the processor 2010 along with other components of the computing machine 2000 may be a virtualized computing machine executing within one or more other computing machines.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 may also include volatile memories such as random-access memory ("RAM"), static random-access memory ("SRAM"), dynamic random-access memory ("DRAM"), and synchronous dynamic random-access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for coupling in operation the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks (WAN), local area networks (LAN), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to certain examples, any of the processor 2010, the other elements of the computing machine 2000, or the various peripherals discussed herein may be integrated into a single device such as a system on chip ("SOC"), system on package ("SOP"), or ASIC device.

Examples may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing examples in computer programming, and the examples should not be construed as limited to any one set of computer program instructions. Further, a skilled programmer would be able to write such a computer program to implement an example of the disclosed examples based on the appended flow charts and associated description in the application text. Therefore, disclosure of a particular set of program code instructions is not considered necessary for an adequate understanding of how to make and use examples. Further, those ordinarily skilled in the art will appreciate that one or more aspects of examples described herein may be performed by hardware, software, or a combination thereof, as may be embodied in one or more computing systems. Moreover, any reference to an act being performed by a computer should not be construed as being performed by a single computer as more than one computer may perform the act.

The examples described herein can be used with computer hardware and software that perform the methods and processing functions described herein. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

The example systems, methods, and acts described in the examples presented previously are illustrative, and, in alternative examples, certain acts can be performed in a different order, in parallel with one another, omitted entirely, and/or combined between different examples, and/or certain additional acts can be performed, without departing from the scope and spirit of various examples. Accordingly, such alternative examples are included in the scope of the following claims, which are to be accorded the broadest interpretation to encompass such alternate examples.

Although specific examples have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the examples, in addition to those described above, can be made by a person of ordinary skill in the art, having the benefit of the present disclosure, without departing from the spirit and scope of examples defined in the following claims, the scope of which is to be accorded the broadest interpretation so as to encompass such modifications and equivalent structures.

The invention is further described in the following examples, which do not limit the scope of the invention described in the claims.

EXAMPLES

Example 1—Aggregation of Real-Time Data to Determine Individual Susceptibility of Invention The COVID-19 Pandemic [1, 2] has emerged as the most serious health crisis that humanity has faced since the 1918 Influenza Pandemic [3]. Its causal pathogen, SARS-CoV-2 [4], is a coronavirus new to the human population with unique molecular [5], pathophysiological [6], and epidemiological [7] features. This has resulted in the exponential spread of COVID-19 around the world, with over 10 million confirmed cases and over 500,000 deaths worldwide by the time of this writing [8].

As part of the public interventions that aim to reduce the transmission of COVID-19, precautionary self-isolation of the general population and quarantining of suspected and confirmed mild cases is a strategy that can substantially reduce the effective reproductive number of the disease, $R_0$ [9]. This has the important consequence of 'flattening the epidemic curve' until herd immunity is achieved, either by post-infection immunity or vaccination, and therefore avoid overwhelming the healthcare system [10]. Active monitoring of contacts via traditional contact tracing by healthcare workers [11], potentially complemented and expanded with proximity-sensing tracking mobile apps [12], could further help mitigate transmission [13].

Applicant adopted an individual-level model (ILM) framework that enables expression of the probability of a susceptible individual being infected as a function of their interactions with the surrounding infectious population while also allowing to incorporate the effect of individually-varying risk factors (e.g., age, pre-existing conditions, or other suitable factors). ILMs are intuitive and flexible due to be expressed in terms of individual interactions [14-16] but also computationally costly to parameterize, especially in the case of epidemics in large populations. More recent work has shown how to simplify the probabilistic calculations to make ILMs more readily applicable in real-life scenarios [17]. The addition of geographical covariates could, in flexible infectious disease models, be used for formulating etiological hypotheses and identifying geographical regions of unusually high risk to formulate preventive action [18]. Therefore, ILMs can provide for better understanding of the spatio-temporal dynamics of disease spread facilitating a greater understanding of the impact of policies and interventions for controlling epidemic outbreaks.

Applicant first applied the formalism for ILMs to derive an expression for the marginal probability of individual risk of infection as a function of parameters with straightforward epidemiological interpretation and initial estimation. Applicant incorporated symptom and other individual-level data to update the risk of infection based on this new information. Applicant then constructed a population-level compartmental SIR epidemic model, where the rate of infection can be estimated from the individual-level probabilities given a random sample of individuals from the population. This allows to express the population-level parameters as a function of the individual-level parameters, and to use partially observed data (overall case counts, and individual risk factors and contacts) to apply Maximum Likelihood Estimate (MLE) within a Partially Observed Markov Process (POMP) framework. The POMP framework enables solving a computationally more tractable MLE problem due to iterated filtering, an efficient computational method based on a sequence of filtering operations which are shown to converge to a maximum likelihood parameter estimate. As a result of this approach, Applicant derived estimates of individual-level parameters that can be used to predict risk of infection.

Model Formalism
Individual-Level Models

In this section, the general form of the epidemic ILM is presented based on [17] where the heterogeneity of infectious disease transmissions are allowed at the individual-level. Individuals who are susceptible, infectious, or removed at time t are denoted as $S(t)$, $I(t)$, or $R(t)$ respectively. Note, for given t, $S(t)$, $I(t)$, and $R(t)$ are mutually exclusive. Here, Applicants assume time is discretized so that time point t, for t=1, 2, ..., represents a continuous time interval [t, t+1).

Let $P(i, t)$ be the probability of a susceptible$^\infty$ individual i being infected at time t. Then a general form of the ILM, without geography dependency, is given as:

$$P(i, t) = 1 - \exp\left[\left(-\Omega_S(i) \sum_{j \in C(i,t)} \Omega_T(j) \kappa(i, j, t)\right) - \epsilon(i, t)\right] \quad (1)$$

where $C(i, t)$ is the set of infectious individuals that interacted with i in the time interval [t, t+1). The functions $\Omega_S(i)$ and $\Omega_T(j)$ represent risk factors associated with susceptible individual i contracting, and infectious individual j passing on, the disease, respectively. Risk factors that involve both the infected and susceptible individuals, such as spatial separation or contact networks, are incorporated through the (time-dependent) infection kernel, $\kappa(i, j, t)$. Finally, the sparks term, $s(i, t)$, represents infections that are not well explained by the $\Omega_S(i)$, $\Omega_T(i)$, and $\kappa(i, j)$ terms (e.g., infections originating from outside the study population). For example, $s(i, t)=s$ could be used to represent purely random infections that occur with equal probability throughout the susceptible population at any given time.

This formula is the result of assuming a Poisson infectious process in each time interval [t, t+1). Applicants count the number k of transmission events between susceptible i and infected j, which follow a Poisson distribution $$f(k) = \frac{e^{-\lambda}\lambda^k}{k!}$$

with $\lambda$ the rate of transmission. Non-infection from j corresponds to k=0, so then $f(k=0)=e^{-\lambda}$. The rate of transmission from j to i is modeled as the product form $\lambda_{i,j}=\Omega_S(i)\Omega_T(j)\kappa(i,j)$. Non-infection of i from all infected j follows from independence between these Poisson processes, therefore (ignoring the sparks term):

$$1 - P(i, t) = \prod_j e^{-\lambda_{i,j}}$$

Formally, the ILMs can be extended to incorporate the effect of spatially varying risk factors upon the transmission of infectious disease. The resulting GD-ILMs have the general form [18]:

$$P(i, k, t) = 1 - \exp\left[\left(-\Omega_S(i, k) \sum_{j \in C(i,t)} \Omega_T(j, k) \kappa(i, j, t)\right) - \epsilon(i, k, t)\right] \quad (2)$$

where k represents the area index which varies from 1 to K. Here, $\Omega_S(i, k)$ is a susceptibility function of potential risk factors associated with susceptible individual i in area k contracting the disease; $\Omega_T(j, k)$ is a transmissibility function of potential risk factors associated with infectious individual j in area k passing on the disease; $\kappa(i, j, t)$ is the infection kernel that represents risk factors associated with both susceptible i and infectious j individuals at time t (assumed to be independent of area k); and the sparks term, $s(i, k, t)$, represents "random" infections that are not otherwise explained by the model. However, in the context of this manuscript Applicants will only consider simple ILM without explicit geographical dependencies.

Model Covariates

The aforementioned susceptibility and transmissibility functions, $\Omega_S(i)$ and $\Omega_T(j)$, respectively, can be used to model individual-level covariates. Applicants may wish to identify the vulnerable age groups and gender along with the estimation of vaccination effect in the susceptibility function. Applicants propose a general susceptibility function as follows:

$$\Omega_S(i) = a_0 + a_1 X_1(i) + \ldots + a_N X_N(i) \quad (3)$$

where $a_0 > 0$ is a constant susceptibility parameter, and $X_n(i)$ are covariates that represent various susceptibility factors to be included in the model (e.g.: age, pre-existing conditions, etc.) Thus, $a_n$ is the parameter for the n-th individual-level covariate.

The transmissibility function has a similar general form:

$$\kappa(i,j,t) = F(\{d_{i,j}(\tau), \tau \in [t, t+1)\}) \quad (5)$$

The next sections will provide specific details on these factors and concrete assumptions motivated by what is known about COVID-19.

Model Simplifications

The general forms of the $\Omega_S(i)$ and $\Omega_T(i)$ functions described above allow us to incorporate an arbitrary number of covariates into the model. Here Applicants propose a very simple initial model. The susceptibility function will depend only on "immunity status" of the susceptible individual. Applicants define the variable $X_1(i)$ to be 1 if individual i is over 65 or is immunosuppressed due to some pre-existing condition, 0 otherwise. Therefore:

$$\Omega_S(i) = a_0 + a_1 X_1(i) \qquad (6)$$

For the transmissibility function, an important factor determining the potential for an infected individual to pass along the virus seems to be the presence or absence of symptoms. So in this case the binary covariate $Y_1(j)$ takes the values 0 or 1 whether the infected individual is asymptomatic/pre-symptomatic or symptomatic, respectively. So Applicants arrive to the following simplified form:

$$\Omega_T(j) = b_0 + b_1 Y_1(j) \qquad (7)$$

As for the the infection kernel, for the time being is just 1 when j is in C(i, t), the contact set of i, which includes all the infectious individuals whom i was closer than 2 meters for at least 15 minutes in [t, t+1), and 0 otherwise:

$$\kappa(i, j) = \begin{cases} 1 & j \in C(i, t) \\ 0 & \text{otherwise} \end{cases} \qquad (8)$$

Finally, a zero sparks term was adopted. This assumption is reasonable is transmission mainly due to interactions between individuals, and not through the environment (e.g.: contaminated surfaces or fomites). There is some anecdotal evidence that this might be the case in COVID-19 [12], but for the time being assuming s(i, t)=0 to keep the models simple.

With these modeling decisions the following expression for the individual probability of infection was reached:

$$P(i, t) = 1 - \exp\left(-[a_0 + a_1 X_1(i)] \sum_{j \in C(i,t)} [b_0 + b_1 Y_1(j)]\right) \qquad (9)$$

Conditioning on Additional Data

Formula (9) gives an expression of the marginal probability P (i, t) of infection of individual i in time interval [t, t+1). This probability depends on a number of individual-level and area-level covariates. However, additional data from the l-individual i can be used to arrive to an updated risk of infection. In particular, Applicants are interested in the probability of infection over the course of the past d days given this new data, $P(I_{[t-d,t]}|D)$, with d defining an appropriate retrospective window of possible infection. Given that the incubation period of COVID-19 is two weeks, then d=14 should be a suitable choice to inform quarantining/testing measures. Applying Bayes Theorem to this probability, Applicants can formally write:

$$P(I_{[t-d,t]}|D) = \frac{P(D|I_{[t-d,t]})P(I_{[t-d,t]})}{P(D)}$$

The probability of an infection over the course of the past d days can be expressed as a function of the per-day probabilities of infection:

$$P(I_{[t-d,t]}) = P(I_{t-d}) + P(I_{t-d+1}) + \ldots + P(I_t)$$

since each event (infection d days ago, _d 1 days ago, and so on) is independent from each other. Furthermore, infection n day ago implies that infection did not happen until exactly that day, and so:

$$P(I_{t-n}) = \prod_{l=0}^{d-n-1} [1 - P(t - d + l)] P(t - n)$$

where P (t') is precisely (9), with indices for individual i omitted for clarity. More concretely, if D comprises symptom data self-reported by individual i, or $S_i$, Applicants can then write the risk of infection over the past d days for individual i at time t given symptom data $S_i$:

$$R(i, t) = r_s \sum_{n=0}^{d} \prod_{l=0}^{d-n-1} [1 - P(i, t - d + l)] P(i, t - n) \qquad (10)$$

with the coefficient r, defined as:

$$r_s = \frac{P(S_i | I_{[t-d,t]})}{P(S_i)} \qquad (11)$$

This coefficient can be thought of the ratio of the observed symptoms given the fact that the individual was recently infected to the prevalence of those symptoms among the general population, which in general should be greater than 1. For instance, if the observed symptoms are cough and fever, then $r_s$ is a measure of how prevalent those symptoms are among people infected with COVID-19, and could be estimated from currently available data. In fact, a recent study [19] looked at the predictive power of symptoms self-reported in the US and UK with the COVID Symptom Study mobile app [20]. This study presents a logistic regression predictor of infection given a number of system predictors:

P(I|S)=1.32−0.01×age+0.44×sex+1.75×smell and taste loss+0.31×cough+0.49×fatigue+0.39× skipped meals (12)

I Applicants make the assumption that, for a sufficiently long period of time d, the conditional probability $P(S|I_{[t-d,t]})$ is simply P (S I), where I represents infection at some moment in the past. With this assumption in place, Applicants can connect the COVID Symptom Study prediction model without probabilistic formalist by means of:

$$\frac{P(S|I)}{P(S)} = \frac{P(I|S)}{P(I)} = r_s \qquad (13)$$

where P (I) would represent the overall prevalence of COVID-19 infection. This allows us to write the following final formula for the risk score:

$$R(i, t) = \frac{P(I|S_i)}{P(I)} \sum_{n=0}^{d} \prod_{l=0}^{n-1} [1 - P(i, t - d + l)] P(i, t - d + n) \qquad (14)$$

Given knowledge of the individual's symptoms, demographic and medical covariates, and their recent contact history, it would be then possible to calculate this risk of infection.

Maximum Likelihood in POMPS

Following [17], given the S(t), E(t), I(t), and R(t) counts of susceptible, exposed, infected, and recovered individuals, respectively, at time t, Applicants can write the likelihood function as function of the parameter vector $\theta=(a_0, a_1, b_0, b_1)$ as the individual probabilities of infection as follows:

$$\mathcal{L}(\theta|S,\mathcal{E},\mathcal{I},\mathcal{R})=P(S,\mathcal{E},\mathcal{I},\mathcal{R}|\theta)=\Pi f_t(S(t),E(t),I(t),R(t)|\theta) \quad (15)$$

where $S=\{S(t)\}_t$, $\mathcal{E}=\{E(t)\}_t$, $\mathcal{I}=\{I(t)\}_t$, $\mathcal{R}=\{R(t)\}_t$, and the joint probability of all new infections occurring in time interval [t, t+1]:

$$f_t(S(t), E(t), I(t), R(t) | \theta) = \left[\prod_{i \in E(t+1)-E(t)} P(i, t)\right]\left[\prod_{i \leq s(t+1)} (1 - P(i, t))\right] \quad (16)$$

MLE via Metropolis-Hastings MCMC requires L|S E I R the recalculation of (θ . . . ) a very large number of times, with varying θ, in order to maximize the likelihood. In each recalculation of the likelihood, the products over all the individuals i have to be evaluated, which can become prohibitive even for relatively small populations.

An alternative MLE approach integrates compartmental models with Partially Observed Markov Process (POMP) models [21]. Compartmental models simplify the mathematical modeling of infectious disease; however, they assume access to fully observed disease data. In reality, not all COVID-19 cases are reported, and there are several reports of infectious asymptomatic/pre-symptomatic carriers [22], with some studies [23] suggesting at least 30% of asymptomatic cases. POMP models allow us to address such limitations by combining the simplicity of compartmental models with a probabilistic framework for the unobserved data. POMP models represent data $\geq y_1^*, \ldots, y_N^*$ collected at times $t_1 < \ldots < t_N$ as noisy, incomplete observations of an unobserved Markov process X(t), t $t_0$. Disease transmission, represented by compartmental models, is a Markov process because the number of infectious people at time t is solely determined by the number of infectious people at time t δ. A POMP model is characterized by the transition density and measurement density of its stochastic processes. The one-step transition density is represented by $f_{X_n x_n|}(x_n\ x_{n\ 1}; \theta)$, since X(t) is Markovian and only relies on the previous state. Meanwhile, the measurement density depends on only the state of the Markov process at that time and so is represented by $f_{Y_n|X_n}(y_n\ x_n; \theta)$, where $Y_n$ is a random variable modeling the observation at time $t_n$. Hence, the entire joint density for a POMP model, including the initial density $f_{X_0}(x_0; \theta)$, is:

$$f_{X_{0:N} Y_{1:N}}(x_{0:N}, y_{1:N}; \theta) = f_{X_0}(x_0; \theta) \prod_{n=1}^{N} f_{X_n|X_{n-1}}(x_n | x_{n-1}; \theta) f_{Y_n|X_n}(y_n | x_n; \theta)$$

and the marginal density for the sequence of measurements, $Y_{1:N}$, evaluated at the data, $y^*_{1:N}$, is $$f_{Y_{1:N}}(y(1:N)^*;\theta)=\int f_{X_{0:N} Y_{1:N}}(x_{0:N}, y_{1:N};\theta)dx_{0:N}$$

Here the state variable $X_1$ is the vector (S(t), E(t), I(r), R(t)) described before. Our novel approach here will be to relate the population-level parameters in a SEIR model for COVID-19 [9] with average estimations calculated over a suitable sample of individuals, which will be expressed in terms of the individual-level probabilities defined by equation (9) and, ultimately, as a function of the individual-level parameters $\Theta=(a_0, a_1, b_0, b_1, s)$. In this way, our method can be seen a form of hierarchical maximum likelihood where estimation of individual-level is performed simultaneously with the population-level parameters [24], which has the advantage of reducing variability in the recovered parameters [25].

SEIR Model Setup

Applicants constructed the two components of a POMP model: the unobserved process model and the measurement model. The process model, defined as a SEIR model, provides the change in true incidence of COVID at every time point, while the measurement model incorporates the fact that not all cases are observed or reported.

The underlying dynamics of COVID can be captured by a stochastic SEIR model. Most of the assumptions of a basic SEIR model are still the same in a stochastic version. However, Applicants add parameters that induce random fluctuations into the population and change the compartments' rates of transfer in response to interventions. Applicants do this by using probabilistic densities for the transition of state variables. Moreover, although disease dynamics are technically a continuous Markov process, this is computationally complex and inefficient to model, and so Applicants make discretized approximations by updating the state variables after a time step, δ. The system of discretized equations is shown below, where B(t) is the number of susceptible individuals who become exposed to COVID, C(t) is the number of newly infectious cases, and D(t) is the number of cases that are removed from the population, all during the time step δ:

$$S(t+\delta)=S(t)-B(t)$$

$$E(t+\delta)=E(t)+B(t)-C(t)$$

$$I(t+\delta)=I(t)+C(t)-D(t)$$

$$R(t+\delta)=R(t)+D(t)$$

$$S(t)+E(t)+I(t)+R(t)=N \quad (17)$$

This equation describes how the sizes of the four compartments (susceptible, exposed, infectious, and removed) change between (t, t+δ). The model further assumes that the population size N remains constant at every time point. Applicants added inherent randomness to our model by setting B(t), C(t), and D(t) as binomials. If Applicants assume that the length of time an individual spends in a compartment is exponentially distributed with some compartment-specific rate x(t), then the probability of remaining in that compartment for an additional day is exp(−x(t)) and the probability of leaving that compartment is 1−exp(−x(t)):

$$B(t)\sim\text{Binomial}(S(t),1-\exp(-\lambda(t)))$$

$$C(t)\sim\text{Binomial}(E(t),1-\exp(-\sigma))$$

$$D(t)\sim\text{Binomial}(I(t),1-\exp(-\gamma)) \quad (18)$$

The force of N infection, λ(t), is the transition rate between the susceptible and exposed classes and can be written as $\lambda(t)=\beta(t)\frac{I(t)}{N}$, where β(t) represents the transmission rate of the disease. Furthermore, σ is the transition rate between the exposed and infectious classes, and γ is the transition rate between the infectious and removed compartments. $\sigma^{-1}$ represents the mean length of time a person stays in the latent stage and $\gamma^{-1}$ represents the mean length of time a person is infectious before being removed from the population (either because of intervention efforts or natural recovery). Applicants assume these two parameters to be constant over the course of the epidemic.

The transmission rate $\beta(t)$ can be estimated from sample averages calculated over individuals. If Applicants recall the ILM formalism from the previous section, Applicants can write the probability of infection of susceptible i by infected contact j as follows:

$$p_{i,j} = 1 - \exp(-[a_0 + a_1 X_i][b_0 + b_1 Y_j]) \tag{19}$$

Therefore, the transmission rate for individual j is the sum of theses probabilities over all the contacts:

$$\beta_j = \sum_{i \in C(j)} 1 - \exp(-[a_0 + a_1 X_1(i)][b_0 + b_1 Y_1(j)]) \tag{20}$$

If Applicants are considering infected individuals from a random sample J Applicants can then estimate the transmission rate as:

$$\hat{\beta} = \frac{1}{|J|} \sum_{j \in J} \sum_{i \in C(j)} 1 - \exp(-[a_0 + a_1 X_1(i)][b_0 + b_1 Y_1(j)]) \tag{21}$$

Given a fixed sample J, Applicants can consider $\hat{\beta} = \hat{\beta}(a_0, a_1, b_0, b_1)$, that is, a function solely of the individual-level susceptibility and transmissibility coefficients. Although it is impossible to directly record the number of people that are susceptible, exposed, infectious, and removed directly, the publicly available data tells us the number of observed cases per day. The mean number of observed cases per day is the true number of cases multiplied by the reporting rate $\rho$ ($\rho < 1$). This can be modeled with a binomial distribution of parameters C(t) and $\rho$:

$$y_t | C(t) \sim \text{Binomial}(C(t), \rho) \tag{22}$$

The process and measurement models define our final POMP model. For each time point, the process model generates the number of new cases based on binomial distributed counts. The measurement model then estimates the observed number of cases based on the true number of cases and reporting rate.

Iterated Filtering Method

The likelihood function for the POMP models is the density function evaluated with data at a candidate set of parameter values. It is computationally simpler to work with the log likelihood, $l(\theta) = \log f(y_{1:N}; \theta)$, so that Applicants can deal with sums instead of products. Applicants used a simulation-based approach to avoid solving the density function analytically, in which Applicants simulated the random variable $Y_{1:N}$, which implicitly defines the density function. Likelihood evaluation via Sequential Monte Carlo (SMC) techniques is one standard method to obtain the log likelihood for POMP models, because it simulates sample paths rather than requiring explicit transition probabilities. Exploiting the Markov property of the process, it is possible to use these paths to sample the parameter space much more efficiently than with regular MCMC, thanks to the iterated filtering method.

Applicants factorized the likelihood as the product of conditional likelihoods:

$$L(\theta) = \prod_{n=1}^{N} L_{n|1:n-1}(\theta) \tag{23}$$

where $L_{m|1:n-1}(\theta) = P[y_n^*{}_{:n-1}; \theta]$ and there are N time points. The structure of a POMP model then implies the representation of $L_{m|1:n-1}(\theta)$ as $$L_{n|1:n-1}(\theta) = \int P[y_n^*|x_n;\theta]P[x_n|y_{1:n-1}^*;\theta]dx_n \tag{24}$$

so that the final expression for the likelihood is:

$$\prod_{n=1}^{N} \int P[y_N^* | x_n; \theta] P[x_n | y_{1:n-1}^*; \theta] dx_n \tag{25}$$

In this last equation, although $P[y_n^* x_n^*; \theta]$ is simple to calculate (using the observation process), $P[x_n y_{1\ n\ 1}^*; \theta]$ is more difficult to evaluate. Applicants can use the Markov property to determine an expression for this probability, known as the prediction formula:

$$P[x_n|y^*_{1:n-1};\theta] = \int P[x_n|x_{n-1};\theta]P[x_{n-1}|y^*_{1:n-1};\theta]dx_{n-1} \tag{26}$$

Applicants can then use Bayes' Theorem to determine an expression for P $[x_{n-1}|y1^*:n-1; \theta]$, known as the filtering formula:

$$P[x_n | y^*_{1:n}; \theta] = P[x_n | y_n^*, y^*_{1:n-1}; \theta] = \frac{P[y_n^* | x_n; \theta] P[x_n | y^*_{1:n-1}; \theta]}{\int P[y_n^* | x_n; \theta] P[x_n | y^*_{1:n-1}; \theta] dx_n} \tag{27}$$

The prediction and filtering formulas give us a recursion. Specifically, the prediction formula calculates the pre-diction distribution at time $t_n$, $f(X_{n\ 1} Y_{1:n\ 1}(x_{n\ 1} y_1^*{}_{:n\ 1})$, at time $t_n$ by using the filtering distribution at time $t_{n-1}$, $f(X_{n\ 1} Y_{1:n\ 1})(x_{n\ 1} y_1^*{}_{:n\ 1})$, at time $t_{n\ 1}$. Meanwhile, the filtering formula gives us the filtering distribution at time $t_n$ using the prediction distribution at time $t_n$.

In SMC, Applicants use Monte Carlo techniques to sequentially estimate the integrals in the prediction and filtering recursions, which in turn allows us to estimate P $[x_n y_1^*{}_{:n\ 1}; \theta]$. This is done by generating a swarm of J particles that are propagated forward based on the process model and then filtered and altered to fit the next data point more closely. Because of this, SMC is commonly known as the particle filter.

Iterated filtering [26] allows to more efficiently obtain MLEs of parameters in partially observed dynamical systems, such as POMPs. It works by defining a set of initial values for the parameter vector $\theta$ and a fixed number of iterations, M. For every iteration, Applicants apply a basic particle filter (Equation 9 above) to the model and add stochastic perturbations to the parameters so that they take a random walk through time. At the end of the time series, Applicants use the final value of the parameters as the starting point for the next iteration but reducing ("cooling") the random walk variance. After completing the M iterations, Applicants obtain the Monte Carlo maximum likelihood estimate, $\theta_M$, and its corresponding log likelihood. In contrast, Monte Carlo likelihood by direct simulation scales poorly with dimension. It requires a Monte Carlo effort that scales exponentially with the length of the time series, and so is infeasible on anything but a short data set.

Simulation Study

Parameter Estimation

Millions of individuals worldwide have self-reported symptoms associated with COVID-19 infection through numerous websites and apps specifically designed for that purpose [19]. Meanwhile, anonymized mobility data generated by cellphones has been aggregated from several sources and made available for research [27]. However, this currently available data is not enough to evaluate the ILMs described above. These models can potentially provide infection risk predictions aggregating several sources of health and epidemiological data from individuals, including symptoms, demographics, and contact information. Approaches incorporating this kind of data, collected through contact tracing and symptom reporting apps, have been proposed recently by several groups [28, 29], and have led to consider the privacy risks presented by this data and possible mitigation of those risks. Here, Applicants are focusing primarily on the parameter estimation problem, assuming that it is possible to acquire the data securely, but will make some observations regarding privacy in the conclusions.

Since the detailed data needed to calculate our ILMs is not currently available, Applicants have started by conducting a purely computational study where the individual-level data is generated by means of agent-based models (ABMs). These models allow us to simulate behaviours of individuals in a large population, and obtain data that mirrors what Applicants could collect with contact tracing and symptom reporting apps in real life. One advantage of using ABMs at this stage is that Applicants can define the ground truth of the ILM by specifying the coefficients in the susceptibility and transmissibility functions, this allow us to evaluate the accuracy of our parameter estimation methods.

For the purpose of running the ABMs simulations, Applicants used the COMOKIT COVID-19 SEIR model [30] implemented in the GAMA software [31], a general ABM simulator allowing for a wide range of options through a custom modeling language and supporting GIS layers to represent specific geographical in detail. In particular, Applicants run simulations using a scenario of a COVID-19 outbreak in Vietnam without any containment strategies, with a population of nearly 10,000 individuals. Applicants adapted the SEIR model provided in COMOKIT to incorporate the individual probabilities of infection as defined by Formula (9), with a number of different selections of parameters $\theta = (a_0, a_1, b_0, b_1)$.

TABLE 1

Maximum likelihood estimates for all the parameter sets

| | True value | MLE mean | MLE sdev |
|---|---|---|---|
| Set 1 | | | |
| $c_{00}$ | 0.04 | 0.063 | 0.036 |
| $c_{01}$ | 0.40 | 0.839 | 0.411 |
| $c_{10}$ | 0.40 | 0.603 | 0.346 |
| $c_{11}$ | 4.00 | 5.452 | 1.825 |
| Set 2 | | | |
| $c_{00}$ | 0.25 | 0.629 | 0.216 |
| $c_{01}$ | 0.40 | 0.347 | 0.384 |
| $c_{10}$ | 0.75 | 1.690 | 0.538 |
| $c_{11}$ | 1.20 | 1.438 | 0.667 |

TABLE 1-continued

Maximum likelihood estimates for all the parameter sets

| | True value | MLE mean | MLE sdev |
|---|---|---|---|
| Set 3 | | | |
| $c_{00}$ | 1.0 | 0.381 | 0.120 |
| $c_{01}$ | 1.0 | 1.409 | 0.322 |
| $c_{10}$ | 2.0 | 2.088 | 0.901 |
| $c_{11}$ | 2.0 | 2.113 | 1.218 |

Applicants arbitrarily defined three sets of ground truth parameters, $\theta_1 = (a_0 = 0.2, a_1 = 2.0, b_0 = 0.2, b_1 = 2.0)$, $\theta_2 = (a_0 = 0.5, a_1 = 1.5, b_0 = 0.5, b_1 = 0.8)$, and $\theta_3 = (a_0 = 1.0, a_1 = 2.0, b_0 = 1.0, b_1 = 1.0)$. Given the symmetric form of (9), Applicants expanded the product of the transmissibility and susceptibility functions to arrive to the following reparametrization:

$$\hat{\beta} = \frac{1}{|J|} \sum_{j \in J} \sum_{i \in C(j)} 1 - \exp(-[c_{00} + c_{01} Y_1(j) + c_{10} X_1(i) + c_{11} X_1(i) Y_1(j)]) \quad (28)$$

The relationship between the original and new parameters is given by:

$$a_0 b_0 = c_{00}$$

$$a_0 b_1 = c_{01}$$

$$a_1 b_0 = c_{10}$$

$$a_1 b_1 = c_{11} \quad (29)$$

from which Applicants can express the ratios $a_0/a_1$ and $b_0/b_1$ as a function of the new parameters $c_{00}$, $c_{01}$, $c_{10}$, and $c_{11}$:

$$\frac{a_0}{a_1} = \frac{c_{01}}{c_{11}} = \frac{c_{00}}{c_{10}} \quad (30)$$

$$\frac{b_0}{b_1} = \frac{c_{00}}{c_{01}} = \frac{c_{10}}{c_{11}}$$

Applicants assume the mean latent and infectious times to be known, and Applicants can estimate them from the GAMA data. In the case of the COMOKIT simulations, have $\sigma = 0.26$ and $\gamma = 0.6$, both in units of 1/day. Therefore, the only parameters in the SEIR model at the population level are c00, c01, c10, and c11, which Applicants estimate by applying iterated filtering with POMP. An MLE run corresponding to the the underlying parameters $\theta_1$ is shown in FIG. 1.

An issue Applicants encountered with the first round of MLE runs is that, as the ABM simulation progressed, the compartment of susceptible individuals gets depleted as more become infected, and so the $\hat{\beta}$ estimator becomes increasingly biased. In order to account for this problem, Applicants fit the GAMA data only for the initial stages of the simulated epidemic, when the number of new infectious cases is still increasing due to the large percentage of susceptible individuals. The range of the data with enough susceptible is shown in FIG. 2.

The ground truth values for the $c_{00}$, $c_{01}$, $c_{10}$, and $c_{11}$ parameters, and the mean and standard deviation over the 10 highest likelihoods are listed in table 1. Most of the true values fall within a standard deviation from the mean MLE, as seen in 3, with the exception of $c_{00}$ in the parameter set 3.

TABLE 2

Approximation to the original parameter ratios using MLEs

|  | True ratio | MLE approx. |
|---|---|---|
| Set 1 | | |
| $a_0/a_1$ | 0.10 | 0.13 |
| $b_0/b_1$ | 0.10 | 0.09 |
| Set 2 | | |
| $a_0/a_1$ | 0.33 | 0.31 |
| $b_0/b_1$ | 0.62 | 1.50 |
| Set 3 | | |
| $a_0/a_1$ | 0.5 | 0.42 |
| $b_0/b_1$ | 1.0 | 0.63 |

TABLE 3

Mean and standard deviation of individual risks for susceptible ($R_s$) and infected individuals ($R_I$)

|  | $R_S$ | $R_I$ |
|---|---|---|
| Set 1 | 0.24 ± 0.25 | 0.52 ± 0.34 |
| Set 2 | 0.28 ± 0.24 | 0.45 ± 0.32 |
| Set 3 | 0.55 ± 0.31 | 0.63 ± 0.31 |

In order to recover the original parameters $a_0$, $a_1$, $b_0$, and $b_1$ that are needed in the susceptibility and transmissibility functions, Applicants can use the ratios in equation 30. An initial calculation simply taking the top estimates of the $c_{ij}$'s to calculate the mean and standard deviation of the a's and b's gave values with high errors when compared with the true ratios, which seems to be caused by fluctuations in the $c_{ij}$'s. A better approximation to the ratios is given by this heuristic formula:

$$\frac{a_0}{a_1} = 0.5\frac{\overline{MLE}(c_{01})}{\overline{MLE}(c_{11})} + 0.5\frac{\overline{MLE}(c_{00})}{\overline{MLE}(c_{10})} \qquad (31)$$

$$\frac{b_0}{b_1} = 0.5\frac{\overline{MLE}(c_{10})}{\overline{MLE}(c_{11})} + 0.5\frac{\overline{MLE}(c_{00})}{\overline{MLE}(c_{01})}$$

where $\overline{MLE}(c_{ij})$ represents the mean of the parameter $c_{ij}$ taken over the 10 top MLEs. This formula smooths out the fluctuations in the individual parameters, and gives a better result, shown in table 2.

Risk Calculation

Once the parameters of the model have been determined through MLE using POMP, in particular the individual-level parameters ($c_{00}$, $c_{01}$, $c_{10}$, $c_{11}$) Applicants can compute individual risks of infection using equation (14). Applicants use the ABM in GAMA with the three parameter sets and a random assignment of symptoms for susceptible and infected individuals using the symptom prevalence for the US listed in [19]. Instead of using the ground truth individual-level parameters, Applicants generate random perturbation of $a_0$ and $b_0$, and then obtained $a_1$ and $b_1$ with the ratio estimates in (31).

As a first sanity check, Applicants calculated the mean risk for susceptible and infected individuals over entire simulation parameter runs with each parameter set, and Applicants obtained the results shown in table 3. Difference between the risks for susceptible and infected is very small for parameter set 3, and the reason for this is that this set yields higher probabilities of infection across all individuals, resulting in more uniform risk score values. This is important to keep in mind, as a situation like this would result in a poor discrimination capacity of the risk prediction.

Applicants then run ABM simulations where the risk values where used to quarantine for 14 days those individuals with a risk higher than a given threshold. Applicants simulated two scenarios, in the first scenario, there was a delay of 4 days between the risk calculation and its use to determine quarantine, in order to model the fact that the infectious status of contacts is not determined instantaneously, but with a lag caused by the symptom onset time (and also by the delay in obtaining test results). In the second scenario, the risk was updated instantly with the information of the infected contacts, this represents an unrealistic situation where infectious status is known upon interaction but gives an upper bound for the performance of the intervention. The results from these simulations are shown in FIG. 4. The epidemic curves of new cases for the three scenarios (no quarantine, delayed quarantine, and instant quarantine) suggest that risk-based quarantine could help in lowering the peak of new cases and spread them over a longer period of time (e.g.: "flattening the curve"), with the most pronounced effect in the case of instantaneous availability of infection status, which is impossible in practice but providing a "maximum curve flattening". Conclusions Applicants constructed a statistical inference framework that enables us to obtain individual-level epidemic parameters by applying MLE to population-level case data. Applicants tested this framework using an agent-based model to generate epidemic data resolved at the individual level. As part of this framework, Applicants defined an individual-level epidemic risk model that depends on data such as demographics, medical condition, self-reported symptoms, and contact tracing information. These models could be trained on aggregate data provided by consenting users of a mobile app, for example, and then evaluated locally by the rest of the users. These models could incorporate additional data, such as spatial random effects. The initial simulation experiments are promising and suggest that is possible to: (1) obtain good estimates for the individual-level parameters by applying MLE on the population level data and (2) carry out interventions based on the individual-level risks, such as quarantine, that could help in lowering the peak of the epidemic, i.e.: "flattening the curve". However, this work is in its initial stages and has several limitations. First, the individual-level models Applicants considered so far are very simple, including only two somewhat artificial covariates (immune and symptomatic levels). Second, the data to train the models were obtained completely from simulated experiments; thus, Applicants need to extend to and validate using real data. Third, our risk calculation requires knowledge on confirmed cases in order to determine exposure events, which might not be readily available or accessible. Other approaches [28, 29] are based on estimating the probabilities of all possible states an individual can be in (susceptible, infected, recovered) based on the available information (symptoms, tests, contacts, etc.) and then having this information be shared across the individuals through a mobile app in order to update the probabilities as new information is obtained. Our approach has the advantage of being simpler but could also incorporate some of these ideas to lift the requirement of exact infectious states to be known to calculate the risk score. Applicants envision the computational framework presented in this work to be the basis for a system that could be used to estimate risks of infection for diseases other than COVID-19.

REFERENCES FOR THIS EXAMPLE

1. Velavan, T. P. & Meyer, C. G. The COVID-19 epidemic. *Tropical Medicine & International Health* 25, 278-280. eprint: onlinelibrary.wiley.com/doi/pdf/10.1111/tmi.13383. onlinelibrary. wiley.com/doi/abs/10.1111/tmi.13383 (2020).
2. Fauci, A. S., Lane, H. C. & Redfield, R. R. Covid-19—Navigating the Uncharted. *New England Journal of Medicine* 382, 1268-1269. eprint: doi.org/10.1056/NEJMe2002387. doi.org/10.1056/NEJMe2002387 (2020).
3. Viboud, C. & Lessler, J. The 1918 Influenza Pandemic: Looking Back, Looking Forward. *American Journal of Epidemiology* 187, 2493-2497. ISSN: 0002-9262. eprint: academic.oup.com/aje/article-pdf/187/12/2493/26927979/kwy207.pdf. doi.org/10.1093/aje/kwy207 (October 2018).
4. Lu, R. et al. Genomic characterisation and epidemiology of 2019 novel coronavirus: implications for virus origins and receptor binding. *The Lancet* 395, 565-574. doi.org/10.1016/S0140-6736(20)30251-8 (2020/04/05 2020).
5. Wrapp, D. et al. Cryo-EM structure of the 2019-nCoV spike in the prefusion conformation. *Science* 367, 1260-1263. ISSN: 0036-8075. eprint: science.sciencemag.org/content/367/6483/1260.full.pdf. science.sciencemag.org/content/367/6483/1260 (2020).
6. Zou, L. et al. SARS-CoV-2 Viral Load in Upper Respiratory Specimens of Infected Patients. *New England Journal of Medicine* 382, 1177-1179. eprint: doi.org/10.1056/NEJMc2001737. doi.org/10.1056/NEJMc2001737 (2020).
7. Liu, Y., Gayle, A. A., Wilder-Smith, A. & Rocklöv, J. The reproductive number of COVID-19 is higher compared to SARS coronavirus. *Journal of Travel Medicine* 27. taaa021. ISSN: 1195-1982. eprint: academic.oup.com/jtm/article-pdf/27/2/taaa021/32902430/taaa02 Lpdf. doi.org/10.1093/jtm/taaa021 (February 2020).
8. Dong, E., Du, H. & Gardner, L. An interactive web-based dashboard to track COVID-19 in real time. *The Lancet Infectious Diseases*. doi.org/10.1016/S1473-3099(20)30120-1 (2020/04/05 2020).
9. Wang, C. et al. Evolving Epidemiology and Impact of Non-pharmaceutical Interventions on the Outbreak of Coronavirus Disease 2019 in Wuhan. China. medRxiv. eprint: www.medrxiv.org/content/early/2020/03/06/2020.03.03.20030593.full.pdf. www.medrxiv.org/content/early/2020/03/06/2020.03.03.20030593 (2020).
10. Kissler, S. M., Tedijanto, C., Lipsitch, M. & Grad, Y. Social distancing strategies for curbing the COVID-19 epidemic. medRxiv. eprint: www.medrxiv.org/content/early/2020/03/24/2020.03.22.20041079.full.pdf. www.medrxiv.org/content/early/2020/03/24/2020.03.22.20041079 (2020).
11. Eames, K. T. D. & Keeling, M. J. Contact tracing and disease control. *Proceedings of the Royal Society of London. Series B: Biological Sciences* 270, 2565-2571. eprint: royalsoc ietypubl ishing.org/doi/pdf/10.1098/rspb.2003 0.2554. royalsocietypublishing.org/doi/abs/10.1098/rspb.2003.2554 (2003).
12. Ferretti, L. et al. Quantifying SARS-CoV-2 transmission suggests epidemic control with digital contact tracing. *Science*. ISSN: 0036-8075. eprint: science.sciencemag.org/content/early/2020/03/30/science.abb6936.full.pdf. science.sciencemag.org/content/early/2020/03/30/science.abb6936 (2020).
13. Peak, C. M. et al. Modeling the Comparative Impact of Individual Quarantine vs. Active Monitoring of Contacts for the Mitigation of COVID-19. *medRxiv*. eprint: www.medrxiv.org/content/early/2020/03/08/2020.03.05.20031088.full.pdf. www.medrxiv.org/content/early/2020/03/08/2020.03.05.20031088 (2020).
14. Gibson, G. J. Markov Chain Monte Carlo Methods for Fitting Spatiotemporal Stochastic Models in Plant Epidemiology. *Journal of the Royal Statistical Society: Series C (Applied Statistics)* 46, 215-233. eprint: rss.onlinelibrary.wiley.com/doi/pdf/10.1111/1467-9876.00061. rss.onlinelibrary.wiley.com/doi/abs/10.1111/1467-9876.00061 (1997).
15. Keeling, M. J. et al. Dynamics of the 2001 U K Foot and Mouth Epidemic: Stochastic Dispersal in a Heterogeneous Landscape. *Science* 294, 813-817. ISSN: 0036-8075. eprint: science.sciencemag.org/content/294/5543/813.full.pdf. science.sciencemag.org/content/294/5543/813 (2001).
16. Neal, P. J. & Roberts, G. O. Statistical inference and model selection for the 1861 Hagelloch measles epidemic. *Biostatistics* 5, 249-261. ISSN: 1465-4644. eprint: academic.oup.com/biostatistics/article-pdf/5/2/249/651176/050249.pdf. doi.org/10.1093/biostatistics/5.2.249 (April 2004).
17. Deardon, R. et al. Inference for Individual-level models of infectious diseases in large populations. *Statistica Sinica* 20, 239-261. pubmed.ncbi.nlm.nih.gov/26405426 (January 2010).
18. Mahsin, M. D., Deardon, R. & Brown, P. Geographically dependent individual-level models for infectious diseases transmission. *Biostatistics*. kxaa009. ISSN: 1465-4644. eprint: academic.oup.com/biostatistics/advance—article—pdf/doi/10.1093/biostatistics/kxaa009/32742504/kxaa009. pdf. https://doi.org/10.1093/biostatistics/kxaa009 (March 2020).
19. Menni, C. et al. Real-time tracking of self-reported symptoms to predict potential COVID-19. *Nature Medicine*. doi.org/10.1038/s41591-020-0916-2 (2020).
20. COVID Symptom Study website covid.joinzoe.com/.
21. King, A. A., Nguyen, D. & Ionides, E. L. Statistical Inference for Partially Observed Markov Processes via the R Package pomp. *Journal of Statistical Software* 69, 1-43 (2016).
22. Aguirre-Duarte, N. Can people with asymptomatic or pre-symptomatic COVID-19 infect others: a systematic review of primary data. *medRxiv*. eprint: www.medrxiv.org/content/early/2020/04/16/.2020.04.08.20054023.full.pdf. www.medrxiv.org/content/early/2020/04/16/2020.04.08.20054023 (2020).
23. Nishiura, H. et al. Estimation of the asymptomatic ratio of novel coronavirus infections (COVID-19). eng. *Int J Infect Dis*. ISSN: 1878-3511 (Electronic); 1201-9712 (Linking) (March 2020).
24. Rouder, J. N. & Lu, J. An introduction to Bayesian hierarchical models with an application in the theory of signal detection. eng. *Psychon Bull Rev* 12, 573-604. ISSN: 1069-9384 (Print); 1069-9384 (Linking) (August 2005).
25. Farrell, S. & Ludwig, C. J. H. Bayesian and maximum likelihood estimation of hierarchical response time models. *Psychonomic bulletin & review* 15, 1209-1217. pubmed.ncbi.nlm .nih.gov/19001592 (December 2008).

26. Ionides, E. L., Breto, C. & King, A. A. Inference for nonlinear dynamical systems. *Proceedings of the National Academy of Sciences* 103, 18438-18443. ISSN: 0027-8424. eprint: www.pnas.org/content/103/49/18438.full.pdf. www.pnas.org/content/103/49/18438 (2006).
27. COVID-19 Mobility Data Network www.covid19mobility.org/.
28. Probabilistic inference framework for estimating risk of infection from proximity tracking data github.com/sphinxteam/sir_inference/.
29. Alsdurf, H. et al. COVI White Paper. arXiv: 2005.08502 [cs.CR] (2020).
30. Drogoul, A. et al. Designing social simulation to (seriously) support decision-making: COMOKIT, an agent-based modeling toolkit to analyze and compare the impacts of public health interventions against COVID-19. rofasss.org/2020/04/27/comokit/(April 2020).
31. Taillandier, P. et al. Building, composing and experimenting complex spatial models with the GAMA platform. *GeoInformatica* 23, 299-322. doi.org/10.1007/s10707-018-00339-6 (2019).

Example 2—Modeling the Spread of Infectious Disease on College Campuses

College campuses in the United States are highly vulnerable to infectious diseases outbreaks, and there is a mounting need to develop strategies that best mitigate their size and duration, particularly as colleges consider reopening their campuses in the midst of the COVID-19 pandemic. Towards addressing this need, Applicants applied a stochastic transmission model to quantify the impact of university-level responses to past outbreaks on their campuses and used it to determine which control interventions are most effective. The model aims to simultaneously overcome three crucial issues: stochastic variation in small populations, missing or unobserved case data, and changes in disease transmission rates post-intervention. Applicants tested the model and assessed various interventions using data from the 2014 and 2016 mumps outbreaks at Ohio State University and Harvard University, respectively. Our results suggest that universities should design more aggressive diagnostic procedures and stricter isolation policies to decrease infectious disease incidence on campus. Our model can be applied to data from other outbreaks in college campuses and similar small-population settings.

The ongoing COVID-19 pandemic has forced school closures around the world (1), and universities in the United States are designing plans for safe reopening during the Fall 2020 academic term (2). This is a challenging task, as college campuses provide ideal breeding grounds for infectious disease. Students live in close quarters, pack into lecture halls, share food and drinks in the dining areas, and engage in intimate contact. Outbreaks in these settings can spread very quickly. Indeed, a meningitis outbreak took place at Princeton University in March 2014, eventually claiming the life of one student. The Centers for Disease Control and Prevention (CDC) reported the attack rate of the disease on Princeton's campus to be 134 per 100,000 students—1,400 times greater than the national average (3).

A recent string of outbreaks on college campuses involves mumps, once a common childhood viral disease. After introduction of the measles-mumps-rubella (MMR) vaccine in 1977 and the two-dose MMR vaccination program in 1989, the number of mumps cases in the US plummeted by 2005. But, despite a vaccinated population, there has been a recent resurgence of mumps, with a steep jump from 229 cases in 2012 to 5833 cases in 2016 (4). Although a typically mild disease in children, up to 10% of mumps infections acquired after puberty can cause severe complications, including orchitis, meningitis, and deafness. Furthermore, a majority of recent mumps cases have occurred in young adults who had received the recommended two MMR doses. This suggests that vaccine-derived immunity wanes over time, unlike natural immunity—protection acquired from contracting the disease—which is permanent. Lewnard and Grad estimate that 33.8% of young adults (ages 20 to 24) were susceptible to mumps in 1990, in contrast to the 52.8% susceptible in 2006, as vaccinations have replaced contraction as the source of immunity (5). The temporary immunity from vaccines strengthens the argument for strict containment as a critical line of defense amidst an outbreak. In the case of COVID-19, lack of a vaccine coupled with substantial asymptomatic and pre-symptomatic transmission (6) provide further support for such approaches.

The spread of mumps at Harvard University in 2016, and extensive public health measures and documentation, presents a rare opportunity to closely examine an outbreak on a college campus. Between Jan. 1 and Aug. 31, 2016, 210 confirmed mumps cases were identified in the Greater Boston area, with most detected at Harvard University. Mumps is a highly contagious disease with the potential to travel quickly and pervasively on a crowded college campus. Some of the most notable mumps outbreaks on college campuses occurred in Iowa (7), Indiana (8), and Ohio (9). But, whereas mumps spread rapidly at Ohio State University in 2014 and the University of Iowa in 2006 and 2016, Harvard employed a number of interventions that may have helped mitigate spread of the disease and contain it over just a few months (10).

The successful containment at Harvard motivates us to explore varied intervention strategies, given the relative costs of prevention. Even if the use of a booster MMR vaccination is proven theoretically to reduce infection and thus potentially prevent outbreaks (5, 7), it is unlikely that universities with limited resources will proactively invest in a third dose. A rough cost analysis conducted by Harvard University Health Services (HUHS) showed that, while the total mumps care expenses for Harvard was approximately $75,000, the cost of providing a third MMR dose to every member of the Harvard community (at $83 per vaccination) was $1.7 million (11). Therefore, at least in the short term, a third MMR dose cannot be the only answer to handling mumps outbreaks; Applicants must consider more immediate solutions and interventions.

In order to understand the effectiveness of interventions aimed at containing an outbreak on a college campus, Applicants constructed a epidemiological model to simulate the dynamics of mumps on such a population and quantify the impact of various interventions. Most epidemiological models have at least one of three flaws: they cannot handle random fluctuations in a small population, require complete data without unobserved or missing cases, or do not accommodate time-varying infection or recovery rates as a result of dynamically changing interventions. The modified stochastic susceptible-exposed-infectious-recovered (SEIR) model presented in this paper addresses these three issues. Applicants developed this model within the framework of a Partially Observed Markov Process (POMP), which has been applied to introduce structural stochasticity into epidemic models (12). Applicants fit model parameters on case data for Harvard's 2016 mumps outbreak provided by the Massachusetts Department of Public Health (MDPH).

Applicants compared it to data from Ohio State University (OSU), one of the few universities that had extensive publicly available data through the CDC.

In applying our model, Applicants found that each of the interventions employed by HUHS—email awareness campaigns, more aggressive diagnoses where clinical symptoms alone were enough to result in quarantine, and strict isolation of suspected cases—were crucial in reducing the size and duration of the outbreak. In particular, Harvard's policies drastically increased the reporting rate of infection and shortened the time a person remains infectious in a susceptible population, relative to the baseline. As a result, one mumps case at Harvard infected less than two susceptible individuals on average, and much less once aggressive diagnosis was in place, compared to cases at non-residential schools like OSU, in which they infected an average of six susceptible individuals. However, the OSU data suggests that self-isolation could be effective, if adopted rigorously by students. The conclusions from this paper could guide future responses to infectious disease outbreaks on college campuses. Without effective measures in place, highly transmissible diseases like mumps, meningitis, and now COVID-19, spread in these environments at much faster rates than in the overall population and can lead to serious health complications. Simple interventions that ensure most cases are detected, treated, and separated from susceptible individuals make a significant difference.

Materials and Methods
Harvard Mumps Outbreak
Data

The mumps outbreak at Harvard began in February 2016, when six students reported onset of parotitis to HUHS. For the next three months, the number of cases continued to rise, until finally plateauing in late May and early June. There were two waves of the outbreak—one occurring in the month of March and a larger one occurring in mid-April—totaling 189 confirmed and probable cases (FIG. 1). Confirmed cases are those with a positive laboratory test for mumps virus. Probable cases are those who either tested positive for the anti-mumps IgM antibody or had an epidemiologic linkage to another probable or confirmed case (13, 14). The majority of these cases received the recommended two doses of MMR (15).

Applicants use data provided by MDPH, which documented every mumps case between 2015 and 2017 at schools across Massachusetts (16). This data includes demographics of the patient (gender, age, county, and institution), symptoms and vaccination status, date they reported their symptoms and the date of symptom onset, and lag time between the date of symptom onset and admission to a medical clinic.

Interventions

Harvard University employed three main interventions: (i) an email awareness campaign, (ii) more aggressive diagnoses, and (iii) strict isolation of infectious persons.

First, between February and May 2016, HUHS sent six different emails to Harvard students, employees, and colleagues with information on the gravity of the outbreak, recommendations on how to prevent transmission, and instructions on how to identify mumps. This raised awareness throughout the campus. Particularly at the peak of the outbreak, roommates, resident deans, and athletic coaches all played essential roles in reporting potential cases of mumps, so that few cases likely went undetected and untreated by HUHS (13, 14).

Second, Harvard acted vigorously to treat and isolate anyone suspected of mumps throughout the outbreak. Initially, due to the disease's non-specific symptoms and less extreme manifestation in vaccinated people, HUHS used positive mumps PCR tests as a necessary ground for diagnosis. Later, on recommendation from the MDPH, HUHS stopped automatically ruling out those with negative PCR results, given that false negatives were quite frequent in vaccinated individuals, and given some individuals reported their infection to the clinic belatedly (see Supplementary Materials for details on negative PCR tests) (17). Anyone who entered HUHS displaying clinical symptoms of mumps was now deemed infected and infectious. This change in the diagnosis protocol took place on Apr. 15, 2014, day 61 of the outbreak (14).

Third and perhaps most notably, Harvard isolated most confirmed or probable cases of mumps. While many universities simply suggest self-isolation in one's room or dormitory (which leaves roommates and friends highly susceptible to the disease), Harvard removed anyone with clinical symptoms of mumps from the population. Of the 230 total cases at Harvard between February 2016 and November 2017, 96 were isolated in alternate housing on campus, while 110 were isolated off-site. Although a person remains infectious with mumps for five days, Harvard isolated patients for six days for additional measure (13).

Harvard also used a variety of smaller techniques to contain the disease. For instance, water fountains with a weak upward flow were repaired in late March when it became apparent that students were directly touching the fountain with their water bottles or mouths (14). In this study, Applicants only considered the first three larger-scale interventions in our models. FIG. 1 shows a timeline of the interventions as well as periods when the population was fluctuating (such as during spring and summer break). Around two weeks after HUHS improved its criteria for diagnosis in mid-April, there was a steep decline in the number of new cases. These interventions were possible thanks to the ample resources that Harvard has at its disposal, which may not be available at other universities. Nevertheless, this situation makes Harvard an ideal testing ground for interventions that could not be deployed elsewhere, at least without solid proof of their efficacy. Thus, Applicants quantify the effects of the three main interventions (awareness campaign, aggressive diagnoses, and strict isolation of suspected cases) further in the modeling section of this paper.

Figure 10:
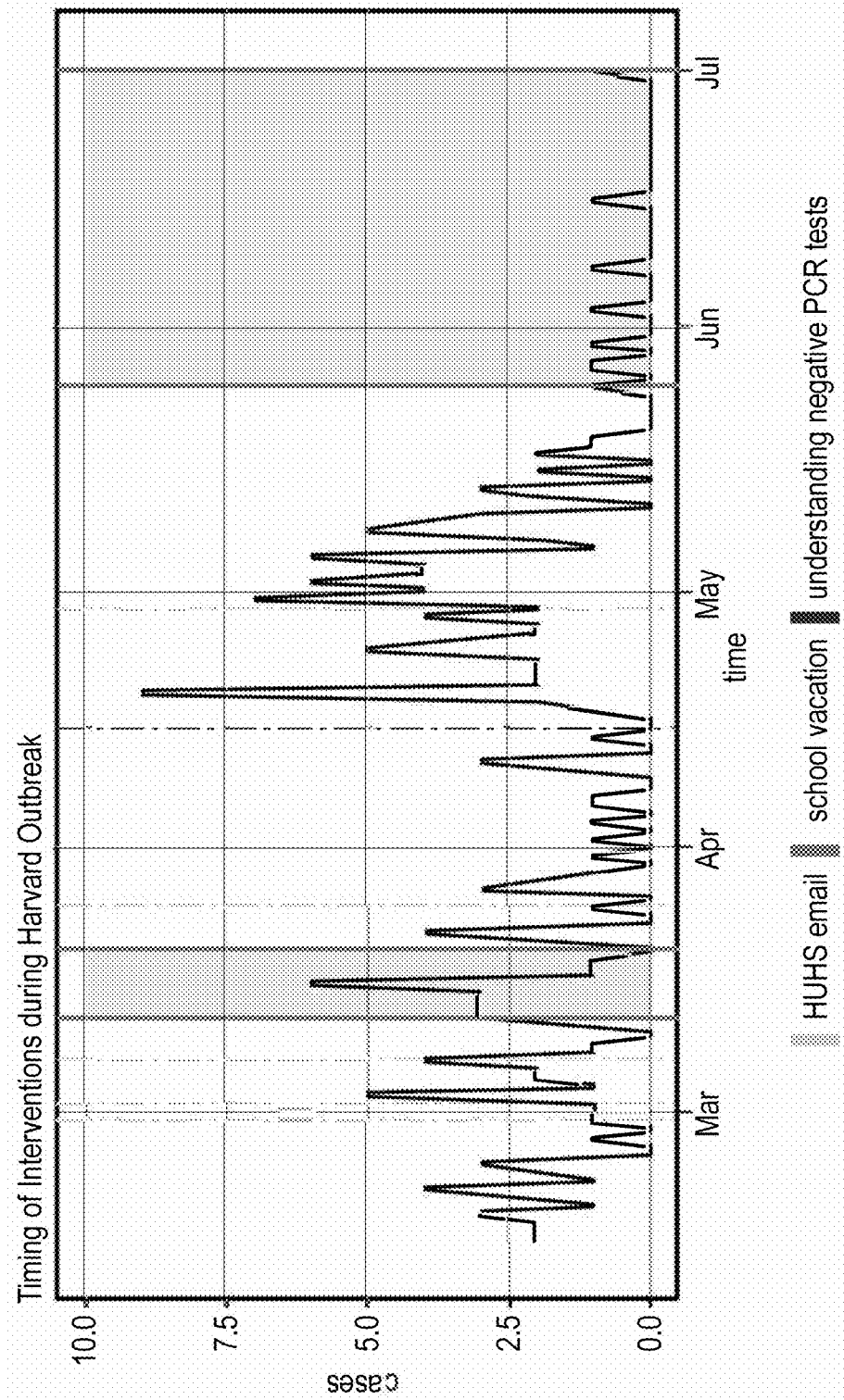
FIG. 10 is an illustration of the daily number of new mumps cases (probable or confirmed) at Harvard and the timeline of school vacations and control interventions employed by HUHS between February and June 2016.

In FIG. 10, the daily number of new mumps cases (probable or confirmed) at Harvard and the timeline of school vacations and control interventions employed by HUHS between February and June 2016. Both probable and confirmed cases display clinical symptoms of mumps, but only confirmed cases have a positive PCR result. HUHS sent multiple emails over the course of the outbreak, raising awareness about the spread of mumps. Additionally, in mid-April, HUHS began more carefully diagnosing mumps, rather than automatically ruling out those with negative PCR tests. The isolation policy is not shown because it occurred continuously.

Ohio State University Mumps Outbreak
Data on the Outbreak

In 2014, a large outbreak of mumps occurred in central Ohio, with the majority of cases linked to Ohio State University (OSU) in Columbus. The outbreak began in February 2014 and peaked in early April with 96 cases in one week. By summer and early fall, the number of cases had dramatically dropped and stabilized (8). Applicants therefore restrict our analysis of the outbreak to the time between Week 1 and Week 40 of 2014, in which there were a total of 528 cases (FIG. 2). Applicants obtained this data from CDC's Morbidity and Mortality Weekly Report (18). One drawback of the data is that the cases are reported weekly, making our analysis and parameter estimations less precise. Furthermore, Applicants cannot guarantee that all the cases in this dataset are linked to the university itself, but Applicants know from news reports that most cases in Ohio occurred on campus during the first half of 2014 (8). The proximity in time to the Harvard outbreak and the differences in response detailed below make this a good dataset to compare to.

Characteristics of the Response

Applicants were unable to acquire data directly from public health officials at OSU, and thus the exact timeline and range of interventions administered over this period are not known. Applicants learned through investigations that, like at Harvard, advisories were published by the university, notifying students of the issue and how to prevent its spread. One notice published by OSU's medical center reads: "Stay at home for five days after symptoms (salivary gland swelling) begins (required by Ohio law OAC 3701-3-13, (P)); avoid school, work, social gatherings, and other public settings" (19). These advisories were distributed since March 2014 (20), and local news outlets also started reporting the outbreak earlier in the month (21). It appears, however, that like most affected universities, OSU did not formally isolate infectious persons.

Figure 11:
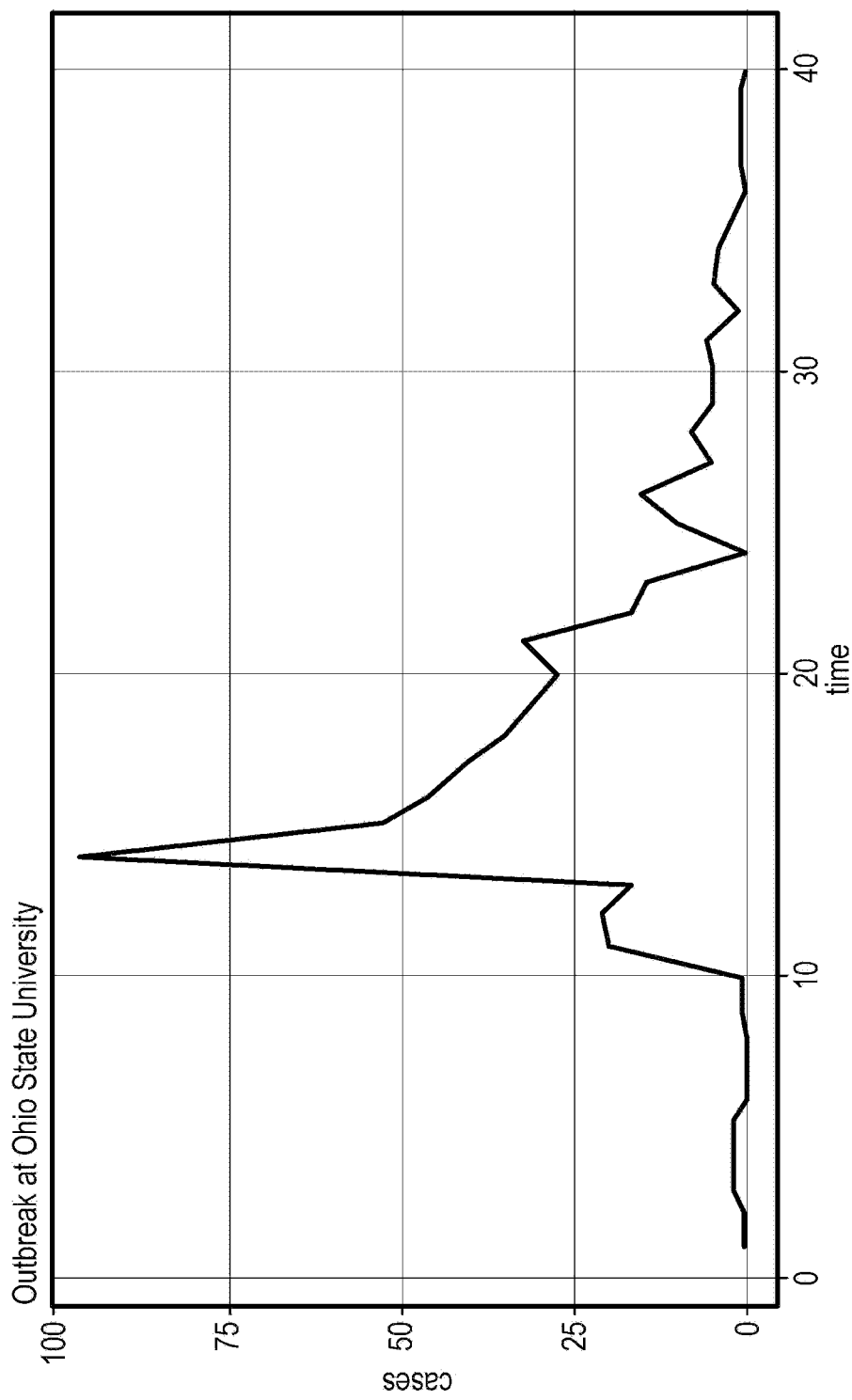
FIG. 11 is an illustration of a number of weekly mumps cases in Ohio (particularly Ohio State University) between January and September 2014.

In FIG. 11, a number of weekly mumps cases in Ohio (particularly Ohio State University) between January and September 2014. There were a total of 528 cases during this time period.

Epidemiological POMP Model

The epidemiology of mumps can be captured by a Susceptible-Exposed-Infected-Removed (SEIR) compartmental model: after exposure, individuals go through a latent non-infectious period, followed by an infectious phase (22). Infectious individuals are removed from the transmission process either by recovery or isolation, after which they become immune. Compartmental models simplify the mathematical modeling of infectious diseases; however, they assume access to fully observed disease data (see Suppl. materials). In reality, not all mumps cases are reported, and latent mumps carriers exhibit no symptoms at all. In order to address this issue, our approach integrates a standard SEIR model with a Partially Observed Markov Process (POMP) model (23). This allows us to combine the simplicity of compartmental models with a probabilistic framework for the underlying dynamics and the observed data. POMP models require the specification of a process model that describes stochastic transitions between the (unobserved) states of the system (in this case, the SEIR compartments), and a measurement model where the distribution of observed data (e.g.: confirmed cases) is expressed as a function of the unobserved states. The stochasticity introduced in the SEIR dynamics makes our model better suited to describe small populations, such as college campuses, where random fluctuations can be significant in relation to the size of the population. Applicants describe the process and measurement models below.

Process Model

The process model, defined as a stochastic SEIR model, provides the change in true incidence of mumps at every time point. Applicants add parameters that induce random fluctuations into the population and change the compartments' rates of transfer in response to interventions. Applicants do this by using probabilistic densities for the transition of state variables. Moreover, although disease dynamics are technically a continuous Markov process, this is computationally complex and inefficient to model, and so Applicants make discretized approximations by updating the state variables after a time step, $\delta$. Due to the varying granularity of the observed data (daily and weekly), Applicants used two different time steps: $\delta_H=2.4$ hours for Harvard and $\delta_O=12$ hours for OSU. The system of discretized equations is shown in Equation 1, where Bt is the number of susceptible individuals who become exposed to mumps, C(t) is the number of newly infectious cases, and Dt is the number of cases that are removed from the population:

$$S(t+\delta)=S(t)-B(t)$$

$$E(t+\delta)=E(t)+B(t)-C(t)$$

$$I(t+\delta)=I(t)+C(t)-D(t)$$

$$R(t+\delta)=R(t)+D(t)$$

$$S(t)+E(t)+I(t)+R(t)=N$$

Equation 1 describes how the sizes of the four compartments (susceptible, exposed, infectious, and removed) change between (t, t+$\delta$). The model further assumes that the population size N remains constant at every time point. Applicants added inherent randomness to our model by setting Bt, Ct, and Dt as binomials. If Applicants assume that the length of time an individual spends in a compartment is exponentially distributed with some compartment-specific rate xt, then the probability of remaining in that compartment for an additional day is exp(−x(t)) and the probability of leaving that compartment is 1−exp(−x(t)):

$$B(t) \sim Bin(S(t), 1-\exp(-\lambda(t))), \text{ where } \lambda(t) = \beta(t)\frac{I(t)}{N}$$

$$C(t) \sim Bin(E(t), 1-\exp(-\sigma))$$

$$D(t) \sim Bin(I(t), 1-\exp(-\gamma(t)))$$

The force of infection, $\lambda(t)$, is the transition rate between the susceptible and exposed classes at time t, and can be expressed as $$\beta(t)\frac{I(t)}{N}$$

where $\beta(t)$ represents the transmission rate of the disease. The removal rate between the infectious and removed compartments at time t is given by $\gamma(t)$, and transition rate between the exposed and infectious classes is $\sigma$. Therefore, $\gamma(t)^{-1}$ represents the mean length of time a person is infectious before being removed from the population (either because of intervention efforts or natural recovery), while $\sigma^{-1}$ represents the mean length of time a person stays in the latent stage. With this notation, Applicants are implicitly assuming that the transmission and removal rates could change over time due to interventions or changes in behavior, while the duration of the latent stage is constant and determined by the physiopathology of the disease. Applicants will justify these assumptions for Harvard and OSU next, as well as provide explicit formulas for $\beta(t)$ and $\gamma(t)$.

Leaving aside the unlikely possibility of change in pathogen's infectivity, the transmission rate $\beta(t)$ essentially depends on the frequency of exposure events. In the case of Harvard, its nature as a residential campus would lead to significant decreases in student population, and therefore exposures, during school vacations. Exposure at OSU, a non-residential campus, is arguably less affected by vacation breaks. Another potential cause for reduction in exposures is awareness campaigns resulting in the adoption of preventive behaviors by students. Both Harvard and OSU adopted such campaigns, in the former, implemented as emails regularly sent out by HUHS recommending personal hygiene and testing in case of symptoms compatible with mumps; in the latter, in the form of advisories posted around campus and online, advising self-isolation to those students who presented symptoms. Furthermore, due to the scale of the mumps outbreak in Ohio, it received local and national news coverage, particularly in connection with OSU. Anecdotal evidence (i.e.: conversation with students) and, most importantly, the fact that HUHS emails were throughout the outbreak, make us conclude that emails were not particularly effective. On the other hand, news coverage in the case of OSU could have had led to additional awareness by students and encourage some to self-isolate. Applicants argue that self-isolation results in lowering of transmission rate, not shortening of the removal time, because it is not perfect quarantine and people can still interact and become exposed, albeit at a lower frequency. Based on these known facts and our interpretation of them, Applicants propose the following transmission rate $\beta_H(t)$ for the Harvard model:

$$\beta_H(t) = p\beta_H, t0 \le t \le t1 \text{ or } t \ge t2$$
$$= \beta_H \text{ otherwise}$$

Here, t0 and t1 represent the starting and ending dates for the spring break (Mar. 12-20, 2016), and t2 the beginning of the summer recess (May 26, 2016). The constant $\beta_H$ is the baseline transmission rate during normal class term, and the parameter p is a number between 0 and 1 that accounts for the reduction of student population on campus during the school vacation. In the case of OSU, Applicants propose:

$$\beta_O(t) = w\beta_O, t \ge \zeta$$
$$= \beta_O \text{ otherwise}$$

In this equation, $\beta_O$ the baseline transmission rate, w is a constant lower than 1, and the time when students began to self-quarantine. Based on publication of public health advisories and local news, Applicants set this time as the last week of March 2014 (week 12).

The removal rate $\gamma(t)$ can also be affected by interventions and personal behaviors. Applicants know that HUHS diagnosis protocol changed on day 61 of the outbreak at Harvard, resulting in a shorter average removal time since clinical presentation of symptoms alone was enough to result in strict isolation of suspected cases. Thus, Applicants propose the following $\gamma_H(t)$ for Harvard:

$$\gamma_H(t) = q\gamma_H, t \ge \tau$$
$$= \gamma_H, t < \tau$$

Here, q is a constant greater than 1 and $\tau$ is the date when the new criteria was implemented (Apr. 15, 2014). The constant $\gamma_H$ is the baseline removal rate reflecting the impact of the original diagnosis protocol. In the OSU model, on the other hand, Applicants assume a constant recovery rate equal to the population average for mumps, since infected individuals self-isolate at home. This would not result in a strict quarantine but in a reduced contact rate with susceptible individuals, which is already modeled by a lower transmission rate in equation (4).

Finally, it is necessary to estimate the basic reproduction number, R0, which equals the expected number of secondary cases produced by an infectious person in a completely susceptible population (22). R0 measures the initial growth rate of an outbreak and so, if it is less than 1, then the infection will die out and there will be no epidemic. For our stochastic SEIR model, this constant can be expressed as R0=$\beta/\gamma$ (24). Meanwhile, the time-dependent effective reproduction number is defined as $R_E(t)=\beta(t)/\gamma(t)*S(t)/N$, but because S(t)≈N, Applicants can simplify this expression to $R_E(t)\approx\beta(t)/\gamma(t)$. Both the basic and effective reproduction numbers allow us to understand the strength of an outbreak.

Measurement Model

Although it is impossible to directly record the number of people that are susceptible, exposed, infectious, and removed directly, the MDPH and CDC data tells us the number of observed cases per day. The mean number of observed cases per day is the true number of cases multiplied by the reporting rate $\rho$ ($\rho$<1). However, rather than simply denoting the observed number of cases as a binomial distribution, Applicants account for greater variability in the measurements than a binomial distribution expects, since college populations are "small" (comparted to cities and larger administrative units) and more affected by random fluctuations (25). Thus, the number of observed cases, yt, given the number of true cases, C(t), can be best modelled by an overdispersed binomial distribution defined as a discretized Normal random variable:

$$y_t | C(t) \sim \text{Normal}(\varrho\ C(t), \varrho\ (1-\varrho)C(t)+(\psi\varrho\ C(t))^2)$$

The parameter $\Psi$ handles the increased variability in a small population. If $\psi$=0, the variance in our measurement model simplifies to the variance for a binomial distribution.

Final POMP Model

The process and measurement models define our final POMP model. For each time point, the process model generates the number of new cases based on binomially distributed counts. The measurement model then estimates the observed number of cases based on the true number of cases and reporting rate. The free parameters in our POMP models for Harvard and OSU that need to be estimated from the data are the following: (i) $\beta_H$ and $\beta_O$, baseline transmission rates, (ii) p and w, decrease in transmission rate at Harvard and OSU due to vacation and self-isolation, respectively, (iii) $\gamma_H$ baseline removal rate at Harvard (iv) q, increase in removal rate due the updated HUHS diagnosis protocol, (v) $\rho_H$ and $\rho_O$, case reporting rates, (vi) $\psi_H$ and $\psi_O$, overdispersion coefficient representing additional variability in the populations.

Fixed Parameters

In addition to the free parameters to be estimated from the observed case data, our models also include a number of fixed parameters, shown in Table 1, whose values can be inferred directly from previous knowledge or available information. As mentioned earlier, Applicants chose $\tau$=61 days and $\zeta$=12 weeks because those points in time at Harvard and OSU correspond to the introduction of the interventions that Applicants hypothesized to be impactful in the dynamics of the respective outbreaks. Dates t0, t1, and t2 for the spring and summer vacations at Harvard are available online (26). Applicants set the rate between the exposed and infectious classes and the recovery rate to $\tau=1/17$ and $\gamma=1/5$, respectively, since the average latent period and recovery time for mumps are known to be $\sigma^{-1}=17$ days and $\gamma^{-1}=5$ days (5). Finally, Applicants set the effective population size at Harvard $N_H=20,000\times0.53=10,600$ people based on records of Harvard's enrollment and employment, and Grad and Lewnard estimation of susceptibility to mumps among college-age adults due to immunity waning (5). Similarly, use an effective population for OSU given by $N_O=60,000\times0.53=31,800$, using the total enrollment for the 2013-2014 academic year reported in OSU's statistics website (27).

extent these interventions made a difference on the trajectory of the outbreak. First, Applicants compared the scenario with the interventions versus a scenario without the interventions. Controlling for all other parameters, Applicants run two sets of simulations at the MLEs, with 200 simulations each. The first set of simulations fixed q and w at the value obtained from MLE, while the second set of simulations set q and w to 1, assuming that no interventions occurred around day 61 at Harvard and by week 12 at OSU. Applicants then compared the cumulative number of cases over time for these two sets of simulations, generating a 95% percentile range from all the simulations in each set. Second, Applicants used this method to determine if administering the interventions earlier could have lowered the number of

TABLE 1

List of fixed parameters used in mumps transmission model for Harvard and OSU

| Symbol | Description | Value | Units | Source |
| --- | --- | --- | --- | --- |
| $\tau$ | Date of intervention at Harvard | 61 | day | Harvard records on interventions (14) |
| $t_0, t_1, t_2$ | Vacation dates at Harvard, 2015-2016 academic year | 26, 34, 100 | day | Harvard archived academic calendar (26) |
| $\zeta$ | Date of intervention at OSU | 12 | week | |
| $\sigma^{-1}$ | Duration of mumps latent period | 17 | day | Lewnard and Grad (5) |
| $\gamma^{-1}$ | Duration of mumps recovery period | 5 | day | Lewnard and Grad (5) |
| $N_H$ | Effective population at Harvard | 10,600 | — | Harvard records on population size (15) and mumps susceptibility among college-aged individuals (5) 18 |
| $N_O$ | Effective population at OSU | 31,800 | — | OSU's statistical summary (27) and mumps susceptibility among college-aged individuals (5) |

Maximum Likelihood Estimation of Free Parameters

In order to obtain estimates of the free parameters in our models, Applicants pick the parameter values that maximize the log likelihood of the observed data given each model. Within the POMP framework, Applicants can perform fast maximum likelihood estimation (MLE) via Sequential Monte Carlo (SMC) techniques (23). SMC allow us to calculate the likelihood of the data more efficiently by applying the Markov property to generate paths in parameter space that sample the likelihood surface. Applicants performed 100 searches from random parameter guesses, each converging to a unique value, and Applicants then took the maximum over the 100 runs the final point estimates. Applicants did this using the pomp package version 2.8 (28) for the R statistical software version 3.6.1 (29). In order to calculate the confidence intervals for each parameter, Applicants selected the top decile from the set of parameters values obtained in the SMC runs, and applied the adjusted bootstrap percentile (BCa) method (30) with 10,000 bootstrap replicates using the function boot.ci in version 1.3.20 of package boot for R (31).

Intervention Analysis

Finally, Applicants performed an analysis of the parameters q and w, which respectively quantify the effect of what Applicants consider to be the defining intervention at Harvard (aggressive diagnosis) occurring around day 61 of the outbreak, and the self-isolation campaign at OSU during March 2014. This could allow us to understand to what extent these interventions made a difference on the trajectory of the outbreak.

cases. For Harvard, Applicants let the day of the intervention take on values between 1 and 60. Subsequently, Applicants run simulations for each of these 60 cases, pull the final outbreak size from the median simulation, and calculate the reduction in outbreak size. Applicants applied the same procedure for OSU, in this case varying the day of intervention between 1 and 11 and calculating the corresponding final outbreak sizes.

Results

Optimal Parameters of Harvard and OSU Outbreaks

The MLEs of the parameters provide insight into the key characteristics of Harvard's and OSU's outbreak. In general, Applicants observe very good agreement between the observed cases and the simulated outbreaks using the optimal parameters. The effective reproduction number also reflects the effects of the interventions at Harvard and OSU in way that's consistent with our initial modeling assumptions. The bootstrap sampling method results in narrow 95% CIs.

Maximum Likelihood Estimates for Harvard

The results are shown in Table 2. Notably, the baseline removal rate H is quite high, indicating that the initial diagnosis protocol was quite effective at identifying and removing infected students from the population, but it was further increased after day 61. It is also remarkable the very high reporting rate $\rho_H$, which suggests that HUHS was able to identify most of the cases circulating at Harvard.

TABLE 2

List of parameters in the Harvard model that obtained by MLE or calculated using the estimated parameters.

| Symbol | Description | Point estimate | 95% CI | Units | Source |
|---|---|---|---|---|---|
| $\beta_H$ | Baseline transmission rate | 1.39 | (1.35, 1.49) | day$^{-1}$ | MLE |
| $\gamma_H$ | Baseline removal rate | 0.85 | (0.86, 0.93) | day$^{-1}$ | MLE |
| p | Decrease in infection due to vacation | 0.11 | (0.06, 0.13) | — | MLE |
| q | Increase in removal rate | 2.8 | (2.16, 2.56) | — | MLE |
| $\varrho_H$ | Proportion of infections reported | 0.97 | (0.93, 0.97) | — | MLE |
| $\psi_H$ | Overdispersion parameter | 0.54 | (0.5, 0.56) | — | MLE |
| $R_E(t)$ | Effective reproduction number | 1.63 normal term<br>0.18 during vacation<br>0.58 after intervention | — | — | Calculated as $\frac{\beta(t)}{\gamma(t)}$ |

Applicants ran stochastic simulations of Harvard's outbreak using the parameter values from Table 2. FIG. 3 shows consistent results across simulations. Shortly after day 61 (the time of the primary intervention), Applicants consistently see a decrease in the number of observed cases. The variability in the simulations can partly be attributed to the randomness in the stochastic model as well as the overdispersion parameter. Variability can also be explained by the MLE of the basic reproduction number being below 2, which together with the stochasticity built into the simulations, can result in absence of outbreak, such as in simulation 8, or much smaller outbreaks like in 5, 7, and 9.

Maximum Likelihood Estimates for OSU

The MLEs of the parameters for the OSU model, as well as derived quantities, are shown in Table 3. Here Applicants can see an initial reproductive number of almost 6, however, within the context of our hypothesis assuming that awareness campaigns from OSU (perhaps helped by news reporting about the outbreak) leads to self-isolation that decreases interactions while keeping the same removal time, the intervention seems effective to reduce the reproductive number below 1.

on day 61 could be up to four times the size of the actual outbreak (FIG. 5A). These results also indicate that the outbreak would have lasted much longer, if not for these vigilance-increasing strategies. Using the outbreak sizes obtained by varying the day of the intervention from 1 to 61, Applicants obtained a linear regression between day of intervention and reduction of the outbreak (FIG. 5C). The fitness of the regression is very high (R=0.96, P<10-9), quick inspection of the plot reveals that if the new diagnosis protocol was implemented within the first 10 days of the outbreak, then no more than 50 students would have been infected in total at Harvard.

For OSU Applicants observe similar trends. Lack of intervention on week 12 could have resulted in an outbreak twice as large (FIG. 5B). The outbreak size as a function of the intervention week also shows a strong dependency, but in this case non-linear and best fitter with a sigmoid function of the form 1/(1+eweek-12). Using his transformation, the fit is also very good (R2=0.63, P<0.005). Here Applicants can conclude that intervening earlier would have had a major effect as well: if the awareness campaigns prompting stu-

TABLE 3

List of parameters in the OSU model that obtained by MLE or calculated using the estimated parameters.

| Symbol | Description | Point estimate | 95% CI | Units | Source |
|---|---|---|---|---|---|
| $\beta_O$ | Transmission rate constant | 1.19 | (1.19, 1.2) | day$^{-1}$ | MLE |
| w | Decrease in infection due to self-isolation | 0.16 | (0.158, 1.162) | — | MLE |
| $\varrho_O$ | Proportion of infections reported | 0.03 | (0.029, 0.03) | — | MLE |
| $\psi_O$ | Overdispersion parameter | 0.38 | (0.374, 0.381) | — | MLE |
| $R_E(t)$ | Effective reproduction number | 5.95 initial<br>0.95 after advisory | — | — | Calculated as $\frac{\beta(t)}{\gamma(t)}$ |

As with Harvard, Applicants run stochastic simulations of OSU's outbreak using the parameter values from Table 3. The simulated outbreaks are shown in FIG. 4, and they recapitulate the real curve with some random variation doe to the stochastic nature of the model.

Earlier Intervention Decreases Outbreak Size at Harvard and OSU

The results from the intervention analysis for Harvard and OSU is depicted in FIG. 5. By the final day of the Harvard outbreak (day 130), the simulation without the interventions dents to self-isolate had started up to week 5 or 6, then it appears likely that outbreak would have been eradicated.

Discussion

Parameter Interpretation

The MLEs give us insight into characteristics of the mumps outbreaks the Harvard University in 2016 and Ohio State University in 2014, as measured by their effective reproduction numbers RE, intervention parameters q and w, rates of removal y, reporting rates p, and overdispersion parameters Ψ. At Harvard, $R_E$ during normal class term was 1.63, which indicates that the outbreak was growing, even though testing and isolation by HUHS resulted in a baseline removal time of only 1/0.85=1.2 days. This points to the effectiveness of the quarantine system implemented by HUHS. However, a small fraction of false negative cases still managed to escape quarantine and keep the virus under circulation, as indicated by the reproduction number being higher than 1. The reproduction number goes below 1 during the spring break, which is reasonable given that most students are away given the residential nature of the Harvard campus. However, transmission resumes after the break. It is only after the implementation of the new diagnosis protocol, which was less stringent by requiring clinical symptoms alone for isolation, on day 61 that had a dramatic effect on the detection and isolation of positive cases, effectively taking the removal time to less than 1 day and the reproductive number below 0.6. Thanks to this key intervention, it was possible to end the outbreak before the beginning of the summer recess.

The estimate of $\rho$ is 0.96, which implies the reporting rate at Harvard was remarkable. Reasons include the email awareness campaign, a community network—from resident deans to athletic coaches—reporting students and employees who seemed at-risk, and more aggressive diagnoses, particularly towards the end of the outbreak. The estimate for $\Psi$ is 0.54, suggesting that the actual data has more variability than expected under the assumed distribution. If $\Psi$ had been approximately 0, the variance in our measurement model would have simplified to the variance for a binomial distribution. However, because the 95% confidence interval is (0.5, 0.56) and thus does not include 0, Applicants justify the modelling decision of representing the number of cases as an over-dispersed binomial. Demographic and environmental stochasticity (e.g.: a student in the midst of midterm season may be less likely to report symptoms), as well as the interventions themselves (e.g.: reporting may increase temporarily after an awareness email) can result in over-dispersion in the number of reported cases.

In the case of OSU, Applicants obtain a much higher reproduction number at the beginning of the outbreak, near 6, and a very low reporting rate of 3%. Before discussing these results any further, it is important to keep in mind that Applicants extrapolated OSU cases from state-level reports by the CDC. Furthermore, Applicants did not have direct access to information about the containment interventions adopted by the school, as Applicants did for Harvard, so Applicants were only able to make educated guesses about those possible interventions based on information Applicants found on the web. However, the internal consistency of the resulting model and the good agreement with the available data, gives some weight to these results. Within our OSU model, Applicants see that the assumed self-isolation of students motivated by the advisories posted by OSU, online and possibly on campus as well, had the intended effect of stopping the outbreak. The effective reproduction number dips beyond 1 after March, which is when the awareness campaign appeared to have started, and also when the outbreak gained local and national prominence due to news reporting. The low reporting rate is compatible with a large, non-residential campus where it is harder to reach out to students as they live scattered around the city, and also closer to population-wide estimates of this parameter (5). A consequence of this number is that the outbreak should have been 30 times larger than observed. Since the observed case count is approximately 500, it follows that the total number of cases could have reached 15,000 individuals, which is still possible given that the number of susceptible within the school's student population is over 30,000. This is still a very significant number, and it is possible that a large majority of these potential 15,000 cases only had mild symptoms. Also, the non-residential nature of OSU probably has an effect on the assumptions of the underlying SEIR model: even though the closed compartment assumption of the SEIR model is always an approximation, it might be even more so for OSU than for Harvard because students of the former have more opportunity to interact with individuals outside of their school, resulting in additional transmissions that are not captured by our model, and thus affecting the interpretation of parameters such as the reporting rate.

Effect of Strict Isolation Policy Vs Self-Isolation

Arguably the most critical intervention by HUHS was the isolation requirement for confirmed and probable mumps cases. By comparing the Harvard and OSU outbreaks, Applicants conclude that the isolation policy led to a smaller average infectious period for Harvard patients. The MLEs for Harvard and OSU are different for several parameters, most notably basic reproduction number, reporting rate, and rate of transition from the infectious to removed class. Firstly, OSU's basic reproduction number is over four times that of Harvard. Harvard's isolation policy best explains this difference because it physically prevents infectious persons from causing multiple secondary infections, thus suppressing the growth of the outbreak. Secondly, OSU's reporting rate is extremely low, at approximately 3% compared to Harvard's 96%. Applicants do not have access to OSU's diagnostic procedures nor do Applicants know the extent of their email awareness campaign, but Applicants hypothesize that a lack of one or both of these may explain at least a portion of the dissimilarity in the two schools' reporting rates. However, the reduction in OSU's transmission rate Applicants observe in our model post-intervention is still very significant at 94%, and would have been a major contributor to help containing the outbreak there. This suggests that compliance with easy-to-implement measures such as self-isolation could go a long way towards outbreak mitigation. Of course, high compliance is contingent on good educational and awareness campaigns by the health authorities.

Implications of Intervention Analysis

With the benefit of our intervention analysis, Applicants conclude that aggressive diagnoses decreased the size of the Harvard outbreak by approximately three-fourths. Furthermore, for every day of intervention delay, Applicants estimate that the outbreak size would have increased by 1.6 percentage points, extrapolating the regression line in FIG. 5C. Likewise, self-isolation prompted by health advisories posted by the university reduced the size of the OSU outbreak by half. Given the non-linear dependency between change in outbreak size and timing of intervention (FIG. 5D), the increase would have been even larger in that outbreak. Interestingly, this dependency also implies that self-isolation in the first weeks of the outbreak can be enough to completely stop spread.

Clearly, a limitation of this analysis is the assumption that everything remains the same while changing the time of the intervention under consideration. In reality, other factors might come into play if the outbreak becomes larger or smaller, which in turn could affect the dynamics of the outbreak as well as the interventions themselves. However, this analysis still provides a useful hypothetical quantification of the effect of accelerating or delaying interventions designed to contain the spread of an outbreak and here, as expected, the sooner the interventions are introduced, the better outcomes in terms of outbreak size. Of course, existing constrains in the school's health system could impede fast interventions. In such situations, our method can be useful to perform a cost-benefit analysis of how late an intervention could be made to still have a significant reduction in the health burden caused by the disease.

Conclusions

Applicants constructed and parametrized a POMP model for the transmission of mumps on college campuses. Unlike other models of infectious disease, which opt for deterministic representations, our stochastic model is adaptable to small populations and accounts for the noisiness and incompleteness of case data. Moreover, it incorporates parameters that measures the effect of interventions implemented after a given point in time. Given the worldwide crisis caused by the COVID-19 pandemic, such models can be useful to quickly evaluate interventions designed to contain the spread of SARS-CoV-2 once schools reopen in the U.S. and around the world.

Applicants compared an outbreak at Harvard University, with its various intervention strategies, to another university outbreak of comparable reported cases at OSU. Importantly, while most literature today focuses on mumps prevention—such as administering third MMR doses to college-age students—this paper provides quantitative backing for more immediate and less costly approaches to mitigating the spread of mumps and other infectious diseases, most notably COVID-19, for which there is no vaccine yet available. In particular, proactive diagnosis of highly infectious diseases such as mumps and COVID-19 would benefit from less stringent tests that result in strict isolation only on clinical suspicion. Effective awareness campaigns that lead to self-isolation of infected individuals with mild symptoms can also have a significant effect in containing the spread of disease and limit the risk for vulnerable populations.

Limitations

Some of our conclusions are likely affected by confounding factors that Applicants cannot control for in this analysis. For example, the fact that the outbreak at Harvard start to subside in late April, not long before students finish the semester and leave campus, which would decrease the number of potential infections. The most promising method to determine the exact effect of isolation strategies is through a randomized control trial. Regarding the differences between OSU and Harvard parameters, Applicants must be cautious in taking the OSU estimates at face value. Given that the OSU data consists of weekly reports rather than daily reports of cases, Applicants should expect the estimates for the parameters to be less accurate. Furthermore, the cases are not solely linked to the university. Numerous cases in the data occurred in the greater Columbus area, suggesting that the parameter estimates do not only account for the dynamics of mumps on campus. Lastly, major differences in housing and campus characteristics could have also contributed to differences between the two schools; for instance, OSU's population size is three times that of Harvard, and OSU has larger dorms than Harvard's houses. Interventions used at Harvard simply may not have worked as well at OSU. Applicants were fortunate to have direct access to school administrators who were involved in the response to the 2016 outbreak to discuss HUHS interventions in detail, but Applicants were not able to get the same level of detail for OSU's interventions, as discussed in the main text. More broadly, lack of publicly available datasets, with the exception of CDC reports on OSU's outbreak, is a serious impediment to perform these analyses.

Therefore, it will be essential that universities across the US and globe actively share data for comparative analysis, to identify the best intervention strategies to protect college campuses from outbreaks, especially in the post-COVID-19 world.

Competing Interests: Applicants declare no competing interests.

Source Code: Available at github.com/broadinstitute/mumps-pomp-models

Author's Contributions: MS participated in the design of the study, carried out the data analysis, developed the epidemiological models, generated the conclusions, and drafted the manuscript; GF developed the epidemiological models, and generated the conclusions; AC conceived of the study, participated in the design of the study, coordinated the study, and helped draft the manuscript; SF and PJB provided data on the HUHS interventions and reviewed the final draft of the manuscript; PCS overviewed the study and reviewed the final draft of the manuscript. All authors gave final approval for publication.

Acknowledgements: The authors would like to thank Jonathan Grad and Joseph Lewnard for providing feedback on the study design, Hayden Metsky for reviewing the manuscript, members of MDPH for providing access to the Harvard data, and Bridget Chak and Shirlee Wohl for guiding in the interpretation of the data.

Ethics: Usage of Harvard University data for development of the SEIR model was approved by the Massachusetts Department of Public Health (MDPH) through protocol 906066. Harvard University Faculty of Arts and Sciences and the Broad Institute ceded review of secondary analysis to the MDPH IRB through institutional authorization agreements. The MDPH IRB waived informed consent given this research met the requirements pursuant to 45 CFR 46.116 (d). Data from Ohio State University was obtained from the CDC's Morbidity and Mortality Weekly Report 2014. The Broad Institute has determined usage of this data constitutes non-human subjects research.

Funding: Howard Hughes Medical Institute, US National Institutes of Health.

REFERENCES FOR THIS EXAMPLE

1. Impact of the COVID-19 pandemic on education Wikipedia, the free encyclopedia2020 [updated 30 May 2020. Available from: en.wikipedia.org/wiki/Impact_of the-_COVID-19_pandemic_on_education.
2. Rosenberg J S. Will Harvard's Campus Reopen for Fall? Harvard Magazine. 2020.
3. Costill D. College campus outbreaks require timely public health response. Healio [Available from: goo.gl/aW7GaT.
4. Hurtado C. The Rise of Mumps in the United States Outbreak Observatory [Available from: www.outbreakobservatory.org/outbreakthursday-1/12/7/2017/the-rise-of-mumps-in-the-united-states.
5. Lewnard J A, Grad Y H. Vaccine waning and mumps re-emergence in the United States. Science Translational Medicine. 2018; 10(433).
6. Nishiura H, Kobayashi T, Miyama T, Suzuki A, Jung S-m, Hayashi K, et al. Estimation of the asymptomatic ratio of novel coronavirus infections (COVID-19). International Journal of Infectious Diseases. 2020; 94:154-5.
7. Shah M, Quinlisk P. Weigel A, Riley J, James L, Patterson J, et al. Mumps Outbreak in a Highly Vaccinated University-Affiliated Setting Before and After a Measles- Mumps-Rubella Vaccination Campaign—Iowa, July 2015—May 2016. Clinical Infectious Diseases. 2018; 66(1):81-8.
8. Golwalkar M, Pope B, Stauffer J, Snively A, Clemmons N. Mumps Outbreaks at Four Universities—Indiana, 2016. MMWR Morb Mortal Wkly Rep. 2018; 67(29): 793-7.
9. Bixler J, Botelho G. Over 360 cases of mumps in central Ohio, most of them tied to OSU. CNN [Available from: www.cnn.com/2014/05/16/health/ohio-mumps/index.html.
10. Mumps Cases and Outbreaks Centers for Disease Control and Prevention [Available from: www.cdc.gov/mumps/outbreaks.html.
11. Isolation Expenses (2016-2017). Harvard University Health Services; 2017.
12. Stocks T, Britton T, Höhle M. Model selection and parameter estimation for dynamic epidemic models via iterated filtering: application to rotavirus in Germany. Biostatistics. 2018.
13. Barreira P, Fitzgerald S. Personal communication. 2018.
14. Correspondence regarding Mumps 2016, Spring to Summer. Harvard University Health Services.
15. Mumps List for CDC. Harvard University Health Services.
16. Massachusetts Mumps Case Data between 2015 and 2017. Massachusetts Department of Public Health.
17. Bitsko R H, Cortese M M, Dayan G H, Rota P A, Lowe L, Iversen S C, et al. Detection of RNA of mumps virus during an outbreak in a population with a high level of measles, mumps, and rubella vaccine coverage. J Clin Microbiol. 2008; 46(3):1101-3.
18. Morbidity and Mortality Weekly Report. 2014.
19. Mumps Outbreak FAQs: The Ohio State University; [Available from: www.osu.edu/assets/mumps/faqs.pdf.
20. The Ohio State University Mumps Outbreak FAQs Columbus Public Health; 2014 [Available from: http://www.ccchd.com/documents/contentdocuments/doc_23_5_516.pdf.
21. Zeltner B. Mumps outbreak at Ohio State: Five things you need to know cleveland.com2014 [updated Jan. 12, 2019. Available from: www.cleveland.com/healthfit/2014/03/mumps_outbreak_at_ohio_state_f.html.
22. Martcheva M. An Introduction to Mathematical Epidemiology: Springer; 2015.
23. King A A, Nguyen D, Ionides E L. Statistical Inference for Partially Observed Markov Processes via the R Package pomp. Journal of Statistical Software. 2016; 69(12): 43.
24. Brauer F, Van den Driessche P, Wu J. Mathematical epidemiology: Springer; 2008.
25. He D, Ionides E L, King A A. Plug-and-play inference for disease dynamics: measles in large and small populations as a case study. Journal of The Royal Society Interface. 2010; 7(43):271-83.
26. Academic Calendar: 2015-16: Harvard Law School; 2015 [Available from: hls.harvard.edu/dept/academics/academic-calendar/academic-calendar-2015-16/.
27. The Ohio State University—Statistical Summary: The Ohio State University; 2013 [Available from: www.osu.edu/osutoday/stuinfo13.php.
28. King A A, Ionides E L, Bretó M C, Ellner S P, Ferrari M J, Kendall B E, et al. pomp: Statistical Inference for Partially Observed Markov Processes. 2020.
29. R Core Team. R: A Language and Environment for Statistical Computing. 2019.
30. Davison A C, Hinkley D V. Bootstrap Methods and Their Applications: Cambridge University Press; 1997.
31. Canty A, Ripley B D. boot: Bootstrap R (S-Plus) Functions. 2017.

Example 3—Pilot Study Summary, Preventing Outbreaks Through Real-Life Simulations Public health officials and citizens were not prepared for SARS-CoV-2, but realistic simulations can help us anticipate future phases of the pandemic—and better prepare for the next one. In 2015, Applicants launched Operation Outbreak (OO), an educational platform paired with a mobile app that uses Bluetooth to simulate the spread of a virtual "pathogen" on smartphones, and incorporates interventions such as rapid diagnostics, face masks, and vaccines. OO also generates ground-truth contact-tracing data on transmission events, which can improve epidemiological models. Before SARS-CoV-2 spread, Applicants used OO to simulate the emergence of a strikingly similar virus (SARS-like, R0 of 2-3, asymptomatic spread) in varied settings including middle-school classes and large research conferences. Here Applicants present data and insights from those simulations, and propose ways to leverage OO and related tools to prevent, model, and respond to the current pandemic and those in years to come.

Introduction

As countries hard-hit by SARS-CoV-2 begin to re-open, many are debating how best to resume K-12 and higher education at residential and day schools in a way that limits further spread of the virus. There are historical reasons to worry: the nationwide sweep of the 1957 flu pandemic has been attributed to the reopening of schools (Cauchemez 2009, Saunders-Hastings 2016). In the absence of a SARS-CoV-2 vaccine, public health and education authorities have advocated for a wide range of interventions, including face masks, social distancing, and small class sizes. However, the efficacy and sustainability of these interventions is difficult to know in advance, for two key reasons: (1) The success of any intervention will depend heavily on whether students and other stakeholders are educated, equipped, and motivated enough about it to remain compliant. (2) Applicants currently lack predictive models that can anticipate the effects of each intervention on transmission and behavior, as well as adequate "ground truth" data to accurately simulate these effects.

Here, Applicants present a new way to address both problems simultaneously: Operation Outbreak (OO), a pandemic prevention curriculum and data-driven platform that uses Bluetooth technology to simulate the spread of a virtual "pathogen" in real-time across smartphones and other devices in close proximity. Students engage with OO by first learning about biology, public-health, and civics topics related to outbreak containment. The culminating event is a simulated outbreak—facilitated via the OO smartphone app—that calls upon and reinforces the lessons they have learned. The platform and curriculum are paired with post-simulation reflection and analysis exercises designed to reinforce key points that can inform students' future responses to real outbreaks.

While students are participating in the simulation, the OO platform automates contact-tracing in real-time by recording all "transmission events" as well as other resulting changes in behavior. This yields critical data that are missing from most real-life outbreak-related datasets. The data are accessible via a web-based dashboard where users can visualize real-time information on simulated infection and transmission patterns, or download the data to conduct more complex analyses, such as construction of epidemiological models.

Mere weeks before SARS-CoV-2 jumped to humans, Applicants ran several OO simulations that mimicked plausible SARS-like outbreaks in which transmissions were caused by a significant fraction of pre-symptomatic carriers. These took place in both educational and conference settings with hundreds of participants in close proximity, and involved incorporating into the app epidemiological parameters representative of early outbreaks of SARS and MERS. The app-generated data from these simulations represented the ground truth of the mock outbreaks and the dynamics of transmission, which are not possible to fully observe during a real outbreak. The simulations captured a number of important features of SARS-CoV-2 and allowed us to explore new modeling approaches. They also allowed us to observe behavioral changes among participants—many of which are now being mirrored in real life.

In this article, Applicants describe the predictive power of our OO simulations, share the epidemiological data from our virtual outbreaks, discuss the ways in which they can inform existing mathematical models, and propose ways to use OO to reimagine education in the coming year and bring students back to campus safely.

Initial Design and Use of OO Platform.

Applicants created OO at Sarasota Military Academy (SMA) Prep school in 2015 as a 2-week curriculum in pandemic preparedness culminating in an experiential learning class-wide outbreak simulation. Transmission was initially mediated by stickers and other props. In 2018 Applicants introduced the OO app and platform. It includes three interconnected components (FIG. 2). The first is the mobile app for iOS and Android that uses the proximity and location-sensing capabilities of smartphones to transmit the virtual pathogen. The app currently supports the use of Bluetooth Low Energy (BLE) beacons and QR codes, which can be used to represent zoonotic infectious sources, protective items (such as facemasks and hazmat suits), and other interventions that affect pathogen transmission (vaccines or therapies). The second is an administrator website that enables organizers of outbreak simulations to enter the parameters of each simulation (e.g., number of participants, duration, pathogen, clinical symptoms, outcomes). The third is an interactive web dashboard that retrieves data from a simulated outbreak (such as number of cases, transmission events, participant health status) to allow visualizing the data, conducting calculations to determine epidemiological parameters, and other activities that develop skills in data handling and modeling. The dashboard allows for downloading the data so users can plan computational analyses using the tools that best match the needs and levels of participants.

Figure 12:
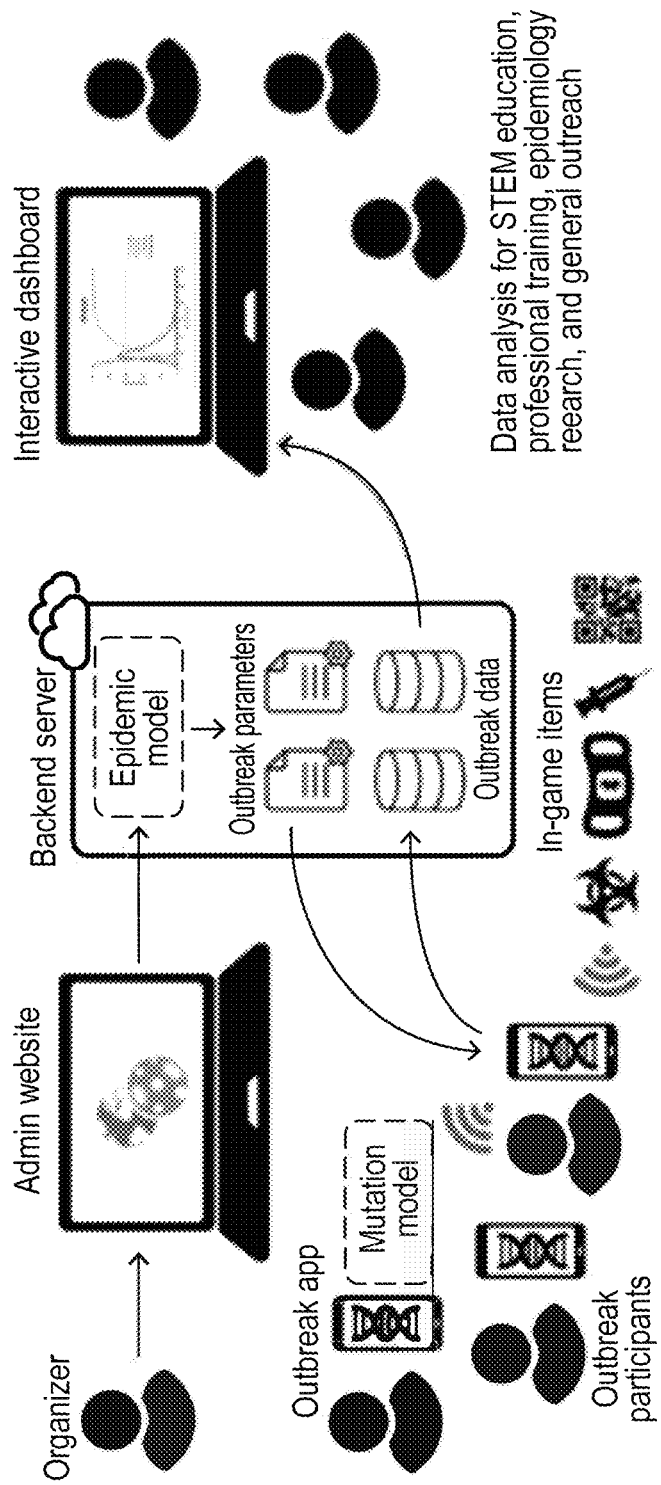
FIG. 12 is an illustration of the components in the OO platform.

In FIG. 12, the components in the OO platform are illustrated.

Our OO app-based simulations at SMA have involved more than 180 eighth-grade students who took on roles as general population, health care workers, epidemiologists, and government officials as they tried to prevent the virtual pathogen from infecting more than a predetermined fraction of the players in order to "win the game." (FIG. 1) During these simulations, Applicants have sought to strike a balance between achieving a realistic outbreak scenario and providing an engaging learning experience for middle schoolers.

OO allows parameters to be adjusted in order to run different outbreak scenarios with existing pathogens, novel pathogens based on real microbes, or even fictional diseases. For the first simulation using the app in 2018, Applicants chose Ebola virus as the pathogen, and set the app's parameters—such as symptoms and case fatality rate—accordingly. In 2019, given reported risks of emerging respiratory viruses (Li 2005, Woo 2009, Afelt 2018, Cui 2019), Applicants simulated a coronavirus modeling the reproductive number, 2-3 range, (Lipsitch 2009) of SARS and the clinical symptoms of MERS (Assiri 2013). Applicants made one key addition, a substantial period of asymptomatic transmission (twice the duration of the symptomatic period), to allow the virus to spread widely at the beginning of the game.

In early December 2019, Applicants ran simulations with the SARS-like virus at SMAPrep for 185 students, and at the Broad Institute's annual retreat, with 100 people participating. Applicants ran a simulation with the same settings at the Florida Undergraduate Research Conference (FURC) in February 2020; 260 of the 590 attendees installed the app to run an unsupervised simulation during the entire conference day, from 7 am to 5 pm.

These simulations were able to reflect the epidemiology of real infectious disease outbreaks thanks to the use of mobile technology. The OO app accurately models transmission of an airborne disease because of its ability to keep track of Bluetooth-mediated contacts between users in real time. The app triggers infection and recovery events using probabilities that can be fine-tuned to represent various diseases, and offers virtually endless possibilities to incorporate additional elements such as protective items (face masks, hazmat suits), false positive cases, multiple pathogen strains, and pathogen mutation and evolution.

Realistic Outbreak Scenarios Predict Population Behavior and Increase Engagement Over the years, Applicants have seen remarkable social and behavioral parallels between our simulated outbreaks and the COVID-19 pandemic. Notably, our OO simulations have repeatedly foreshadowed the political distrust and eruptive police altercations that have characterized the experience of COVID-19 in the US. For example, one year, students playing the role of "government officials" in OO tried to spread disinformation in order to manipulate behaviors. This strategy backfired when the "media team" discovered the truth and informed the general population. "Citizens" who had previously complied with "government" orders immediately broke quarantine and reentered the population, driving further spread of the virus. Another "government" decision that drew widespread criticism and backlash was their refusal to adequately "fund" their own epidemiology team; similar arguments have been made about fiscal allocations on both the city and federal levels in the US.

Our OO simulations have vividly illustrated the fact that viral outbreaks expose existing rifts in society, and can lead to violence and exacerbation of inequality. In one simulation, a member of the student "police" team was approached by a classmate who refused to comply with orders to confirm his infection status (as indicated on the app) the officer shot the student (with a NERF gun) for non-compliance. Applicants have also consistently observed that student "family units" with relatively few in-game "credits" (simulated money) to spend are more likely to be infected and die than their "richer" counterparts. This is likely due to the fact that they spend most of their tokens on periodic "food distribution", and have little left over to purchase personal protective equipment.

Applicants have simulated and modeled many of the response initiatives currently being considered for COVID-19, such as the widespread distribution of face masks, PPE, and even a vaccine. While the introduction and distribution of such supplies initially caused disruption in the simulation—much like the hoarding of toilet paper, disinfectant, and medical-grade masks at the beginning of the COVID-19 pandemic—all three measures appeared to reduce infection and spread of the simulated pathogen, especially when given to highly-vulnerable participants (i.e., those playing healthcare workers).

Students themselves have also proved to be an organic test of other proposed initiatives. For example, in each simulation, they have implemented and maintained social distancing of their own accord. In one recent simulation, they devised a way to photograph and share quiz questions online so that family units could earn tokens without interacting physically— a similar arrangement to the rise of remote work. They also developed a method of assessing the health status of players and limiting movements accordingly—a close model for the real-world use of health/immunity passports and containment strategies. However as trust in the government eroded, some students began to evade the system, faking their health status screenshots (FT).

Realistic simulated outbreak scenarios can provide valuable insights into how populations behave during outbreaks, and can lead to better learning outcomes (Freeman 2014). Our preliminary data—Applicants were just beginning our systematic pedagogical research when COVID-19 began—suggest that the realism and hands-on experience of the OO simulations engages students of all backgrounds. Initial student interest in taking part in OO at SMA was nominal, but it increased dramatically with the introduction of the OO app. Applicants observed higher unit test score results relative to other units at SMA, seen across all genders and races. 00 was the most anticipated lesson of the year by all classes in any subject in the school for the third straight year, based on survey results and parent reports. Applicants found that students were eager to play the roles of epidemiologists and triage workers. In the last two years, 70 of 185 students signed up for this role; over half were female and 30% were underrepresented minorities (Hispanic or Black).

The Role of Simulation and the Use of OO in Outbreak Modeling.

Realistic simulated outbreak scenarios can also help address key challenges inherent in modeling outbreaks (Cremin 2018). Indeed, epidemiologists often "replay" real outbreaks and explore alternative trajectories through simulation (Huang 2010), so as to measure the effect of changing parameters (such as the infectious rate and reproductive number, or R0), as well as the impact of containment and prevention measures (such as social isolation and vaccination).

Modeling approaches that use real-world data inadequately capture two key categories of information: the "ground truth" of transmission (i.e., every single event), and the ways that people's behaviors may change as an outbreak spreads and interventions are introduced (Fuller 2020). In contrast, simulations in which participants "play" as susceptible individuals, index cases, or super-spreaders can be highly accurate in generating and capturing both transmission data and emergent behavioral factors (Balicer 2007).

The OO app, for instance, produces anonymous contact tracing data in real time using Bluetooth, including who infects whom and when, and the subsequent series of events for each participant, ending in "recovery" or "death." This data reflects the spread of the virtual pathogen among the participants with a granularity that is nearly impossible to replicate the real world—and it can be used like real outbreak data for epidemiological modeling and visualization.

FIG. 3A shows the curve of new cases corresponding to our SMA 2018 simulation of Ebola. In order to infer the epidemiological parameters of the outbreak, Applicants applied maximum likelihood estimation (MLE) on a stochastic Susceptible-Infected-Recovered (SIR) compartmental model (King 2016) where Applicants accounted for behavioral changes among the students by allowing the transmission rate to vary over time as result of social avoidance. The ground truth of the outbreak dynamics specified in the app's parameters included a transmission probability of 0.15/minute and an infectious time of 20 minutes. Among the estimated parameters, Applicants set the basic reproduction number of the outbreak to be 3.6, with an initial contact rate of 1.4 and an infectious time of 17 minutes. The transmission rate started to decrease at around 17 minutes into the simulation, which corresponded to the appearance of the first cases. It halved 13 minutes after the decrease began; this meant that the effective reproduction number was approximately 1.8 at minute 30 of the simulation. This shows how the social avoidance behaviour by the students resulted in fewer contagions as the simulation progressed, indicative of their engagement with the learning activity.

Figure 13:
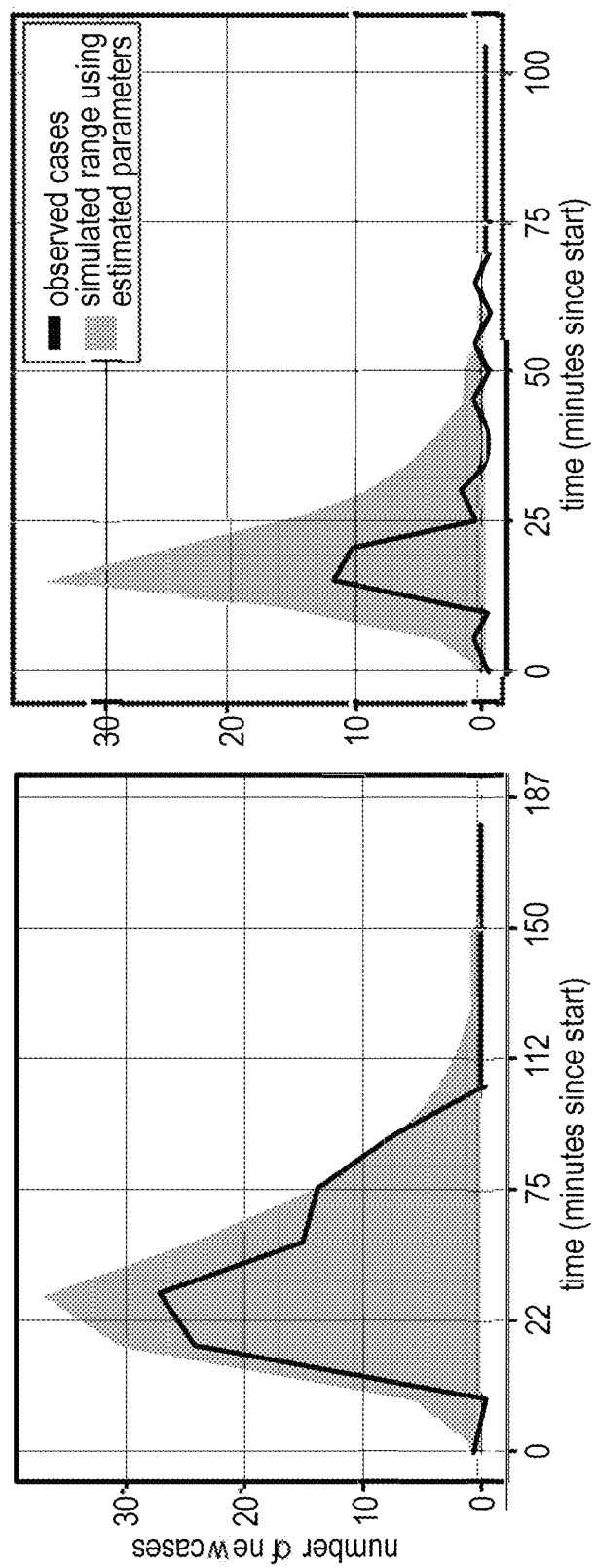
FIG. 13 is an illustration of new case counts (red line) and case 95% percentile range (blue area) from the curves simulated with the parameters estimated from the SMAPrep data produced by the OO app.

In FIG. 13, new case counts (red line) and case 95% percentile range (blue area) from the curves simulated with the parameters estimated from the SMAPrep data produced by the OO app. Panel A (left): Ebola 2018 simulation. Panel B (right): SARS-like 2019 simulation.

The SARS-like SMA simulation of 2019 yielded additional data, including information about transmission chains, thanks to data-recording improvements in the app (FIG. 4). Even though it was a different cohort from those who participated in previous years, this new group already had some expectations about the exercise and the app. This is demonstrated through application of MLE, which yielded an estimate of 3.6 for the reproductive number—exactly the same as in 2018. This match is reasonable, as the probability of infection per unit of time in the app was calculated so that the outbreak would peak at around 30 minutes into the simulation (ensuring that the students did not lose interest in the activity and it remained within a two-hour limit set by the school). However, the transmission rate decreased much faster than in the previous year—it halved in only one minute (FIG. 3B). This suggests that even passing familiarity with response and containment initiatives can yield substantial gains in containment.

More detailed data from this simulation allowed us to reconstruct the transmission chains over time and identify important features of the outbreak, such as the existence of two super-spreaders causing 4 and 5 secondary infections each that occurred early on in the game (FIG. 4B). This example shows that super-spreader events can account for a significant fraction of cases (here, 30% of all secondary infections were caused by these two individuals), as with COVID-19.

Figure 14:
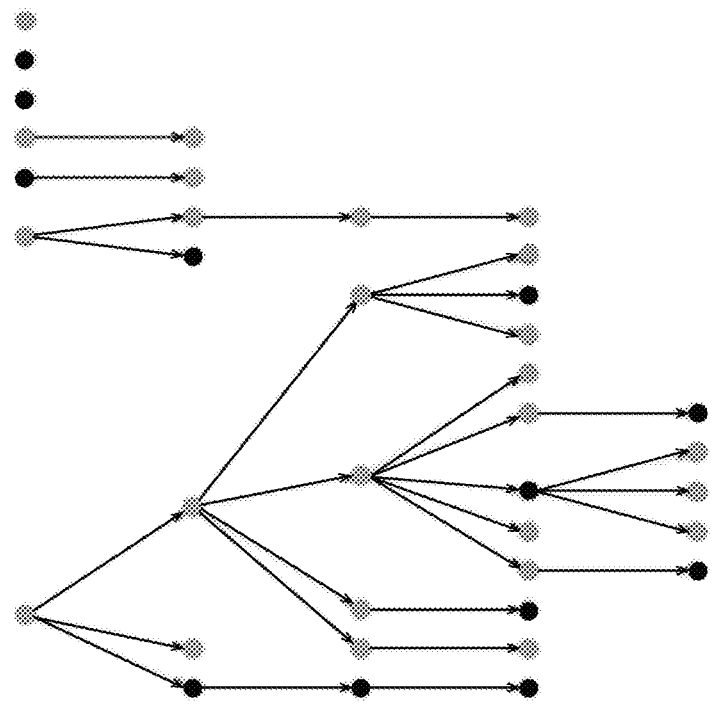
FIG. 14 is an illustration of transmission networks during the SARS simulation at SMAPrep in 2019.
Figure 14:
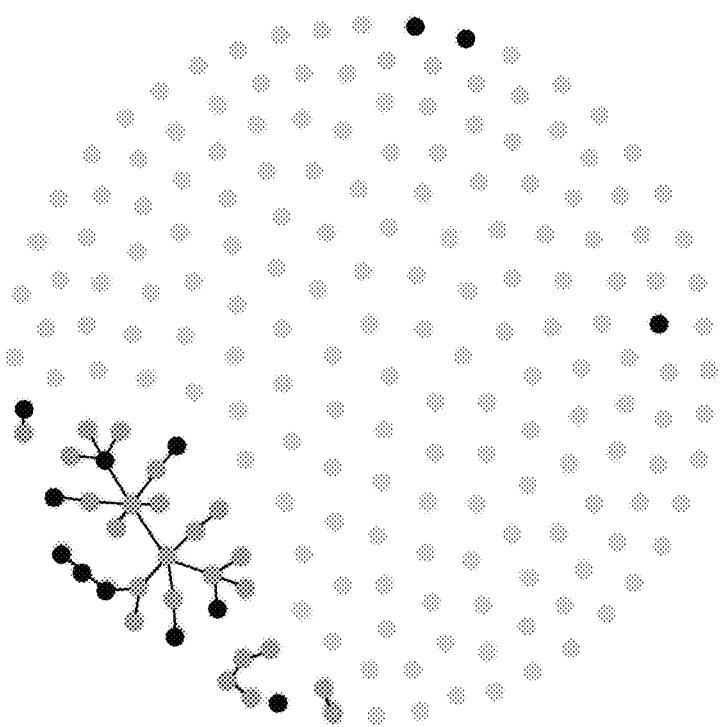

FIG. 14 illustrates transmission networks during the SARS simulation at SMAPrep in 2019. Panel A (left) shows the infected cases (red=deceased, blue=recovered) as a subset of all the participants (yellow=susceptible), with the arrows indicating transmission. Panel B (right) shows the tree diagram including only the positive cases in chronological order from top to bottom. There were two super-spreaders that caused 4 and 5 secondary infections.

For the most recent simulation, which took place at FURC and used SARS-like parameters, the curve of new cases can be seen in FIG. 5A. Applicants observed a number of peaks throughout the day, but never the exponential growth that would be expected in an entirely susceptible population. This makes sense: only 40% of the attendees installed the app, so susceptible players were buffered from each other by non-participants. This is akin to herd immunity from vaccination or individuals with immunity in the general population.

The FURC data was particularly revelatory when paired with the conference program (provided by the organizers), which entailed a series of activities that likely required students to be in close proximity to each other: two presentation sessions (posters and oral), a workshop session, and lunch. Calculation of the effective reproductive number as a function of time, Rt (FIG. 5B) shows a close match of the peaks in Rt with the occurrence of these events, with the largest increase of cases during lunchtime. Overall, Rt remained below 2, which is consistent with a population with significant herd immunity.

Figure 15:
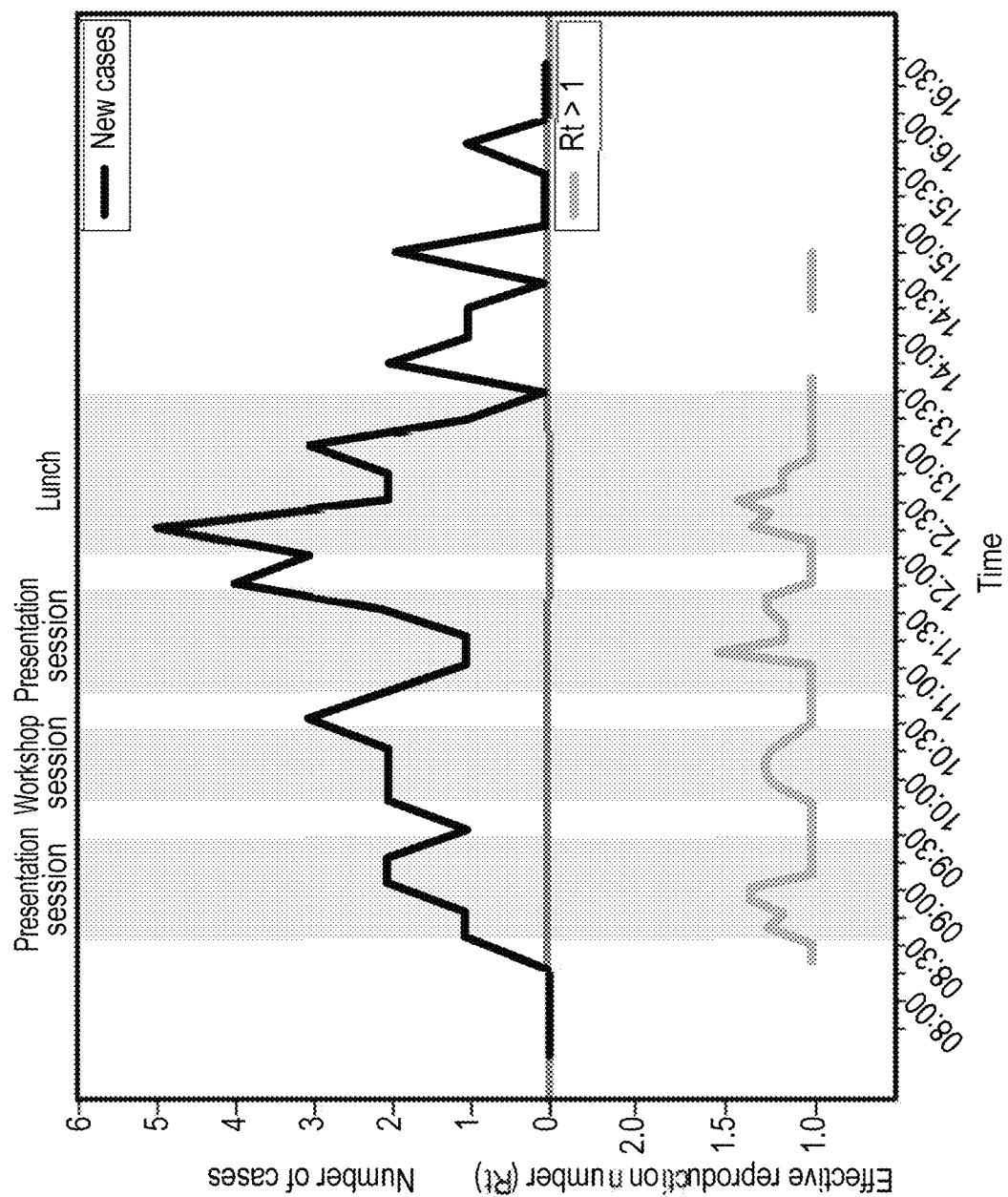
FIG. 15 is an illustration of a SARS simulation at FURC on Feb. 22, 2020.

In FIG. 15, SARS simulation at FURC on Feb. 22, 2020 is illustrated. The top curve shows the number of new cases throughout the day of the event, the bottom curve shows the effective reproductive number Rt of the simulated outbreak (when Rt is greater or equal than 1).

Through utilization of the same app in diverse scenarios, Applicants were able to model the spread of a pathogen through two very different contexts: one in a population exposed to a novel pathogen (SMA) and another for which there is an available and widely-utilized vaccine or herd immunity (FURC). At SMA every person that the students came into contact with had transmissible potential and was actively playing. The students had a mission to contain the virus and worked to maintain social distancing, determine infectious status, and reduce likelihood of transmission. This simulates the spread of a novel pathogen after the successful implementation of public health measures (such as social distancing), much like the current state of the COVID-19 response in some regions and countries. The FURC cohort, on the other hand, both had a significant number of "immune" citizens, individuals not playing, and those involved were not aiming to actively stop the outbreak from spreading, akin to silent viral spreads in populations with significant herd immunity.

A Roadmap for the Near Future: Infectious Disease Education, Outbreak Preparedness and Data Generation.

Unprecedented times yield unprecedented opportunity. Applicants have the unique chance to capitalize on the interest and momentum provided by the current pandemic by deeply engaging students as key stakeholders in ways that can help bring them back to classrooms.

Applicants envision OO as playing two key roles in the return of in-person education: as a pedagogical platform, and as a novel system for data generation and epidemiological modeling of outbreaks. The examples presented here suggest that the OO mobile app and data analytics can be applied to better understand social/psychological responses to a dangerous pathogen. They also show that OO simulations are able to produce realistic datasets and models that in turn can be used to develop and test tools for real-world settings.

Applicants are enhancing OO to include components informed by and focused on SARS-CoV-2 and increase its realism. These include the addition of a "health score" that aggregates physical movement (measured by a step counter or changes in GPS location) and social interactions (counting contact events with Bluetooth), and infectious disease knowledge (quantified by periodically quizzing users about pathogen biology, disease prevention, and outbreak response). This score will influence the probabilities of infection and recovery of each user based on his or her behaviors and responses during the simulation—effectively introducing a gamification element to incentivize behaviors and responses that are beneficial during a real-life pandemic. The scenario will be available for any user of the app, so that students involved in online learning programs around the country can play with family members at home to experience the spread of a disease in close quarters.

Additional OO add-ons will allow for simulating changes in pathogen genetics in order to provide a comprehensive teaching experience for advanced genetic epidemiology courses, as well as to generate more realistic data on pathogen transmission and evolution. These simulated data can help evaluate new methods in genetic epidemiology (Grubaugh 2019). Some of these methods are capable of inferring transmission networks and phylogenetic trees from pathogen genome sequences (Klinkenberg 2017, Kosakovsky 2018, Wohl 2020). However, their performance is difficult to evaluate without knowing the ground truth of the outbreak under study. Partially-observed transmissions, underreporting of confirmed cases, within-host pathogen dynamics, and mutations in the genome of the pathogen are sources of uncertainty in the reconstructed real-world networks and phylogenies. Simulations can provide the ground truth needed to validate these methods before applying them to real—but incomplete—data.

Applicants intend to design a version of OO that can be played as an add-on to multiplayer online games. In this, Applicants were inspired by the so-called "Corrupted Blood Incident", a virtual—and unintended—pandemic in the World of Warcraft (WoW) game that took place in 2005 due to an error in the game's code. Epidemiologists later found many correlations between users' reactions to the virtual pandemic and documented historical responses to real outbreaks (Balicer 2007). Parallels included failed attempts at quarantine and a high potential for rapid global spread (through teleportation in the game). Additionally, some WoW players put themselves at risk by healing weaker allies (mirroring health care workers in the real world), while others purposely infected as many players as possible, capturing the real-life behavior of individuals who blatantly flout public health guidance or behave irrationally, erratically, and even reprehensibly in a life-threatening outbreak (WHDH, The Guardian, Washington Post, Reuters, CNN, 9 News). Corrupted Blood showed that a virtual outbreak could recapitulate reality closely—a lesson Applicants have learned time and again with OO.

Finally, Applicants note that the COVID-19 pandemic has brought significant attention to the possibility of using app-based contact tracing and other disease surveillance technologies to contain a real outbreak, yet still with contested effectiveness (Nature op-ed, Ada Lovelace Institute) and potential for misuse (STAT op-ed, NYTimes). Applicants have been pursuing the use of Bluetooth, GPS location and other technologies for several years to help diagnose infections and track outbreaks in the real world and conversely to educate through simulations. With OO, Applicants see the possibility to understand the interplay between new technology-based public health interventions and psychological and social factors, under different scenarios of user adoption, quarantine compliance, and delays in diagnostics, in a low-stakes and safe environment. More generally, OO provides a model on how digital platforms built upon smartphone apps and mobile sensing can engage citizens of all ages into meaningful learning experiences and enable scientists to study complex processes where human behaviors play a determining role.

Applicants began working on OO in 2015 with a strong focus on education. The ongoing COVID-19 pandemic has brought initiatives such as ours to the forefront and highlighted their additional utility as preparation and response tools. It is not yet clear which interventions will best bring COVID-19 under control, but as weeks and months go by, time is wasted and lives are lost. OO can play an important role in the safe transition from strict lockdowns to social and economic reopening and the prevention of future outbreaks, provided that all of us—students and adults alike—learn the right lessons.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

Example 4—a Combining Genomics and Epidemiology to Track Mumps Virus Transmission in the United States Unusually large outbreaks of mumps across the United States in 2016 and 2017 raised questions about the extent of mumps circulation and the relationship between these and prior outbreaks. Applicants paired epidemiological data from public health investigations with analysis of mumps virus whole genome sequences from 201 infected individuals, focusing on Massachusetts university communities. Our analysis suggests continuous, undetected circulation of mumps locally and nationally, including multiple independent introductions into Massachusetts and into individual communities. Despite the presence of these multiple mumps virus lineages, the genomic data show that one lineage has dominated in the US since at least 2006. Widespread transmission was surprising given high vaccination rates, but Applicants found no genetic evidence that variants arising during this outbreak contributed to vaccine escape. Viral genomic data allowed us to reconstruct mumps transmission links not evident from epidemiological data or standard single-gene PLOS Biology surveillance efforts and also revealed connections between apparently unrelated mumps outbreaks.

Figure 16:
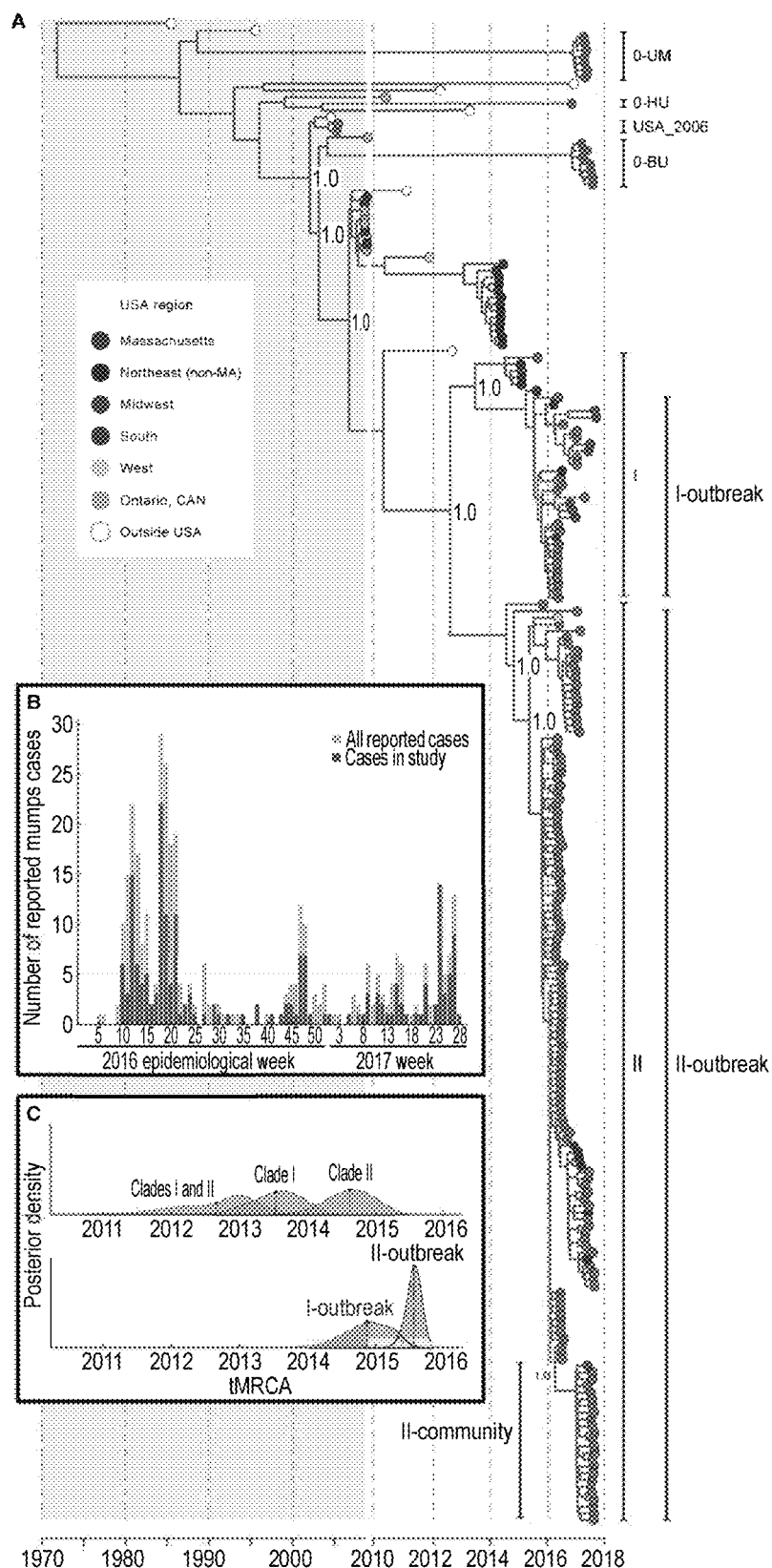
FIG. 16 is an illustration of a Massachusetts mumps outbreak overview.

FIG. 16 illustrates a Massachusetts mumps outbreak overview. (A) Maximum clade credibility tree of 225 mumps virus genotype G whole genome sequences, including 200 generated in this study. Labels on internal nodes indicate posterior support. Clades I and II contain 91% of the samples from the 2016 and 2017 Massachusetts (MA) outbreak; I-outbreak and IIoutbreak are the largest clades within them that contain only samples from the outbreak. Clade 0-UM contains samples associated with UMass other than those in Clades I and II; the same is true for 0-BU (BU) and 0-HU (Harvard). II-community contains primarily samples associated with a local Massachusetts community. (B) Number of reported mumps cases in 2016 by epidemiological week in Massachusetts (gray) and in this study (blue). (C) Probability distributions for the date of the most recent common ancestor (computed from tMRCA) of selected clades (see S2 Table for additional clades). Dotted line is the mean of each distribution. BU, Boston University; HU, Harvard Univeristy; tMRCA, time to the most recent common ancestor; UM, University of Massachusetts Amherst; UMass, University of Massachusetts Amherst.

INTRODUCTION

An unusually large number of mumps cases were reported in the United States in 2016 and017, despite high rates of vaccination [1,2]. In the prevaccination era, mumps was a routine childhood disease, with over 150,000 cases reported in the US annually [1]. After the mumps vaccine was introduced in 1967, mumps incidence declined by more than 99% [1]. Case counts rose again briefly in the mid-1980s and then continued to decrease after a national outbreak of measles prompted the recommendation of 2 Measles-Mumps-Rubella (MMR) vaccine doses in 1989 [3]. In the early 2000s, only a few hundred cases of mumps were reported annually in the US [1], attesting to the success of vaccination, possibly combined with decreasing clinical suspicion. This apparently low nationwide incidence was interrupted by an outbreak of >5,000 cases in the Midwestern US in 2006 [4], followed by a period of low incidence with minor outbreaks until 2016. This recent resurgence in mumps is partially explained by waning vaccine-induced immunity [5], but the extent to which genetic changes in circulating viruses have contributed is not yet clear. In Massachusetts, over 250 cases were reported in 2016 and over 170 in 2017, far exceeding the usual state incidence of <10 cases per year [6]. As seen in other recent outbreaks, most cases were associated with academic institutions [4] and other close-contact settings, including prisons [7] and tightly-knit ethnic and religious communities [8,9]. Mumps was reported to the Massachusetts Department of Public Health (MDPH) by 18 colleges and universities in the state, including Harvard University (Harvard), University of Massachusetts Amherst (UMass), and Boston University (BU)—the 3 institutions with the largest numbers of reported cases. Of the individuals infected, 65% had the recommended 2 doses of the MMR vaccine (S1 Table). Applicants used whole genome sequencing, phylogenetic analysis, and transmission reconstruction to investigate the spread of mumps at multiple geographic scales, including within a college campus, more widely in Massachusetts, and across the US. Pathogen sequence data have become an important tool for understanding the spread of infectious diseases in near real time, allowing researchers to pinpoint outbreak origins [10,11], resolve transmission patterns [12], and detect changes throughout the genome that could affect disease severity or the effectiveness of vaccines and diagnostics [13-16]. Such data have been shown to be most useful when analyzed alongside epidemiological data [12,17,18], although the field is still exploring in detail how genomics can contribute to understanding and controlling outbreaks [19]. Mumps outbreaks in 2016 and 2017 in the US, particularly those in universities, provided an opportunity to apply these ideas to the mumps virus and to further this exploration in the context of a closely monitored, largely self-contained campus setting.

Results and Discussion

Applicants generated 203 whole mumps virus genomes from buccal swabs from patients who tested positive by polymerase chain reaction (PCR) for mumps virus (FIG. 1A), of which 158 werefrom Massachusetts during the 2016 and 2017 outbreak (FIG. 1B), with 92 from Harvard, BU, or UMass in particular. The remaining 43 genomes were from 15 other states, collected between 2014 and 2017 (Table 1). These 203 genomes come from 259 PCR-positive samples, 56 of which were excluded because they did not produce data that met our definition of a complete genome (see Materials and methods) because of low viral loads, often caused by collecting the samples too late in the course of infection (S1A and S1B Fig). These 56 samples that did not produce genomes were well distributed across the 2016 through 2017 study period and showed no geographic clustering (Massachusetts versus elsewhere). The median sequencing depth of the 203 successful genomes was 176x (first quintile: 42.4x; fourth quintile: 651.8x; S1C Fig) and all were >82% complete (182 genomes were >99% complete). These full genomes provide substantially more data than sequences of the small hydrophobic (SH) gene alone (accounting for <3% of the genome), which is conventionally used for classifying mumps virus [20,21]. For the Massachusetts samples, epidemiological data (including university affiliation and vaccination status) and contact tracing data collected by the MDPH and local universities were also available (S1 Table; see S1 Data for full line list). Applicants note that 2 of the individuals in the Massachusetts data set had paired samples from 2 timepoints; in both cases, Applicants excluded the genome from the later sample in subsequent analyses, leaving 201 genomes from unique patients. Of these 201 individuals from Massachusetts, 72% had known vaccination status, of whom 93% had 1 or more MMR doses. Applicants also sequenced 29 PCR-negative samples from suspected mumps cases; in only one was there limited evidence for mumps virus, but Applicants did identify 4 other viruses (one in each of 4 of these samples; S3 Table), 2 of which are known to cause parotitis [22], a characteristic symptom of mumps [23]. The viral whole genome data led to 2 key findings about the origin and spread of the recent outbreaks. First, our analysis revealed that the outbreaks—in Massachusetts and also more broadly in the US—were largely the product of a single mumps lineage and that this lineage was responsible for most if not all US mumps outbreaks since at least 2006. This lineage belongs to mumps virus genotype G [20,21] as do all but 1 of the 201 genomes from unique patients in our data set. Unless otherwise stated, all subsequent analyses refer only to these 200 genotype G genomes (Table 1). Phylogenetic analysis of these 200 genomes, along with the other 25 publicly available genotype G genomes, shows that almost all (192 of the 200 samples in our data set; 211 of the 225 total) belong to a single lineage within genotype G, despite having been collected from all over the country (FIG. 1A; also supported by a principal component analysis; see S2 Fig). This lineage descends from the US mumps outbreak in 2006. Single-gene data (see discussion of SH gene below) show no evidence for extensive transmission of this lineage outside the US, suggesting that most mumps cases in the US since 2006 are the result of ongoing transmission of a single lineage within the United States; specifically, this connects previously unassociated cases (with published genomes) between 2006 and 2016 [1,8,24]. This also suggests that unreported infections may be common and may be driving ongoing transmission [23,25].

TABLE 1

Summary of samples and genomes. Counts of samples sequenced and genomes generated by source (MDPH or CDC), date, and mumps virus PCR result. [G] indicates genotype G genomes. Two genomes are from a second sample of a patient already included in the data set.

| Source | Dates | PCR result | Samples | Genomes | Genomes (unique patients) | Genomes [G] (unique patients) |
|---|---|---|---|---|---|---|
| CDC | 2014-2015 | + | 26 | 18 | 18 | 18 |
| CDC | 2016-2017 | + | 33 | 25 | 25 | 25 |
| MDPH | 2014-2015 | + | 6 | 2 | 2 | 2 |
| MDPH | 2016-2017 | + | 194 | 158 | 156 | 155 |
| MDPH | 2016-2017 | − | 29 | 0 | 0 | 0 |
| | | Total | 288 | 203 | 201 | 200 |

Abbreviations:
CDC, US Centers for Disease Control and Prevention;
MDPH, Massachusetts Department of Public Health;
PCR, polymerase chain reaction
https://doi.org/10.1371journal.poo.3000611.t001

The distribution of cases within the phylogenetic tree further suggests geographic movement of mumps virus on short time scales. For example, clade I (FIG. 1A) contains virus genomes collected in 2015 through 2017 from Massachusetts, from elsewhere in the Northeast, from the South, and from the Midwest. The date of the most recent common ancestor of this clade was most likely in 2013 or later (FIG. 1C and S3 Table), which implies that the virus spread to all of those regions in less than 5 years. Similarly, clade II contains genomes from all of those regions as well as one from the western US, all collected during the same time period. Clade II likely dates from no earlier than 2014, suggesting spread to these regions occurred in an even shorter amount of time. Together, these observations provide strong evidence for regional circulation in the Northeast, coupled with at least occasional movement to more distant geographic regions. Further sampling of these other regions may reveal additional long-distance dispersal events, which would indicate widespread geographic movement of mumps. This would not be surprising if transmission frequently occurs through college students, many of whom reside in close-contact settings and also travel long distances to return home.

The second key finding about the recent spread of mumps virus relates to its origins in Massachusetts. Although this 2006 lineage dominated the Massachusetts outbreak, the outbreak was not caused by a single introduction of mumps virus into the state but rather is comprised of at least 6 distinct viral clades (FIG. 1A). Several of these were sublineages of the dominant 2006 lineage, including the 2 largest, Clades I and II, which comprise more than 90% of samples from Massachusetts (13% and 77%, respectively). These 2 clades diverged before the 2016 outbreak began (FIG. 1C and S2 Table), indicating that they independently contributed to it. The remaining 4 clades (0-UM, 0-HU, 0-BU, plus one genotype K genome) likewise represent independent introductions, one of which (0-BU) also falls within the 2006 lineage. Such multiple introductions, indicating widespread transmission of mumps virus, have been observed elsewhere in the US [25] and are also seen in this data set within individual universities: samples from UMass span 2 clades (II and 0-UM), Harvard samples span 3 clades (I, II, and 0-HU), and BU samples span 3 clades (I, II, 0-BU) (S3 Fig). This emerging pattern of complexity, which has only become apparent with viral genomic data, provides a previously inaccessible look into the degree to which mumps is moving within and between states and communities in the US. Epidemiological investigation showed that each of the 4 minor clades described above contains at least one sample from a patient with foreign travel history during the incubation period of the virus (12-25 days before symptom onset [26]; S1 Data). Together, the genomic and epidemiological data suggest that most mumps virus cases in the US belong to the primary 2006 lineage but that small clusters of cases can be attributed to repeated importation of the virus from outside the country. These imported cases do not appear to be important contributors to the overall burden of mumps in the US.

The finding that a single mumps lineage has been successful in a highly vaccinated population [2], despite repeated introductions of other lineages, raised the possibility that mutations within this lineage have contributed to its success, perhaps by enabling vaccine escape. Because mutations contributing to the success of the entire lineage necessarily occurred early in the evolution of that lineage, Applicants note here the differences between fixed mutations in our data set and the strain used in the mumps vaccine. Applicants found that there were numerous fixed differences between samples from the 2016 outbreak and the Jeryl Lynn vaccine strain in regions of immunological significance (S4A Fig and S1 Text), consistent with a recent similar analysis [27]. In the hemagglutinin-neuraminidase (HN) protein, the primary target of neutralizing antibodies [28], Applicants observed 32 sites with fixed amino acid substitutions between our sequences and the Jeryl Lynn strain. Thirty of these sites were conserved between our sequences and a cell-passaged clinical strain that was isolated from Iowa in 2006 (accession: JX287385), near the beginning of mumps resurgence in the US. The Iowa 2006 strain was previously shown to be neutralized by sera from both vaccinated.

and naturally infected individuals, but to a lower degree than neutralization of the Jeryl Lynn strain itself [29-31], raising the possibility that some of these mutations may confer partly reduced neutralization susceptibility. In addition, Applicants observed 2 positions at which our sequences differed from both the Jeryl Lynn and the Iowa 2006 strains. At these 2 positions, the variant observed in our sequences was also present in most other genotype G sequences published to date, including in sequences from a recent study from the Netherlands [28]. Further studies are warranted to test the neutralization susceptibility of strains containing these variants, because the Iowa 2006 sequence may not be fully representative of most currently circulating genotype G viruses. Applicants also looked for any evidence of ongoing adaptation to the vaccine during the outbreak. Applicants considered this as a possibility because the vaccine was introduced relatively recently in the history of the mumps virus, recently enough that the virus could still be adapting to it. Additionally, in the absence of widespread natural infection, vaccination now constitutes the largest immunological selective force on mumps virus in the US. To investigate this, Applicants paired genomic data with vaccination records to look for any evidence of changes in the mumps virus genome during the outbreak that led to antigenic variation from the Jeryl Lynn vaccine strain. Applicants first tested whether nucleotide substitutions in genomes from the Massachusetts outbreak clustered by time since vaccination, or whether vaccinated individuals clustered on certain branches of the phylogenetic tree; neither was the case (S4B and S4E Fig). Second, Applicants looked for signals of positive selection (using the dN/dS statistic) in the 225 genotype G genomes in our data set; a signal here would suggest that nonsynonymous mutations in a particular gene were being favored by ongoing selective pressure. Applicants found no evidence for selection in any gene or at any specific site (S4C and S4D Fig). Thus, Applicants did not find direct evidence of genetic variants arising within this outbreak that contributed to vaccine escape, although Applicants note that both tests have quite limited statistical power in this data set. This finding is consistent with a recent study that proposed waning vaccine-induced immunity as a driving factor in recent US mumps outbreaks [5]; this hypothesis is also supported by our own data, in which Applicants find that time since vaccination differs between Massachusetts individuals testing positive and negative for mumps virus by PCR in 2016 through 2017, with longer times since vaccination observed in mumps-positive patients (S5 Fig). Understanding transmission routes can be crucial in guiding the public health response to an outbreak—for example, whether efforts should be directed toward controlling mumps spread within a university or preventing virus importation. In the Massachusetts mumps outbreak, detailed genomic data allowed us both to confirm connections suggested by public health investigation and to identify new links between cases. The phylogeny described above shows that mumps samples from different Massachusetts universities were genetically similar and fell within the 2 primary clades (S3 Fig), consistent with the epidemiological interpretation that these contemporaneous cases were part of 1 large mumps outbreak in 2016 through 2017.

It also showed an unexpected connection between mumps cases in a local, nonacademic community (Clade II-community) and those at Harvard: the II-community cases fall within the predominantly Harvard Clade II, suggesting a spillover event from the university into the wider community (FIG. 2A). Cases in these 2 clades were classified as distinct outbreaks during initial public health investigation based on epidemiological data [32], different demographic makeup of the 2 populations (older adults with no obvious university connection versus mostly college-aged students), and a 5-month gap between the last confirmed cases at Harvard and the cases in the local community. However, the genomic data clearly suggests a connection, supported by additional epidemiological investigation that identified 3 individuals affiliated with both Harvard and the local community who could have acted as transmission links.

Because of the large number of cases reported and sequenced and the contact tracing information available, Applicants were able to quantify mumps transmission dynamics within Harvard. Applicants first used an epidemiological model (S6 Fig) [5] without genomic data to estimate transmission within the university, but it did not permit us to distinguish between a single mumps introduction followed by high transmission and multiple introductions followed by low transmission (FIG. 2B left). Applicants then modified the model to incorporate the number of viral lineages (Clades 0-HU, II-community, and 2 subclades within Clade II) observed within Harvard. This markedly improved our ability to distinguish these scenarios, supporting an estimate of 5 (95% CI: 4-18) distinct introductions to Harvard and an effective reproduction number (RE) of 1.70 (95% CI: 1.50-1.91; FIG. 2B right). An RE well above 1.0 means that the outbreak could be self-sustaining, which highlights the importance of controlling on-campus transmission during mumps outbreaks.

Figure 17:
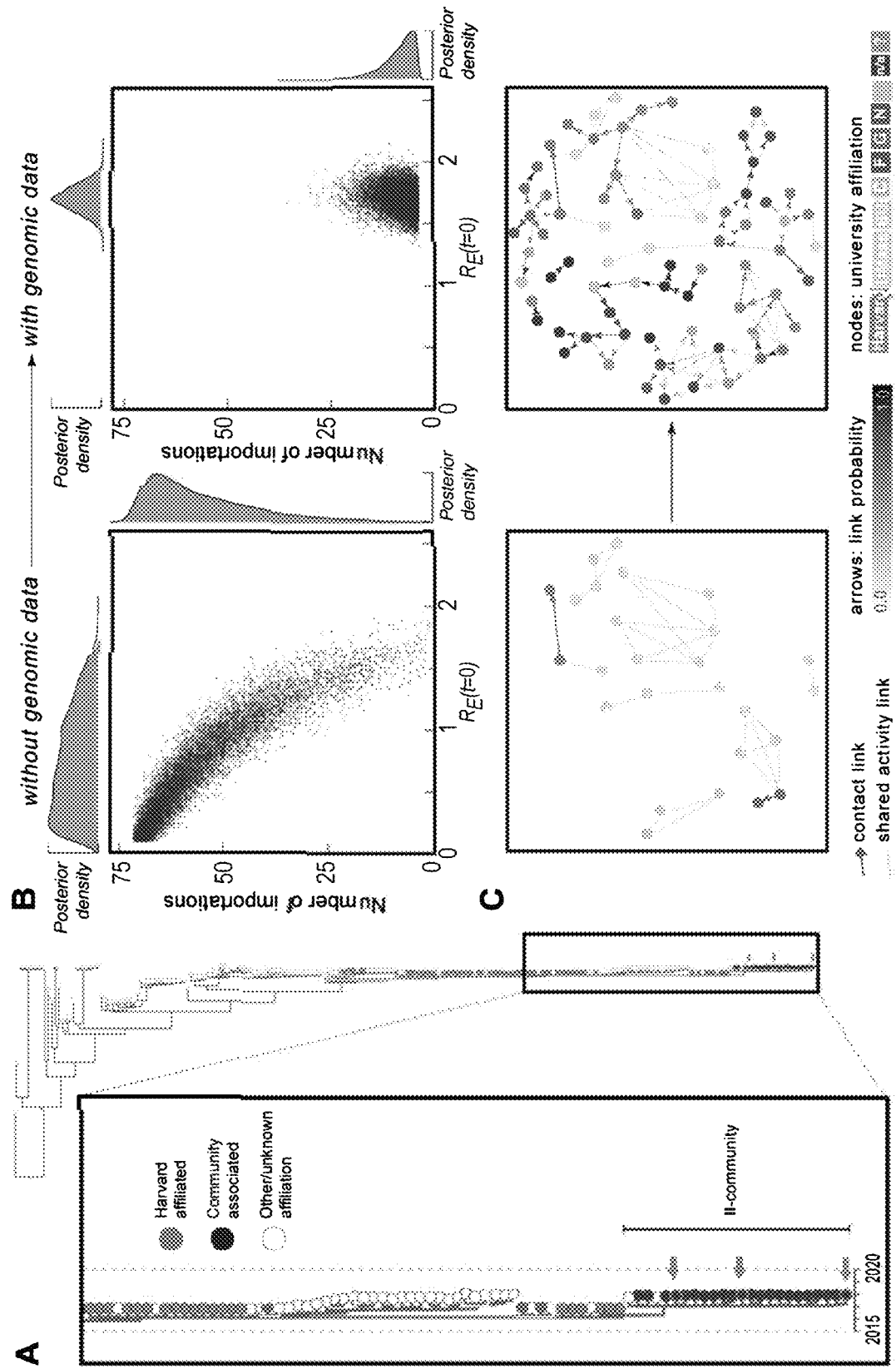
FIG. 17 is an illustration of a epidemiological modeling and transmission reconstruction.

In FIG. 17, Epidemiological modeling and transmission reconstruction are illustrated. (A) Zoom view of Clade II-community and its ancestors (see FIG. 1A). Arrows: individuals affiliated with both II-community and Harvard. (B) Number of importations into Harvard calculated without (left) and with (right) viral genetic information as input. Each point represents a sample from the posterior distribution of RE(t=0) and the number of introductions, based on simulated transmission dynamics. (C) Transmission reconstruction of individuals within Clade II-outbreak; samples are colored by institution affiliation (light purple: other institution; n/a: no affiliation; question mark: unknown affiliation). Left: reconstruction using epidemiological data only; all individuals in Clade II-outbreak with known epidemiological links (red arrows) are shown. Right: reconstruction using mumps genomes and collection dates. Arrow shading indicates probability of direct transmission between individuals (minimum probability shown: 0.3); cases with 1 or more inferred links are shown and are colored by institution. Arrows outlined in red represent transmission events identified by both genomic and epidemiological data. Faded nodes are those only connected by shared activity links (i.e., no inferred or known direct transmission). BU, Boston University; Harvard, Harvard University; RE, effective reproduction number; UMass, University of Massachusetts Amherst.

The high-resolution data from Harvard allowed us to estimate transmission links between individual cases, which can aid in targeting containment efforts aimed at high-risk individuals or groups. For this purpose, Applicants focused on Clade II-outbreak because it was largely contained within a single institution (Harvard) and had dense sampling. When Applicants attempted to link individual mumps cases within this clade using contact tracing data alone, Applicants could only infer direct mumps transmissions ("contact links") between 2 pairs of individuals (FIG. 2C left). Applicants then used the genomic data to validate genetic distance as a proxy for epidemiological linkage (S7A and S7B Fig) and, based on these results, used genomic data and sampling dates to reconstruct possible mumps transmissions. The reconstruction (FIG. 2C right, see also S7C Fig), which estimates and assigns a probability to direct transmission links, supports 1 of the 2 pairs of direct mumps transmissions as well as 2 "shared activity links" (see Materials and methods) and also suggests many new links between individuals without any known contacts. Indirect links, however, are difficult to identify using genomic data alone, illustrating the complementary contributions of genomic and epidemiological data for reconstructing detailed transmission, which can guide response efforts for mumps and other outbreaks in close-contact settings.

Figure 18:
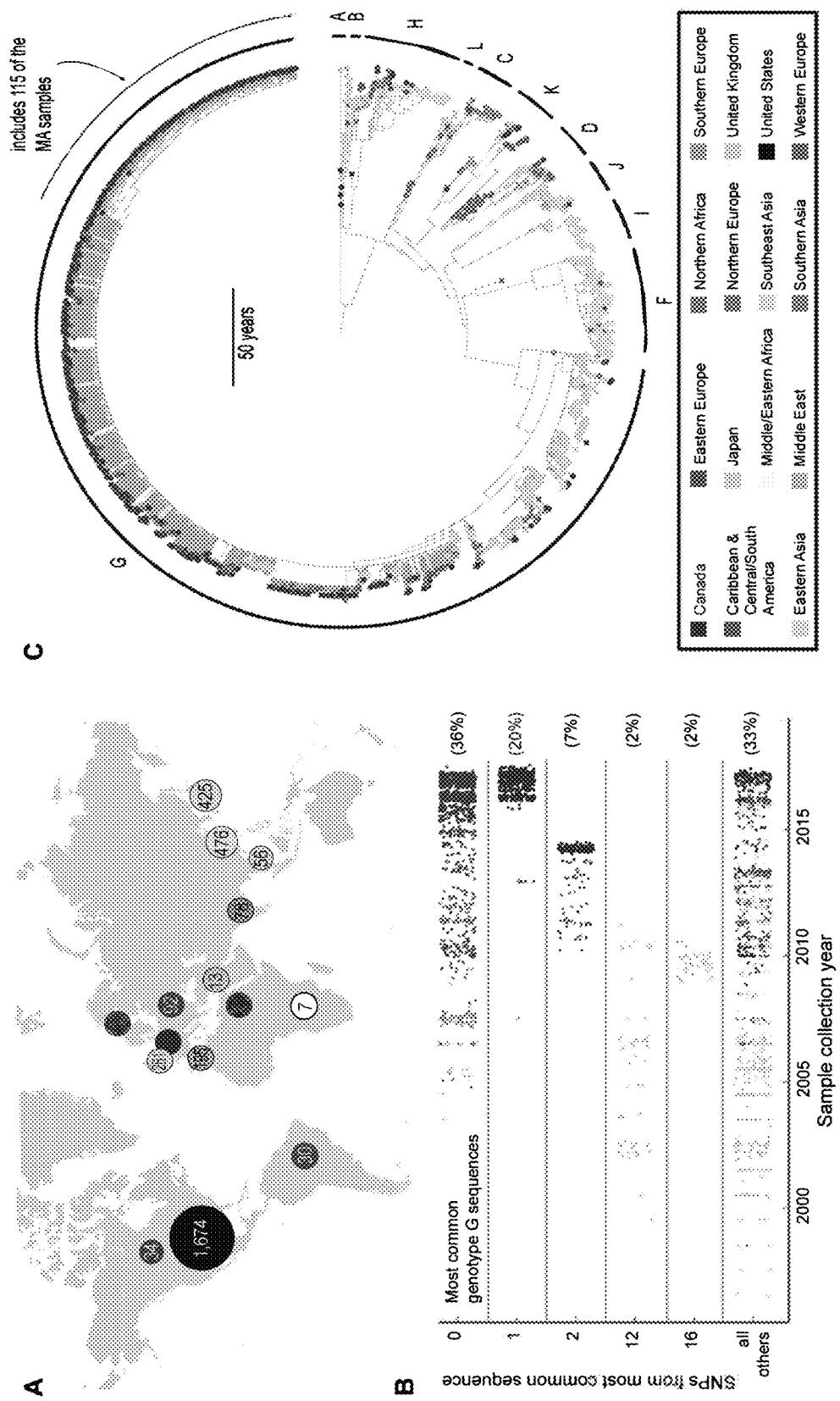
FIG. 18 is an illustration of a global spread of mumps virus based on SH gene sequences.

In FIG. 18, a global spread of mumps virus based on SH gene sequences is illustrated. Colors in all panels are by region (legend in bottom right). (A) Number of SH sequences in our data set from each of the 15 regions. (B) Identical genotype G sequences over time from 1995 through 2017. Each dot represents a sample; each row contains samples with identical SH sequences, except the bottom, which includes samples with sequences distinct from those in the above 5 categories. Numbers on the right: percentage of all genotype G samples found in that row. (C) Maximum clade credibility tree of 3,646 publicly available SH gene sequences, including 193 complete SH sequences generated in this study. SH, small hydrophobic. doi.org/10.1371/journal.pbio.3000611.g003

Conventional sequence-based mumps surveillance has been limited to the SH gene. The SH gene is a small (316-nucleotide), convenient target for sequencing [20,33] and is thus the region for which the most sequence data are available. Applicants used the 3,646 publicly available SH sequences from mumps cases around the world (FIG. 3A) to assess whether SH sequences would be adequate to distinguish the lineages and transmission patterns identified above. To do this, Applicants constructed the mumps phylogeny using the SH sequence alone and compared it to the whole genome phylogeny. There was limited variation within each genotype (genotype G shown in FIG. 3B), and neither of our main phylogenetic conclusions based on whole genome data could be ascertained from SH alone: Applicants could not determine the relationship between the spillover into the local community and its source in Harvard (other than that they belonged to the same clade), and Applicants were unable to determine the relationship between the 2016 and 2017 outbreak and the 2006 lineage (S8 Fig). Our other key findings, such as the detailed picture of transmission within Harvard and a refined RE estimate, rely on these 2 conclusions. Nevertheless, SH data were sufficient to resolve population structure on a global scale and to confirm that the 11 known clinically relevant genotypes are associated with particular world regions (FIG. 3C) [34]. Moreover, an analysis of global migration reveals significant movement of mumps virus between the US and Europe. For details on the global SH analysis, including a discussion of its limitations, see S1 Text, S9 and S10 Figs.

The combination of high-quality genomic and epidemiological data from the Massachusetts mumps outbreak revealed the extent to which mumps is circulating in the US, connected previously unrelated outbreaks, and allowed us to trace transmission within and between individual communities. Given the high-quality genomic data Applicants were able to produce from mumps clinical samples, as well as the limited information that can be gleaned from SH sequencing, it is worth considering whether future public health surveillance of mumps should incorporate whole genome sequencing. The collection of these detailed data, which Applicants have made available to the community (see Materials and methods), was only possible through extensive collaboration between state and national public health agencies, academic researchers, and affected universities throughout the greater Boston, Mass. area. Applicants hope that these partnerships, fostered in response to a surge in mumps cases in Massachusetts in 2016 and 2017, will facilitate real-time genomic and epidemiological data generation, analysis, and sharing in future outbreaks of any pathogen.

Materials and Methods

Ethics Statement

The study protocol was approved by the MDPH, Centers for Disease Control and Prevention (CDC), and Massachusetts Institute of Technology (MIT) Institutional Review Boards (IRB) (MDPH IRB 00000701, project 906066). Harvard University Faculty of Arts and Sciences and the Broad Institute ceded review of sequencing and secondary analysis to the MDPH IRB through authorization agreements. The MDPH IRB waived informed consent given this research met the requirements pursuant to 45 CFR 46.116 (d). The CDC IRB determined this project to be nonhuman subjects research as only deidentified leftover diagnostic samples were utilized. In compliance with the IRB agreement, Harvard University, University of Massachusetts Amherst, and Boston University granted approval for publication of their institution names in this paper.

Sample Collections and Study Subjects

Buccal swab samples were obtained from suspected and confirmed mumps cases tested at MDPH and CDC. Samples from MDPH ("Cases in Study," FIG. 1B) include all cases with a positive mumps PCR result (see "PCR diagnostic assays performed at MDPH and CDC" below) collected between 1 Jan. 2014 and 30 Jun. 2017. Demographic information for all cases reported in Massachusetts (FIG. 1B and Table 1) includes all confirmed and probable mumps cases reported to MDPH in that time period. Probable cases include cases with a positive mumps IgM assay result or those with an epidemiological link to a confirmed case [35]. Samples from CDC are a selection of PCR-positive cases submitted to the CDC for testing between 2014 and 2017. See S1 Data for deidentified information, including metadata, about study participants.

Viral RNA Isolation

Sample inactivation and RNA extraction were performed at the MDPH, Broad Institute, and CDC. At MDPH, viral samples were inactivated by adding 300 µL Lysis/Binding Buffer (Roche) to 200 µL sample, vortexing for 15 seconds, and incubating lysate at room temperature for 30 minutes. RNA was then extracted following the standard external lysis extraction protocol from the MagNA Pure LC Total Nucleic Acid Isolation Kit (Roche) using a final elution volume of 60 µL. At the Broad Institute, samples were inactivated by adding 252 µl, Lysis/Binding Buffer (ThermoFisher) to 100 µL sample. RNA was then extracted following the standard protocol from the MagMAX Pathogen RNA/DNA Kit (ThermoFisher) using a final elution volume of 75 µL. At CDC, RNA extraction followed the standard protocol from the QiaAmp Viral RNA mini kit (Qiagen).

PCR Diagnostic Assays Performed at MDPH and CDC

Diagnostic tests for presence of mumps virus were performed at the MDPH and CDC using the CDC Real-Time (TaqMan) RT-PCR Assay for the Detection of Mumps Virus RNA in Clinical Samples [8,36]. Each sample was run in triplicate using both the Mumps N Gene assay (MuN) and RNase P (RP) assay using this protocol. RT-PCR was performed on the Applied Biosystems 7500 Fast Real-Time PCR system or Applied Biosystems Prism 7900HT Sequence Detection System instrument.

PCR Quantification Assays Performed at Broad Institute

Mumps virus RNA was quantified at the Broad Institute using the Power SYBR Green RNA-to-Ct 1-Step qRT-PCR assay (Life Technologies) and CDC MuN primers. The 10 µL assay mix included 3 µL RNA, 0.3 µL each of mumps virus forward and reverse primers at 5 µMconcentration, 5 µL 2× Power SYBR RT-PCR Mix, and 0.08 µL 125× RT Enzyme Mix. The cycling conditions were 48° C. for 30 minutes and 95° C. for 10 minutes, followed by 45 cycles of 95° C. for 15 seconds and 60° C. for 30 seconds with a melt curve of 95° C. for 15 seconds, 55° C. for 15 seconds, and 95° C. for 15 seconds. RT-PCR was performed on the ThermoFisher QuantStudio 6 instrument. To determine viral copy number, a double-stranded gene fragment (IDT gBlock) was used as a standard. This standard is a 171 bp fragment of the mumps genome (GenBank accession: NC_002200) including the amplicon (sequence: GGA TCG ATG CTA CAG TGT ACT AAT CCA GGC TTG GGT GAT GGT CTG TAA ATG TAT GAC AGC GTA CGA CCA ACC TGC TGG ATC TGC TGA TCG GCG ATT TGC GAA ATA CCA GCA GCA AGG TCG CCT GGA AGC AAG ATA CAT GCT GCA GCC AGA AGC CCA AAG GTT GAT TCA AAC (SEQ ID NO: 1)). 23S rRNA content in samples was quantified using the same Power SYBR Green RNA-to-Ct 1-Step qRT-PCR assay kit and cycling conditions. Primers were used to amplify a 183 bp universally conserved region of the 23S rRNA (fwd: 93a—GGG TTC AGA ACG TCG TGA GA (SEQ ID NO: 2), rev: 97ar—CCC GCT TAG ATG CTT TCA GC (SEQ ID NO: 3)) [37]. To determine viral copy number, a double-stranded gene fragment (IDT gBlock) was used as a standard. This standard is a 214 bp fragment of the *Streptococcus* HTS2 genome (accession: NZ_CP016953) (sequence: AGC GGC ACG CGA GCT GGG TTC AGA ACG TCG TGA GAC AGT TCG GTC CCT ATC CGT CGC GGG CGT AGG AAA TTT GAG AGG ATC TGC TCC TAG TAC GAG AGG ACC AGA GTG GAC TTA CCG CTG GTG TAC CAG TTG TCT CGC CAG AGG CAT CGC TGG GTA GCT ATG TAG GGA AGG GAT AAA CGC TGA AAG CAT CTA AGT GTG AAA CCC ACC TCA AGA T (SEQ ID NO: 4)). Data from both assays—each performed only on a subset of samples—is reported in S1 Data.

Bacterial rRNA Depletion

Bacterial rRNA was depleted from some RNA samples (see S1 Data) using the Ribo-Zero Bacteria Kit (Illumina). At the hybridization step, the 40 µL reaction mix included 5 µL RNA sample, 4 µL Ribo-Zero Reaction Buffer, 8 µL Ribo-Zero Removal Solution, 22.5 µL water, and 0.5 µL synthetic RNA (25 fg) used to track potential cross-contamination (gift from M. Salit, NIST). Bacterial rRNA-depleted samples were purified using 1.8× volumes Agencourt RNAClean XP beads (Beckman Coulter) and eluted in 10 µL water for cDNA synthesis.

Illumina Library Construction and Sequencing cDNA synthesis was performed as described in previously published RNA-seq methods [38]. In samples in which bacterial rRNA was not depleted, 25 fg synthetic RNA was added at the beginning of cDNA synthesis to track sample cross-contamination. Positive control libraries were prepared from a mock mumps virus sample in which cultured Enders strain (ATCC VR-106) mumps was spiked into a composite buccal swab sample from healthy patients and diluted to mumps virus RT-qPCR Ct=21. This mock sample was extracted using the viral RNA isolation protocol described above, except that total nucleic acid was eluted in 100 Negative control libraries were prepared from nuclease-free water. Illumina Nextera XT was used for library preparation: indexed libraries were generated using 16 cycles of PCR, and each sample was indexed with a unique barcode. Libraries were pooled equally based on molar concentration and sequenced on the Illumina HiSeq 2500 (100 or 150 bp paired-end reads) platform.

Hybrid Capture

Viral hybrid capture was performed as previously described [38] using 2 different probe sets. In one case, probes were created to target mumps and measles virus (V-MM probe set), and in one case, probes were created to target 356 species of viruses known to infect humans (V-All probe set) [39]. Capture using V-All was used to enrich viral sequences primarily in samples in which Applicants could not detect mumps virus, as well as in other samples (see S1 Data for a list of which samples were captured using which probe set). As described in the work by Metsky and colleagues [39], the probe sets were designed to capture the diversity across all publicly available genome sequences on GenBank for these viruses. Probe sequences can be downloaded here: github.com/broadinstitute/catch/tree/cf500c69/probe-designs.

Genome Assembly

Applicants used viral-ngs version 1.18.1 [40] to assemble genomes from all sequencing runs. Viral-ngs is freely available under a BSD license (viral-ngs.readthedocs.io/en/latest/). Applicants used a set of mumps sequences (accessions: JX287389.1, FJ211586.1, AB000386.1, JF727652.1, AY685920.1, AB470486.1, GU980052.1, NC_002200.1, AF314558.1, AB823535.1, AF467767.2) to taxonomically filter these reads. Applicants de novo assembled reads and scaffolded against the mumps genome with accession JX287389.1 to assemble a genome for each replicate. Then, Applicants pooled read data from all sequencing replicates of each sample and repeated this assembly process to obtain final genomes. Each time Applicants ran viral-ngs, Applicants set the "assembly_min_length_-fraction_of reference" and "assembly_min_unambig" parameters to 0.01. Technical replicates had high concordance: in 27 samples prepared more than once, only 2 base calls differed across replicates. Applicants replaced deletions in the coding regions with ambiguity ("N"). In one sample, MuVs/Massachusetts.USA/11.16/5 [G], with an insertion at position 3,903 (based on a full 15,384-nucleotide mumps virus genome, e.g., accession JN012242.1) Applicants removed a poorly supported (<5 reads covering the site) extra "A" in a homopolymer region. To calculate sequencing metrics (S1 Fig), Applicants used SAMtools [41] to downsample raw reads for each replicate to 1 million reads and then reran assembly as described above. Samples from 1 contaminated sequencing batch were excluded, as were all replicates from PCR-negative samples. In cases in which samples from 2 time points were sequenced from a single patient, Applicants included only the first time point in the collection interval analysis (S1D Fig).

Metagenomic Analysis

Applicants used the V-All probe set for capture on all samples from suspected mumps cases with a negative mumps PCR result (n=29). A subset of PCR-positive samples was also sequenced with this probe set (n=145; without capture="unbiased," n=111). Applicants used the mock Enders strain mumps sample as a positive control on a sequencing run containing all PCR-negative samples, as well as a water sample as a negative control. Applicants used the metagenomic tool Kraken version 0.10.6 [42] via viral-ngs to identify the presence of viral taxa in each sample. Applicants built a database similar to the one described in the work by Metsky and colleagues [39], except without insect species. This database encompasses the known diversity of viruses known to infect humans. It is publicly available, in 3 parts, at storage.googleapis.com/sabeti-public/meta_dbs/kraken_full_20170522/[file], where [file] is database.idx.1z4 (595 MB), database.kdb.1z4 (75 GB), and taxonomy.tar.1z4 (66 MB). Because of the possibility of contamination, Applicants prepared a second, independent sequencing replicate on all PCR-negative samples with evidence for mumps or another virus and required both replicates to contain reads matching the virus detected in the sample. Applicants found no evidence of pathogenic viruses other than mumps in PCR-positive samples.

Applicants required the total raw read count for any genus in any sample to be twice (in practice, 7 times) that in any negative control from any sequencing batch. For any sample that had one or more pathogenic viral genera that passed this filter and had deduplicated reads well distributed across the relevant viral genome, Applicants attempted contig assembly: Applicants used viral-ngs to filter all sample reads against all NCBI GenBank [43] entries matching the identified species and then de novo assembled reads using Trinity [44] through viral-ngs and scaffolded against the closest matching full genome identified by a blastn query [45]. Applicants report all viruses identified via this method in S3 Table. In parallel, Applicants used SPAdes [46] within viral-ngs to de novo assemble contiguous sequence from all de-duplicated, depleted reads. Applicants used the metagenomic tool DIAMOND version 0.9.13 [47] with the nr database downloaded 29 May 2017, followed by blastn [45] of DIAMOND-flagged contigs. Using this method, Applicants confirmed the presence of all previously identified viruses except influenza B virus, for which Applicants never assembled a contiguous sequence. Applicants found no evidence of additional pathogenic viruses using this method.

Criteria for Pooling Across Replicates

Applicants prepared one or more sequencing libraries from each sample and attempted to sequence and assemble a genome from each of these replicates. Applicants required a replicate of a sample to contain 3,000 unambiguous base calls for its read data to be included in that sample's final genome assembly. This threshold was based on the maximum number of unambiguous bases (2,820) observed in negative controls across all uncontaminated sequencing batches. One sequencing batch showed evidence of contamination: Applicants were able to assemble 7,615 unambiguous mumps bases from a water sample, with a median coverage of 4×. For samples prepared in this batch only, Applicants implemented an additional requirement for including a replicate in pooling: the assembly must have a median depth of coverage of $\Box 20\times$, 5 times the median depth of coverage of the water sample.

Multiple Sequence Alignment of Genotype G Whole Genomes

Applicants required a mumps genome to contain 11,538 unambiguous base calls (75% of the total 15,384-nucleotide genome with GenBank accession JNO12242.1) for inclusion in the alignment of whole genome sequences that Applicants used for downstream analysis. For 2 patients with samples taken at 2 time points (MuVs/Massachusetts.USA/19.16/5 [G] (1) and MuVs/Massachusetts.USA/19.16/5 [G] (2-20.16); MuVs/Massachusetts.USA/16.16/6 [G] (1) and MuVs/Massachusetts.USA/16.16/6 [G] (2-17.16)), Applicants only included the earlier sample in downstream analyses. The final alignment of whole genome sequences contains only samples belonging to genotype G; Applicants did not include MuVs/Massachusetts.USA/24.17/5 [K], which belongs to genotype K, in the alignment. In this alignment, Applicants also included 25 mumps virus genomes published on NCBI GenBank [43]. These comprise all of the sequences with organism "Mumps rubulavirus" available as of September 2017 that meet the following criteria: sequence length $\Box 14,000$ nucleotides, belong to genotype G, sample collection year and country of origin reported in GenBank, no evidence of extensive virus passaging or modification (for vaccine development, for example). The accessions are KY969482, KY996512, KY996511, KY996510, KY680540, KY680539, KY680538, KY680537, KY006858, KY006857, KY006856, KY604739, KF738114, KF738113, KF481689, KM597072, JX287391, JX287390, JX287389, JX287387, JX287385, JN012242, JN635498, AF280799, EU370207. Applicants aligned mumps virus genomes using MAFFT version 7.221 [48] with default parameters. Applicants provide the sequences and alignments used in analyses at http://doi.org/10.5281/zenodo.3338599.

Visualization of Coverage Depth Across Genomes

Applicants plotted aggregate depth of coverage across the 200 samples whose genomes were included in the final alignment (S1C Fig) as described in the work by Metsky and colleagues [49]. Applicants aligned reads against the reference genome with accession JX287389.1 and plotted over a 200-nt sliding window. Analysis of within- and between-sample variants Applicants ran V-Phaser 2.0 [50] via viralngs on all pooled reads mapping to a sample assembly to identify within-sample variants (S2 Data). To call a variant, Applicants required a minimum of 5 forward and reverse reads, as well as no more than 10-fold strand bias, as previously described [51]. Samples with genomes generated by the sequencing batch that showed evidence of contamination (see "Criteria for pooling across replicates" above) were not included in within host variant analysis. When analyzing variants in known contacts, Applicants used pairs of samples designated as "contact links," as described in "Relationship between epidemiological and genetic data" below. Between-sample variants were called by comparing each final genome sequence to JX287385.1, the earlier of the 2 available whole genomes from the 2006 mumps outbreak in Iowa, US (S2 Data). Applicants ignored all fully or partially ambiguous base calls and excluded sequences that did not descend from the USA 2006 clade from this analysis. When examining amino acid changes in HN given vaccination status (see "SH and HN multiple sequence alignment" below), Applicants ignored sequences from patients with unknown vaccination history.

Maximum Likelihood Estimation and Root-to-Tip Regression

Applicants generated a maximum likelihood tree using the whole genome genotype G multiple sequence alignment. Applicants used IQ-TREE version 1.3.13 [52] with a GTR substitution model and rooted the tree on the oldest sequence in this data set (accession KF738113.1) in FigTree version 1.4.2 [53]. To estimate root-to-tip distance of samples in the primary US lineage, Applicants subsetted the full genotype G alignment to include only samples descendent of the USA_2006 clade, including samples in this clade (see FIG. 1A) and used TempEst version 1.5 [54] with the best fitting root (heuristic residual mean squared function) to estimate distance from the root. Applicants used scikitlearn version 0.14.1 [55] in Python to perform linear regression of distances on dates. Applicants also generated maximum likelihood trees using the SH gene only (full 316-nucleotide mRNA), HN (coding region only), F (coding region only), and a concatenation of the aforementioned SH, HN, and F regions (S8 Fig). For each tree, Applicants started with the whole genome genotype G alignment (225 sequences) and extracted the relevant region(s). Applicants then removed any sequence with 2 or more consecutive ambiguous bases ("N"s) in any of SH, HN, or F, leaving 209 sequences in each alignment. Applicants used IQ-TREE version 1.5.5 with a GTR substitution [56] model to generate maximum likelihood trees.

Molecular Dating Using BEAST

Applicants performed all molecular clock analyses on whole genome sequences using BEAST version 1.8.4 [57]. Applicants excluded from the CDS the portion of the V protein after the insertion site [58] because of reading frame ambiguity in that region. On the CDS, Applicants used the SRD06 substitution model [59], which breaks codons into 2 partitions (positions [1+2] and 3) with HKY substitution models [60] and allows gamma site heterogeneity [61] (4 categories) on each. Applicants used a separate partition on noncoding sequence with an HKY substitution model and gamma site heterogeneity. To accommodate inexact dates in 7 sequences from NCBI GenBank, Applicants used sampled tip dates [62]. Applicants tested 6 models as described in the work by Metsky and colleagues [49]. Each was a combination of one of 2 clock models (strict clock and uncorrelated relaxed clock with lognormal distribution [63]) and 1 of 3 coalescent tree priors (constant size population, exponential growth population, and Bayesian Skygrid model [64] with 20 parameters). On each model, Applicants estimated marginal likelihood with path-sampling (PS) and stepping-stone sampling (SS) [65,66] (S2 Table) after sampling 100 path steps each with a chain length of 2 million. Applicants sampled trees and other parameters on each model by running BEAST for 200 million MCMC steps, sampling every 20,000 steps, and removing 20 million steps as burn-in. Applicants report the mean clock rate as the substitution rate for relaxed clock models. On the sampled trees, Applicants used TreeAnnotator version 1.8.4 to find the maximum clade credibility (MCC) tree and visualized it in FigTree version 1.4.3 [53]. To estimate tMRCAs (FIG. 1C and S2 Table), Applicants ran BEAST again for each of the 6 models, drawing from these same sets of sampled trees (without any parameters), for 10,000 steps, sampling every step. Applicants selected a relaxed clock and Skygrid model for plots of tMRCA distributions (FIG. 1C) and MCC trees over the whole genome genotype G sequences. Additionally, Applicants plotted (S11 Fig) a Skygrid reconstruction of the scaled population size (Net) using results from the selected model. The earliest time point on this plot is the lower (more recent) 95% HPD bound on the estimated root height.

Gene- and Site-Specific dN/dS Analyses

Applicants used BEAST version 1.8.4 [57] to estimate dN/dS per-site (S4C Fig and S3 Data) and pergene (S4D Fig) using the same alignment of 225 whole genome sequences described above (again, removing the portion of the V gene after the insertion site). For site-specific dN/dS estimation, Applicants used the CDS as input and created a separate partition for each codon position (3 partitions). Applicants used an HKY substitution model [60] on each partition and an uncorrelated relaxed clock with log-normal distribution [63] for branch rates. Here, Applicants sampled from the same set of trees that were sampled as described above in "Molecular Dating using BEAST" (relaxed clock with Skygrid tree prior). Applicants ran BEAST for 10 million MCMC steps, sampling every 10,000 steps. Applicants estimated site-specific dN/dS at each sampled state using renaissance counting [67,68] and show summary statistics at each site after discarding 1 million steps as burn-in. For per-gene estimation, Applicants created 8 separate partitions: 7 correspond to the CDS of a gene (F, HN, L, M, NP, SH, partial V), and the last corresponds to noncoding sequence. For each gene partition, Applicants used a Goldman-Yang codon model [69] with its own parameters for dN/dS (omega) and clock rate. For the noncoding partition, Applicants used an HKY substitution model [60] and gamma site heterogeneity [61] (4 categories). Applicants sampled tip dates as with the molecular clock analyses above and used a Bayesian Skyline tree prior [70] (10 groups). Applicants ran BEAST for 200 million MCMC steps to sample trees and parameter values, discarded 20 million steps as burn-in, and plotted the posterior distribution of omega for each gene partition.

Principal Component Analysis

The data set for PCA consisted of all SNPs from sites with exactly 2 alleles in the set of all genotype G genomes. Applicants imputed missing data with the R package missMDA [71] and calculated principal components with the R package FactoMineR [72]. Applicants discarded 14 samples as outliers based on visual inspection, leaving 211 samples in the final set.

Relationship Between Epidemiological and Genetic Data

Applicants obtained detailed epidemiological data for samples shared by MDPH from the Massachusetts Virtual Epidemiologic Network (MAVEN) surveillance system, an integrated web-based disease surveillance and case management system [73]. Applicants defined 2 types of epidemiological links: "contact links," between individuals who were determined to be close contacts during public health investigation and had symptom onset dates 7 to 33 days apart (individuals with mumps are usually considered infectious 2 days before through 5 days after onset of parotid swelling, with a typical incubation period of 16-18 days, ranging from 12-25 days) [26]; and "shared activity links," between individuals who participated in the same extracurricular activity (e.g., a sports team or university club) or frequented a specific residence or athletic facility. When Applicants refer to epidemiological links without specifying link type, Applicants include both types of links. Applicants calculated pairwise genetic distance between all pairs of samples in the whole genome genotype G alignment. For each pair, the genetic distance score is s/n, in which s is the number of unambiguous differing sites (both sequences must have an unambiguous base at the site, and the called bases must differ) and n is the number of sites at which both sequences have an unambiguous base call. To visualize the similarity between genomes and its relationship to epidemiological linkage, Applicants performed a multidimensional scaling on sequences in Clade II-outbreak (FIG. 1A). This clade is comprised of mostly cases from Harvard and the related community outbreak. Using their pairwise genetic distances, Applicants calculated a metric multidimensional scaling to 2 dimensions in R with cmdscale [74]. Applicants then evenly split the range of the output coordinates into a 100 Å~100 grid and collapsed each point into this grid and plotted the number of points at each grid coordinate; this improves visualization of nearly overlapping points (identical or near-identical genomes). Applicants plotted curves that represent epidemiological links between cases within each of the grid coordinates. This is shown in S7A Fig. To determine the ability of genetic distance to predict epidemiological linkage, Applicants again looked specifically at cases within Clade II-outbreak (FIG. 1A). Using the Python scikit-learn package [55], Applicants constructed a receiver operating characteristic (ROC) curve using pairwise distance between II-outbreak cases as the predictor variable and presence or absence of an epidemiological link as the binary response variable. This is shown in S7B Fig.

Model of Mumps Transmission in a University Setting

Applicants developed a stochastic model for mumps virus transmission accounting for the natural history of infection, vaccination status, and control measures implemented in response to the outbreak at Harvard. Our stochastic model of mumps virus transmission included the stages after initial infection, the durations of which Applicants inferred using data from previous clinical studies (S6A and S6C Fig). These included the gamma-distributed incubation period from infection to onset of mumps virus shedding in saliva [75]; the gamma-distributed period of latent infection from shedding onset to parotitis onset [75,76]; and the log-normally distributed time from parotitis onset to the cessation of shedding (defined in the work by Polgreen and colleagues [77]). For asymptomatic cases, Applicants defined the total duration of shedding (y) as the sum of independent random draws from the durations of shedding before and after parotitis onset, based on the lack of any reported difference in durations of shedding for symptomatic and asymptomatic cases [75]. To account for case isolation interventions implemented at Harvard, Applicants modeled the removal of symptomatic individuals one day after onset of parotitis. In comparison to the 70% probability for symptoms given infection among unvaccinated individuals [78], Applicants modeled the probability of symptoms given infection as uniformly distributed between 27.3% and 38.3% [5,79]. Applicants used previous estimates of the effectiveness and waning rate of mumps vaccination [51 and of the vaccination status distribution of individuals on a university campus [80] to account for susceptibility to infection among the Harvard population (N=22,000). Applicants scaled risk for mumps infection, given exposure, to time since receipt of the last vaccine dose, yielding the hazard ratio $$\xi_i = e^{\omega_0} \tau_i^{\omega_1}$$

for an individual i who received their last dose $\tau_i$ years previously, relative to an unvaccinated individual. For fitted values from the work by Lewnard and Grad [5], estimates were below 1.0 for individuals vaccinated since 1967, when the Jeryl Lynn vaccine was introduced (S6D Fig).

Given the instantaneous hazard of infection for an as yet uninfected individual i exposed to I(t) infected individuals $$\lambda_i(t) = \beta \xi_i I(t) N^{-1},$$

the probability of evading infection over the course of a 1-day simulated time step was exp $(-\lambda_i(t))$. The per-contact transmission rate ($\beta$) was measured from the initial (preintroduction) value of the effective reproductive number:

$$\beta = R_E(0) \bar{\gamma} \bar{\xi}^{-1}.$$

Inferring Transmission Dynamics

The number of cases (71) and identification of multiple, distinct viral clades within Harvard suggested limited permeation of mumps after any introduction. Applicants simulated dynamics of individual transmission chains to understand the epidemiological course of introduced viral lineages and to infer values of RE(0) and the number of importations of mumps virus. Applicants used the simulation model to sample from the distribution of the number of cases (X, including the index infection if symptomatic) resulting from a single introduction over a 1.5-year time course:

$$f\{x_i | R_E(0)\} = P[X = x_i | R_E(0)].$$

We resampled according to $f\{x_i | R_E(0)\}$ to define the distribution of the cumulative number of cases (Z) resulting from Y introductions, conditioned on $R_E(0)$:

$$g\{z_k | R_E(0), Y\} = P\left[Z = z_k = \sum_{i=1}^{y_j} x_i | R_E(0), Y = y_j\right].$$

Of the 71 cases at Harvard, 66 had mumps genomes in our data set, so we ran simulations where Z≥66, drawing k=66 cases at random to determine the number of distinct lineages (S, defined by the index infection) expected to be present within such a sample. The probability of obtaining 66 sequences and observing $S=s_m$ lineages among them is $$h\{s_m|R_E(0),Y,K=66\}=P[S=s_m|R_E(0),Y=y_j,K=66]\times P[Z\geq 66|R_E(0),Y].$$

The posterior density of our model also accounted for the probability of observing 71 symptomatic cases in total. Defined in terms of the number of introductions and the initial reproductive number, the model posterior was proportional to $$h\{4|R_E(0),Y,K=66\}\times g\{71|R_E(0),Y\},$$

where 4 is the number of viral lineages in the 66 Harvard cases (representing clades 0-HU, II-community, and 2 subclades within Clade II). We measured this probability from 100,000 iter-ates for each pairing of $R_E(0)\in\{0.10, 0.11, \ldots, 2.50\}$ and $Y\in\{1, 2, \ldots, 200\}$.

Last, we defined the minimum necessary third-dose vaccine coverage (C) to bring the effective number below unity using the relation $$[1-VE(0)]\times CR_E(t=0)\leq 1$$

sampling from previous estimates [5] that mumps vaccination protects against infection, prior to waning of immunity (here defined as VE(0)).

Transmission Reconstruction Using Outbreaker

Applicants used the R package outbreaker version 1.1-7 [81] to reconstruct transmission for samples included in Clade II-outbreak. Applicants estimated the generation interval by fitting a gamma distribution, via maximum likelihood, to the time between symptom onset dates for cases with confirmed epidemiological links (S6E Fig). Applicants used the same distribution for the colonization time and set the maximum number of generations between a case and its most recent sampled ancestor to 40. The resulting estimates are nearly identical to those reported in previous studies [82]. Applicants ran outbreaker 6 times in parallel, each with 1 million MCMC steps, and discarded the first 10% of states as burn-in. Applicants assessed run convergence and combined results for 5 of the 6 parallel runs to determine the reconstructed transmission tree (FIG. 2C right). For each link in the reconstruction, the support is the frequency of the link in the samples from the posterior (excluding the burn-in). To reconstruct transmission using SH sequences only (S7C Fig), Applicants extracted the SH gene from the II-outbreak alignment and ran outbreaker as described above, using the results from all 6 parallel runs in the analysis.

SH and HN Multiple Sequence Alignment

To analyze all published SH and HN mumps sequences, Applicants searched NCBI GenBank in July 2017 for all nucleotide sequences with organism "Mumps rubulavirus." Applicants performed a pairwise alignment between each sequence si and a reference genome (accession: JX287389.1) using MAFFT version 7.221 [48] with parameters: "—localpair—maxiterate 1000—preservecase." Applicants then extracted the SH sequence from each si based on the reference coordinates in the alignment, removing all SH sequences without the full 316-nucleotide region and all SH sequences with an insertion or deletion ("indel") relative to the reference. Applicants then used MAFFT with parameters "—localpair—maxiterate 1000—retree 2—preservecase" to create a multiple sequence alignment of the extracted SH gene sequences and removed any sequences with indels in this final alignment. Applicants repeated the same process for the HN region, requiring the full 1,749-nucleotide coding region. In both the SH and HN alignments, Applicants removed sequences from vaccine strains (i.e., genotype N, or another genotype marked as "(VAC)" or "vaccine"). Applicants also removed sequences with GenBank records indicating extensive passaging. In the SH alignment only, Applicants removed sequences with no reported collection date or country of origin, because these data are required for phylogeographic analyses. In samples with a collection decade (e.g., 1970s) but not a specific year, Applicants assigned the first year of the decade; in samples with only a collection year, Applicants assigned a decimal year of year+0.5 (e.g., 1970.5); in samples with year and month but no day, Applicants used the day halfway through the given month (e.g., 2015-03 becomes 2015-03-15) to calculate the decimal year; and in samples with an epidemiological week but no specific day, Applicants approximated the decimal year as year+ (epi week/52), except samples collected in epidemiological week 52 were relabeled as week 51.999 to avoid confusion with year-only samples.

In both the SH and HN alignments, Applicants relabeled outdated genotypes (M, E, and any subgenotypes [21]) and constructed a maximum likelihood tree (using IQ-TREE with a GTR substitution model, as described above) to assign a genotype if one was not reported on GenBank. Applicants preserved genotypes designated as "Unclassified" [21]. To each alignment, Applicants added all SH or HN sequences from individual patients generated in this study, except those with 2 or more consecutive ambiguous bases ("N"s) in the SH or HN region. The sequences used in the SH and HN analyses are listed in S4 Data.

SH Phylogeographic Analysis

To perform phylogenetic and phylogeographic analyses of the SH gene sequence, Applicants first sampled trees using BEAST version 1.8.4 [57]. Applicants used constant size population and strict clock models and used the HKY substitution model [60] with 4 rate categories and no codon partitioning. Applicants ran BEAST in 4 replicates, each for 500 million states with sampling every 50,000 states, and removed the first 150 million states as burn-in. Applicants verified convergence of all parameters across the 4 replicates and then combined the 4 replicates using LogCombiner. Applicants used TreeAnnotator to determine the MCC tree (FIG. 3C) from a resampling of 350 trees and visualized the result in FigTree version 1.4.3 [53]. Applicants computed a kernel density estimate of the probability distribution of the tMRCA over all sampled states for the 11 genotypes in this data set (S9 Fig).

Genomic Epidemiology of Mumps Transmission in the United States

PLOS Biology|doi.org/10.1371/journal.pbio.3000611 Feb. 11, 2020 18/28

To construct distributions of estimates, Applicants used resampling on the input sequences, similar to prior work facing sampling biases [83]. To perform this resampling, Applicants focused on only samples that were collected both within a window of time and from a geographic region with sufficient sampling. Namely, Applicants considered only sequences sampled in 2010 or afterward and collapsed the locations shown on the full data set (FIG. 3A) to just 4 global regions: US (consisting of only samples from the US), Europe (consisting of samples whose location was labeled as Eastern Europe, Northern Europe, Southern Europe, Western Europe, or the United Kingdom), East Asia (consisting of samples whose location was labeled as Eastern Asia or Japan), and South/Southeast Asia (consisting of samples whose location was labeled as Southeast Asia or Southern Asia). These 4 regions encompass 3,541 of the 3,646 SH gene sequences used in our analysis. Applicants ignored samples from 5 locations: Canada; Caribbean, Central America, and South America; Middle and Eastern Africa; Northern Africa; Middle East. See S10A Fig for a visual representation of these 4 regions. Then, Applicants randomly sampled 10 sequences (without replacement) from each region for each year (i.e., 2010-2011, 2011-2012, etc.). Applicants resampled the input sequences with this strategy 100 times. See S1 Text for a description of limitations of this resampling strategy, or each of the 100 resamplings of the input sequences, Applicants ran BEAST to sample trees, as described above, for 100 million states sampling every 10,000 states; Applicants removed 10 million states as burn-in and resampled to obtain 1,000 sampled trees. Then, Applicants performed phylogeographic analyses on each of the 100 samplings of input sequences by drawing from their sampled trees. Applicants used a discrete trait substitution model [84] on location in BEAST version 1.8.4. To estimate transition rates between locations Applicants used a nonreversible CTMC model with 42−4=12 rates. Furthermore, to evaluate the significance of routes in the diffusion process, Applicants added indicator variables to each rate through Bayesian stochastic search variable selection (BSSVS); Applicants set the number of nonzero rates to have a Poisson prior with a mean of 3.0, placing considerable prior probability on having the fewest rates needed to explain the diffusion. Applicants ran BEAST with 10 million states, sampling every 1,000 states, and removed the first 1 million as burn-in. At each sampled state, Applicants logged the complete Markov jump history [85,86], as well as a tree with the reconstructed ancestral location of each node. To determine an MCC tree across the 100 samplings of input sequences, Applicants ran TreeAnnotator on the sampled trees from each of the 100 samplings and then selected the MCC tree, from the 100 options, with the highest clade credibility score. Applicants show this one, colored by reconstructed ancestral locations, in S10B Fig. For each sampling xi of the 100 samplings of input sequences, Applicants counted the number of jumps between each pair of locations at each state using the complete Markov jump history after resampling the jump history every 10,000 states. For each xi, at each state, Applicants calculated the fraction of migrations between each region pair by dividing the number of migrations between the pair by the total number of migrations at that state. To quantify support for migration routes in each xi, Applicants calculated Bayes factors (BFs) on the rate indicator variables. Applicants calculated the posterior probability that a rate is nonzero as the mean of the indicator variable over the MCMC states, thereby providing a posterior odds. Applicants calculated the prior probability that a rate is nonzero as the expected number of nonzero rates divided by the number of rates, which reduces to $1/N$, where N is the number of locations; thus, the prior odds is $1/(N-1)$ or, in this case, ⅓. Applicants set an upper limit of 10,000 on the BF and a lower limit of 1.0. To estimate the proportion of ancestry for each xi, Applicants used skyline statistics via PACT [87] to calculate proportion of ancestry at each location from each other location: in particular, for each xi, Applicants used the sampled trees with ancestral locations as input (after resampling them every 10,000 states), padded the trees with migration events, broke the trees into temporal windows of 0.1 year going back 5 years prior to sampling, and estimated the proportion of history from tips in each time window. To summarize phylogeographic results across the 100 resamplings xi of the input sequences, Applicants show probability distributions across the xi. When plotting the fraction of migrations to each region from each other (S10C Fig), Applicants calculated the mean of this fraction across all the sampled states in each of the 100 runs to produce a point estimate for each xi and show the distribution of these means across the 100 xi. Applicants calculated the BFs on migration routes between the 4 regions by combining the sampled indicator variables across all 100 xi to compute the posterior odds (S10D Fig). Similarly, the proportion of ancestry plotted between a pair of locations in a time window (S10E Fig) is the mean across the 100 xi of the mean proportion for that pair in that time window from each xi. Applicants calculated the pointwise percentile bands in S10F Fig from the mean proportions in each xi across the xi (i.e., they are percentiles across the resamplings of the input sequences).

Supporting Information

S1 Fig. Sequencing results and predictors of outcome. (A) Distribution of mumps virus (MuV) RT-qPCR Ct value, taken at sample source, for all sequencing replicates prepared with both depletion and capture (see Materials and methods). Genome (blue): a replicate produces a genome passing the thresholds described in Materials and methods. MuV RT-qPCR serves as a predictor of sequencing outcome. (B) Distribution of collection interval (days between symptom onset and sample collection) for all samples prepared with both depletion and capture. Genome (blue) is defined as in panel A. Samples taken more than 4 days after symptom onset did not produce genomes in this study [88]. (C) Relative sequencing depth of coverage aggregated across 203 mumps genomes. (D) Number of unambiguous bases in the genome assembly of each sample by MuV:23S ratio (MuV copies by MuV RT-qPCR divided by 23S copies by 23S RT-qPCR; see Materials and methods). Each point is a replicate, colored by sequencing preparation method. (E) Normalized MuV reads (unique MuV reads divided by raw sequencing depth) in each sample by MuV:23S ratio. Points are as in panel D. Nine points with fraction mumps reads >0.04 are beyond the y-axis limits. In panels A, B, D, and E, reads from each replicate were downsampled to 1 million prior to assembly (see Materials and methods). In panels D and E, 1 point with a MuV:23S ratio <10-8 and 3 points with a MuV:23S ratio >10-3 are beyond the x-axis limits. Ct, cycle threshold; MuV, mumps virus; RT-qPCR, real-time quantitative polymerase chain reaction. (TIF) S2 Fig. Maximum likelihood tree, root-to-tip regression, and principal component analysis. (A) Maximum likelihood tree of the 225 mumps virus genotype G genomes used in this study. Tips are colored by sample source (MDPH or CDC); previously published genomes are indicated by unfilled circles. (B) Root-to-tip regression of genomes shown in panel A, rooted on GenBank accession KF738113 (Pune.IND, 1986). (C) Root-to-tip regression of genomes in the clade containing the two USA 2006 sequences (USA_2006; see FIG. 1A) as well as their descendants. (D) Principal component analysis of genetic variants from the genomes in panel A. Each point is a genome colored by its geographic location. CDC, Centers for Disease Control and Prevention; MDPH, Massachusetts Department of Public Health. (TIF) S3 Fig. Phylogenetic tree colored by institution. MCC tree of the 225 mumps virus genotype G genomes used in this study, colored by academic institution. Clades are labeled as in FIG. 1A. MCC, maximum clade credibility. (TIF) 4 Fig. Amino acid substitution in the mumps virus genome. (A) Variation in genomes generated in this study. Each row represents one of the 119 mumps HN amino acid sequences from the individuals in our study who had known vaccine status. Samples are displayed in order of descending time since last MMR vaccine dose. Colored variants indicate variation from the consensus of all included sequences. (B) Variation in all published genotype G HN sequences. Each row represents one of the 456 publicly available mumps genotype G HN sequences (including from genomes generated in this study). Identical sequences are collapsed and then grouped by hierarchical clustering. In both panels, amino acid substitutions relative to the Jeryl Lynn vaccine strain are highlighted in blue, with orange indicating a second variant allele and green indicating a third. Light red bars indicate possible neutralizing antibody epitopes, and dark red bars indicate potential N-glycosylation sites. (C) Estimate of dN/dS at each amino acid site in MuV coding regions, calculated across all 225 genotype G genomes used in this study. At each site, the mean estimate and 95% credible interval (not corrected for multiple testing) is shown. (D) Posterior density of dN/dS in each gene, using the same data set. (E) MCC tree of the 225 mumps genotype G genomes used in this study, colored by vaccination status. Clades are labeled as in FIG. 1A. HN, hemagglutinin gene; MCC, maximum clade credibility; MMR, Measles-Mumps-Rubella; MuV, mumps virus. (TIF) S5 Fig. Comparison of PCR-positive and PCR-negative Massachusetts samples. Comparison between 521 mumps PCR-negative samples tested in Massachusetts between 2016-01-01 and 2017-06-30, and 198 mumps samples from unique patients in Massachusetts in the same time period. In all panels, percentages have been recalculating after removing unknowns. (A) vaccination status of positives (n=198) and negatives (n=309) with known vaccination status. A chi-square test suggests there is no relationship between PCR result and vaccination status (p=0.012). (B) Years since vaccination for positives (n=198) and negatives (n=309) with known vaccination status. A chi-square tests suggests there is a relationship between PCR result and vaccination status (p=1.19 Å~10-7), and the plot shows that most recently vaccinated individuals were PCR-negative. (C) Collection interval for positives (n=196) and negatives (n=477) with known symptom onset and known collection date. A chi-square test suggests there is no relationship between PCR result and collection interval (p=0.918).

PCR, Polymerase Chain Reaction.

(TIF) S6 Fig. Parameters used in epidemiological models. Applicants illustrate fitted distributions of parameters of the modeled natural history of mumps infection. (A) Applicants calibrate a gamma distribution to the duration of the incubation period—defined from the time of mumps virus exposure to the onset of shedding—using data from experimental human mumps virus infections with known exposure times [75]. (B) Onset of mumps shedding generally precedes onset of symptoms in the clinical course. Applicants fit a gamma distribution describing the period of latent shedding to pooled data from 2 studies [75] and (C) apply previous estimates of the distribution of the duration of shedding after parotitis onset [77]. (D) Applicants obtain estimates of the distribution of vaccine protection within a university protection by pairing previous estimates of the association between the strength of vaccine protection and time since receipt of the last dose [5] to data on vaccine coverage in a large university [80]. (E) Applicants infer the distribution of the generation interval length in the Harvard using data from 10 cases with known exposure sources ("contact link"). A gamma distribution fitted by maximum likelihood recovers mean and dispersion estimates nearly identical to those reported in earlier mumps outbreaks [82]. (TIF) S7 Fig. Connection between epidemiological and genetic data. (A) Multidimensional scaling applied to samples in Clade II-outbreak (see FIG. 1A). Each point is a mumps genome and pairwise dissimilarities are based on Hamming distance (see Materials and methods). Genomes with known epidemiological links are connected with a red line. (B) ROC curve for samples within Clade II-outbreak using pairwise genetic distance (calculated as in panel A) as a predictor of epidemiological linkage. (C) Transmission reconstruction using individuals within Clade II-outbreak, using the SH gene or whole genome sequences. Inferred links with probability □0.7 are shown; arrows are colored by data set. Nodes with one or more inferred links are shown and are colored by institution. See also FIG. 2C, right. ROC, receiver operating characteristic; SH, small hydrophobic. (TIF) S8 Fig. Trees produced with single-gene and multigene sequences. Maximum likelihood trees using (A) the SH gene only, (B) the HN protein only, (C) a concatenation of the HN protein, the F coding region, and the SH gene, and (D) the complete mumps genome. In all panels, tips are colored by clades as defined in FIG. 1A and S2 Table. The HN protein sequence does a significantly better job at capturing the epidemiologically-relevant clades than the SH gene, and the tree created from SH+HN+F (nearly 25% of the genome) closely resembles the tree created from whole genome sequences. F, fusion protein; HN, hemagglutinin-neuraminidase; SH, small hydrophobic. (TIF) S9 Fig. tMRCA probability distributions for mumps genotypes using SH gene sequences. The date of the most recent genotype A clinical sample is indicated, excluding samples that closely resemble a mumps vaccine strain. SH, small hydrophobic; tMRCA, time to the most recent common ancestor. (TIF) S10 Fig. Additional analyses of global mumps spread using SH gene sequences. (A) World map indicating number of SH sequences in our data set from each of 15 regions; the 4 circled global regions represent the 4 regions from which Applicants resampled input for migration analyses (see Materials and methods for details regarding geographic and temporal resampling of sequences). (B) Tree with the highest clade credibility across all trees generated on resampled input from 4 global regions. Branch line thickness corresponds to posterior support or ancestry (indicated by branch color). (C) Migration between the 4 global regions shown in panel A. Each plot shows a posterior probability density, taken across resampled input, of the fraction of all reconstructed migrations that occur to the destination (indicated in upper right) from each of the other 3 sources. (D) Migration between the 4 global regions shown in panel A. Shading of each migration route indicates its statistical support (quantified with BF) in explaining the diffusion of mumps virus. (E) Average proportion of geographic ancestry of samples in each of the 4 global regions (labeled) from each of the 4 regions (colored), going back 5 years from sample collection. (F) Average proportion of Europe in geographic ancestry of US samples, and vice-versa. Shaded regions are pointwise percentile bands (2.5% to 97.5%) across 100 resamplings of the input sequences. Colors for panels B,C,D,E,F are by global region, as shown in the bottom right. BF, Bayes factor; SH, small hydrophobic. (TIF) S11 Fig. Skygrid reconstruction of population size. The scaled population size (Net) according to a Skygrid reconstruction. Dark line represents the median population size across samples from the posterior, and shaded area represents the 95% HPD interval. HPD, highest posterior density. (TIF) S1 Table. Sample metadata. Demographic information of all mumps cases in Massachusetts between 2016-01-01 and 2017-06-30, and the subset of these included in this study. (TIF) S2 Table. Model selection and tMRCA estimates across models. (A) Marginal likelihoods estimated in 6 models: combinations of 3 coalescent tree priors (constant size population, exponential growth population, and Skygrid) and 2 clock models (strict clock and uncorrelated relaxed clock with log-normal distribution). Estimates are with PS and SS. The BF are calculated against the model with constant size population and a strict clock. (B) Mean estimates of clock rate, date of tree root, and tMRCAs of the clades shown in FIG. 1A (excluding Clade 0-HU, which consists of one sample). USA-4 corresponds to "Clades I and II" in FIG. 1A. Below each mean estimate is the 95% highest posterior density interval. tMRCAs of additional unlabeled odes are available at http://doi.org/10.5281/zenodo.3338599. BF, Bayes factor; PS, path sampling; SS, stepping-stone sampling; tMRCA, time to the most recent common ancestor. (TIF) S3 Table. Viruses identified in mumps PCR-negative samples. Influenzavirus B is the only segmented virus listed, and Applicants identify 51 reads mapping to 6 of the 8 segments: in order, 2, 6, 0, 0, 8, 10, 4, 21 reads to each segment. PCR, polymerase chain reaction. (TIF) S1 Data. Sample metadata. Information and metadata regarding all mumps PCR-positive and PCR-negative samples on which sequencing was attempted. PCR, polymerase chain reaction. (XL X) S2 Data. Single nucleotide polymorphisms. List of identified nonsynonymous SNPs, including the frequency of each SNP. Separate list of identified within-host variants above 2% frequency. Separate list of SNPs in possible immunogenic regions of HN and NP in US samples from 2016 to 2017 (all positions relative to the relevant gene). FIN, hemagglutinin-neuraminidase; NP, nucleoprotein; SNP, single nucleotide polymorphism. (XLSX) S3 Data. dN/dS values. Calculated dN/dS value and confidence interval for each amino acid position across the mumps virus genome. (XLSX) S4 Data. Publicly available SH and HN sequences. List of SH and HN sequences and corresponding metadata used in analysis, as well as SH sequences available for resampling. HN, hemagglutinin-neuraminidase; SH, small hydrophobic. (XLSX) S1 Text. (DOCX)

Acknowledgments

Applicants thank A. Matthews and S. Winnicki for management and guidance; I. Shlyakhter, S. Weingarten-Gabbay, S. Ye, C. Tomkins-Tinch, and other members of the Sabeti Laboratory for discussions and reading of the manuscript; J. Hall, P. Patel, E. Buzby, K. Chen, and F. Halpern-Smith for mumps diagnosis and laboratory support; A. Osinski, C. Brandeburg, H. Johnson, J. Cohen, K. Royce, M. Popstefanija, N. Harrington, R. Hernandez, and J. Leaf for case management and epidemiological investigation; T. Mason and the Broad Institute Genomics Platform or sequencing support; M. Salit for sharing reagents. Applicants are indebted to mumps patients and clinical and epidemiological teams for making this work possible. The findings and conclusions in this report are those of the authors and do not necessarily represent the official position of the Centers for Disease Control and Prevention, the National Institute of General Medical Sciences, the National Institute of Allergy and Infectious Diseases, or the National Institutes of Health.

Author Contributions

Conceptualization: Shirlee Wohl, Anne Piantadosi, Katherine J. Siddle, Christian B. Matranga, Sandra Smole, Yonatan H. Grad, Pardis C. Sabeti. Data curation: Shirlee Wohl, Hayden C. Metsky, Meagan Burns, Rebecca J. McNall. Formal analysis: Shirlee Wohl, Hayden C. Metsky, Stephen F. Schaffner, Anne Piantadosi, Joseph A. Lewnard, Bridget Chak, Lydia A. Krasilnikova, Katherine J. Siddle, Elizabeth H. Byrne. Funding acquisition: Pardis C. Sabeti. Investigation: Shirlee Wohl, Anne Piantadosi, Meagan Burns, Bridget Chak, Katherine J. Siddle, Bettina Bankamp, Scott Hennigan, Brandon Sabina, Rickey R. Shah, James Qu, Soheyla Gharib, Susan Fitzgerald, Paul Barreira, Stephen Fleming, Susan Lett, Lawrence C. Madoff, Sandra Smole. Methodology: Hayden C. Metsky, Anne Piantadosi, Joseph A. Lewnard, Katherine J. Siddle, Christian B. Matranga, Rickey R. Shah. Project administration: Shirlee Wohl, Bridget Chak, Nathan L. Yozwiak, Bronwyn L. MacInnis, Pardis C. Sabeti. Resources: Paul A. Rota, Lawrence C. Madoff, Sandra Smole, Pardis C. Sabeti. Software: Daniel J. Park. Supervision: Christian B. Matranga, Daniel J. Park, Susan Fitzgerald, Paul Barreira, Paul A. Rota, Lawrence C. Madoff, Nathan L. Yozwiak, Bronwyn L. MacInnis, Sandra Smole, Yonatan H. Grad, Pardis C. Sabeti. Visualization: Shirlee Wohl, Hayden C. Metsky, Stephen F. Schaffner, Anne Piantadosi, Joseph A. Lewnard, Elizabeth H. Byrne. Writing—original draft: Shirlee Wohl, Hayden C. Metsky, Stephen F. Schaffner, Anne Piantadosi, Joseph A. Lewnard, Lydia A. Krasilnikova, Nathan L. Yozwiak, Bronwyn L. MacInnis. Writing—review & editing: Shirlee Wohl, Hayden C. Metsky, Stephen F. Schaffner, Anne Piantadosi, Meagan Burns, Joseph A. Lewnard, Lydia A. Krasilnikova, Katherine J. Siddle, Christian B. Matranga, Daniel J. Park, Paul Barreira, Paul A. Rota, Lawrence C. Madoff, Nathan L. Yozwiak, Bronwyn L. MacInnis, Yonatan H. Grad, Pardis C. Sabeti.

Genomic Epidemiology of Mumps Transmission in the United States

PLOS Biology|doi.org/10.1371/journal.pbio.3000611 Feb. 11, 2020 24/28

REFERENCES FOR EXAMPLE

1. Centers for Disease Control and Prevention. Mumps Cases and Outbreaks. 9 Feb. 2018. www.cdc.gov/mumps/outbreaks.html. [cited 9 Mar. 2018].
2. Centers for Disease Control and Prevention. FastStats—Immunization. J Infect Dis. 2017; 198: 508-515.
3. Centers for Disease Control and Prevention. Measles Prevention: Recommendations of the Immunization Practices Advisory Committee (ACIP). MMWR Surveill Summ. 1989; 38: 1-18.
4. Dayan G H, Quinlisk M P, Parker A A, Barskey A E, Harris M L, Schwartz J M H, et al. Recent resurgence of mumps in the United States. N Engl J Med. 2008; 358: 1580-1589. doi.org/10.1056/NEJMoa0706589 PMID: 18403766
5. Lewnard J A, Grad Y H. Vaccine waning and mumps re-emergence in the United States. Sci Transl Med.2018.
6. Centers for Disease Control and Prevention. National Notifiable Diseases Surveillance System. 2017.
7. Walkty A, Van Caeseele P, Hilderman T, Buchan S, Weiss E, Sloane M, et al. Mumps in prison: description of an outbreak in Manitoba, Canada. Can J Public Health. 2011; 102: 341-344. PMID: 22032098
8. Barskey A E, Schulte C, Rosen J B, Handschur E F, Rausch-Phung E, Doll M K, et al. Mumps outbreak in Orthodox Jewish communities in the United States. N Engl J Med. 2012; 367: 1704-1713. doi.org/10.1056/NEJMoa1202865 PMID: 23113481
9. Fields V S, Safi H, Waters C, Dillaha J, Capelle L, Riklon S, et al. Mumps in a highly vaccinated Marshallese community in Arkansas, USA: an outbreak report. Lancet Infect Dis. 2019; 19: 185-192. doi.org/10.1016/S1473-3099(18)30607-8 PMID: 30635255
10. Faria N R, Kraemer M U G, Hill S C, Goes de Jesus J, Aguiar R S, Iani F C M, et al. Genomic and epidemiological monitoring of yellow fever virus transmission potential. Science. 2018; 361: 894-899. doi.org/10.1126/science.aat7115 PMID: 30139911
11. Weill F-X, Domman D, Njamkepo E, Almesbahi A A, Naji M, Nasher S S, et al. Genomic insights into the 2016-2017 cholera epidemic in Yemen. Nature. 2019. doi.org/10.1038/s41586-018-0818-3 PMID: 30602788
12. Gardy J L, Johnston J C, Ho Sui S J, Cook V J, Shah L, Brodkin E, et al. Whole-genome sequencing and social-network analysis of a tuberculosis outbreak. N Engl J Med. 2011; 364: 730-739. doi.org/10.1056/NEJMoa1003176 PMID: 21345102
13. Holmes E C, Ghedin E, Miller N, Taylor J, Bao Y, St George K, et al. Whole-genome analysis of human influenza A virus reveals multiple persistent lineages and reassortment among recent H3N2 viruses. PLoS Biol. 2005; 3(9): e300. doi.org/10.1371/journal.pbio.0030300 PMID: 16026181
14. Yuan L, Huang X-Y, Liu Z-Y, Zhang F, Zhu X-L, Yu J-Y, et al. A single mutation in the prM protein of Zika virus contributes to fetal microcephaly. Science. 2017; 358: 933-936. doi.org/10.1126/science.aam7120 PMID: 28971967
15. Diehl W E, Lin A E, Grubaugh N D, Carvalho L M, Kim K, Kyawe P P, et al. Ebola Virus Glycoprotein with Increased Infectivity Dominated the 2013-2016 Epidemic. Cell. 2016; 167: 1088-1098.e6. doi.org/10.1016/j.cell.2016.10.014 PMID: 27814506
16. Kugelman J R, Sanchez-Lockhart M, Andersen K G, Gire S, Park D J, Sealfon R, et al. Evaluation of the potential impact of Ebola virus genomic drift on the efficacy of sequence-based candidate therapeutics. MBio. 2015; 6. doi.org/10.1128/mBio.02227-14 PMID: 25604787
17. Grubaugh N D, Ladner J T, Lemey P, Pybus O G, Rambaut A, Holmes E C, et al. Tracking virus outbreaks in the twenty-first century. Nat Microbiol. 2019; 4: 10-19. doi.org/10.1038/s41564-018-0296-2 PMID: 30546099
18. Snitkin E S, Zelazny A M, Thomas P J, Stock F, NISC Comparative Sequencing Program Group, Henderson D K, et al. Tracking a hospital outbreak of carbapenem-resistant *Klebsiella pneumoniae* with whole genome sequencing. Sci Transl Med. 2012; 4: 148ra116.
19. Gardy J L, Loman N J. Towards a genomics-informed, real-time, global pathogen surveillance system. Nat Rev Genet. 2018; 19: 9-20. doi.org/10.1038/nrg.2017.88 PMID: 29129921
20. Jin L, Rima B, Brown D, Orvell C, Tecle T, Afzal M, et al. Proposal for genetic characterisation of wildtype mumps strains: preliminary standardisation of the nomenclature. Arch Virol. 2005; 150: 1903-1909. doi.org/10.1007/s00705-005-0563-4 PMID: 15959834
21. World Health Organization. Mumps virus nomenclature update: 2012. Weekly Epidemiological Record. 2012; 87: 217-224. PMID: 24340404
22. Elbadawi L I, Talley P, Rolfes M A, Millman A J, Reisdorf E, Kramer N A, et al. Non-mumps Viral Parotitis During the 2014-2015 Influenza Season in the United States. Clin Infect Dis. 2018; 67: 493-501.doi.org/10.1093/cid/ciy137 PMID: 29617951 Genomic epidemiology of mumps transmission in the United States PLOS Biology I doi.org/10.1371/journal.pbio.3000611 Feb. 11, 2020 25/28
23. Centers for Disease Control and Prevention. Mumps For Healthcare Providers. 12 Jul. 2018. www.cdc.gov/mumps/hcp.html. [cited 20 Dec. 2018].
24. Centers for Disease Control and Prevention (CDC). Update: mumps outbreak—New York and New Jersey, June 2009-January 2010. MMWR Morb Mortal Wkly Rep. 2010; 59: 125-129. PMID: 20150887
25. Moncla L B A. Multiple introductions of mumps virus into Washington State. 22 Oct. 2018. bedford.io/blog/mumps-in-washington-state/. [cited 20 Dec. 2018].
26. Kimberlin D W, Brady M T, Jackson M A, Long S S. Red Book, (2015): 2015 Report of the Committee on Infectious Diseases. Am Acad Pediatrics; 2015.
27. Gouma S, Vermeire T, Van Gucht S, Martens L, Hutse V, Cremer J, et al. Differences in antigenic sites and other functional regions between genotype A and G mumps virus surface proteins. Sci Rep. 2018; 8: 13337. doi.org/10.1038/s41598-018-31630-z PMID: 30190529
28. Wolinsky J S, Waxham M N, Server A C. Protective effects of glycoprotein-specific monoclonal antibodies on the course of experimental mumps virus meningoencephalitis. J Virol. 1985; 53: 727-734. PMID:3973964
29. Rasheed M A U, Hickman C J, McGrew M, Sowers S B, Mercader S, Hopkins A, et al. Decreased humoral immunity to mumps in young adults immunized with MMR vaccine in childhood. Proc Natl Acad Sci USA. 2019. doi.org/10.1073/pnas.1905570116 PMID: 31481612
30. Rubin S A, Link M A, Sauder C J, Zhang C, Ngo L, Rima B K, et al. Recent mumps outbreaks in vaccinated populations: no evidence of immune escape. J Virol. 2012; 86: 615-620. doi.org/10.1128/JVI.06125-11 PMID: 22072778
31. Rubin S A, Qi L, Audet S A, Sullivan B, Carbone K M, Bellini W J, et al. Antibody induced by immunization with the Jeryl Lynn mumps vaccine strain effectively neutralizes a heterologous wild-type mumps virus associated with a large outbreak. J Infect Dis. 2008; 198: 508-515. doi.org/10.1086/590115 PMID: 18558869
32. Clemmons N, Hickman C, Lee A, Marin M, Patel M. Mumps. In: Centers for Disease Control and Prevention, editor. Manual for the Surveillance of Vaccine-Preventable Diseases. 2018.
33. Yeo R P, Afzal M A, Forsey T, Rima B K. Identification of a new mumps virus lineage by nucleotide sequence analysis of the S H gene of ten different strains. Arch Virol. 1993; 128: 371-377. doi.org/10.1007/bf01309447 PMID: 8435047
34. Jin L, O'rvell C, Myers R, Rota P A, Nakayama T, Forčić D, et al. Genomic diversity of mumps virus and global distribution of the 12 genotypes. Rev Med Virol. 2015; 25: 85-101. doi.org/10.1002/rmv.1819 PMID: 25424978
35. Centers for Disease Control and Prevention. Mumps 2012 Case Definition. In: National Notifiable Diseases Surveillance System (NNDSS) [Internet]. 2012. wwwn.cdc.gov/nndss/conditions/mumps/case-definition/2012/. [cited 9 Mar. 2018].
36. Centers for Disease Control and Prevention. Real-time (TaqMan) RT-PCR Assay for the Detection of Mumps Virus RNA in Clinical Samples. 2 Apr. 2010. www.cdc.gov/mumps/downloads/lab-rt-perassay-detect.pdf. [cited 9 Mar. 2018].
37. Van Camp G, Chapelle S, De Wachter R. Amplification and sequencing of variable regions in bacterial 23S ribosomal RNA genes with conserved primer sequences. Curr Microbiol. 1993; 27: 147-151. doi.org/10.1007/bf01576012 PMID: 7691306
38. Matranga C B, Andersen K G, Winnicki S, Busby M, Gladden A D, Tewhey R, et al. Enhanced methods for unbiased deep sequencing of Lassa and Ebola RNA viruses from clinical and biological samples. Genome Biol. 2014; 15.

39. Metsky H C, Siddle K J, Gladden-Young A, Qu J, Yang D K, Brehio P, et al. Capturing sequence diversity in metagenomes with comprehensive and scalable probe design. Nat Biotechnol. 2019; 37: 160-168. doi.org/10.1038/s41587-018-0006-x PMID: 30718881

40. Chris Tomkins-Tinch, Simon Ye, Hayden Metsky, Irwin Jungreis, Rachel Sealfon, Xiao Yang, Kristian Andersen, Mike Lin, and Daniel Park. viral-ngs. doi.org/10.5281/zenodo.1030020. [cited 30 Sep. 2019].

41. Li H, Handsaker B, Wysoker A, Fennell T, Ruan J, Homer N, et al. The Sequence Alignment/Map format and SAMtools. Bioinformatics. 2009; 25: 2078-2079. doi.org/10.1093/bioinformatics/btp352 PMID: 19505943

42. Wood D E, Salzberg S L. Kraken: ultrafast metagenomic sequence classification using exact alignments. Genome Biol. 2014; 15: R46. doi.org/10.1186/gb-2014-15-3-r46 PMID: 24580807

43. Clark K, Karsch-Mizrachi I, Lipman D J, Ostell J, Sayers E W. GenBank. Nucleic Acids Res. 2016; 44:D67. doi.org/10.1093/nar/gkv1276 PMID: 26590407 Genomic epidemiology of mumps transmission in the United States PLOS Biology I doi.org/10.1371/journal.pbio.3000611 Feb. 11, 2020 26/28

44. Grabherr M G, Haas B J, Yassour M, Levin J Z, Thompson D A, Amit I, et al. Full-length transcriptome assembly from RNA-Seq data without a reference genome. Nat Biotechnol. 2011; 29: 644-652. doi.org/10.1038/nbt.1883 PMID: 21572440

45. Altschul S F, Gish W, Miller W, Myers E W, Lipman D J. Basic local alignment search tool. J Mol Biol. 1990; 215: 403-410. doi.org/10.1016/S0022-2836(05)80360-2 PMID: 2231712

46. Bankevich A, Nurk S, Antipov D, Gurevich A A, Dvorkin M, Kulikov A S, et al. SPAdes: a new genome assembly algorithm and its applications to single-cell sequencing. J Comput Biol. 2012; 19: 455-477. doi.org/10.1089/cmb.2012.0021 PMID: 22506599

47. Buchfink B, Xie C, Huson D H. Fast and sensitive protein alignment using DIAMOND. Nat Methods. 2015; 12: 59-60. doi.org/10.1038/nmeth.3176 PMID: 25402007

48. Katoh K, Standley D M. MAFFT multiple sequence alignment software version 7: improvements in performance and usability. Mol Biol Evol. 2013; 30: 772-780. doi.org/10.1093/molbev/mst010 PMID: 23329690

49. Metsky H C, Matranga C B, Wohl S, Schaffner S F, Freije C A, Winnicki S M, et al. Zika virus evolution and spread in the Americas. Nature. 2017; 546: 411-415. doi.org/10.1038/nature22402 PMID: 28538734

50. Yang X, Charlebois P, Macalalad A, Henn M R, Zody M C. V-Phaser 2: variant inference for viral populations. BMC Genomics. 2013; 14: 674. doi.org/10.1186/1471-2164-14-674 PMID:

51. Gire S K, Goba A, Andersen K G, Sealfon R S G, Park D J, Kanneh L, et al. Genomic surveillance elucidates Ebola virus origin and transmission during the 2014 outbreak. Science. 2014; 345: 1369-1372. doi.org/10.1126/science.1259657 PMID: 25214632

52. Nguyen L-T, Schmidt H A, von Haeseler A, Minh B Q. I Q-TREE: a fast and effective stochastic algorithm for estimating maximum-likelihood phylogenies. Mol Biol Evol. 2015; 32: 268-274. doi.org/10.1093/molbev/msu300 PMID: 25371430

53. Rambaut A. FigTree. 2016. http://tree.bio.ed.ac.uk/software/figtree/. [cited 30 Sep. 2019].

54. Rambaut A, Lam T T, Max Carvalho L, Pybus O G. Exploring the temporal structure of heterochronous sequences using TempEst (formerly Path-O-Gen). Virus Evol. 2016; 2: vew007.

55. Pedregosa F, Varoquaux G, Gramfort A, Michel V, Thirion B, Grisel O, et al. Scikit-learn: Machine Learning in Python. J Mach Learn Res. 2011; 12: 2825-2830.

56. Tavare'S. Some probabilistic and statistical problems in the analysis of DNA sequences. Lectures on mathematics in the life sciences. 1986; 17: 57-86.

57. Drummond A J, Suchard M A, Xie D, Rambaut A. Bayesian phylogenetics with BEAUti and the BEAST 1.7. Mol Biol Evol. 2012; 29: 1969-1973. doi.org/10.1093/molbev/mss075 PMID: 22367748

58. Paterson R G, Lamb R A. RNA editing by G-nucleotide insertion in mumps virus P-gene mRNA transcripts. J Virol. 1990; 64: 4137-4145. PMID: 2166809

59. Shapiro B, Rambaut A, Drummond A J. Choosing appropriate substitution models for the phylogenetic analysis of protein-coding sequences. Mol Biol Evol. 2006; 23: 7-9. doi.org/10.1093/molbev/msj021 PMID: 16177232

60. Hasegawa M, Kishino H, Yano T. Dating of the human-ape splitting by a molecular clock of mitochondrial DNA. J Mol Evol. 1985; 22: 160-174. doi.org/10.1007/bf02101694 PMID: 3934395

61. Yang Z. Maximum likelihood phylogenetic estimation from DNA sequences with variable rates over sites: approximate methods. J Mol Evol. 1994; 39: 306-314. doi.org/10.1007/bf00160154 PMID: 7932792

62. Shapiro B, Ho S Y W, Drummond A J, Suchard M A, Pybus O G, Rambaut A. A Bayesian phylogenetic method to estimate unknown sequence ages. Mol Biol Evol. 2011; 28: 879-887. doi.org/10.1093/molbev/msq262 PMID: 20889726

63. Drummond A J, Ho S Y W, Phillips M J, Rambaut A. Relaxed phylogenetics and dating with confidence. PLoS Biol. 2006; 4(5): e88. doi.org/10.1371/journal.pbio.0040088 PMID: 16683862

64. Gill M S, Lemey P, Faria N R, Rambaut A, Shapiro B, Suchard M A. Improving Bayesian population dynamics inference: a coalescent-based model for multiple loci. Mol Biol Evol. 2013; 30: 713-724. doi.org/10.1093/molbev/mss265 PMID: 23180580

65. Baele G, Lemey P, Bedford T, Rambaut A, Suchard M A, Alekseyenko A V. Improving the accuracy of demographic and molecular clock model comparison while accommodating phylogenetic uncertainty. Mol Biol Evol. 2012; 29: 2157-2167. doi.org/10.1093/molbev/mss084 PMID: 22403239

66. Baele G, Li W L S, Drummond A J, Suchard M A, Lemey P. Accurate Model Selection of Relaxed Molecular Clocks in Bayesian Phylogenetics. Molecular Biology and Evolution. 2012. pp. 239-243. doi.org/10.1093/molbev/mss243 PMID: 23090976 Genomic epidemiology of mumps transmission in the United States PLOS Biology I doi.org/10.1371/journal.pbio.3000611 Feb. 11, 2020 27/28

67. O'Brien J D, Minin V N, Suchard M A. Learning to count: robust estimates for labeled distances between molecular sequences. Mol Biol Evol. 2009; 26: 801-814. doi.org/10.1093/molbev/msp003 PMID: 19131426

68. Lemey P, Minin V N, Bielejec F, Kosakovsky Pond S L, Suchard M A. A counting renaissance: combining stochastic mapping and empirical Bayes to quickly detect amino acid sites under positive selection. Bioinformatics. 2012; 28: 3248-3256. doi.org/10.1093/bioinformatics/bts580 PMID: 23064000

69. Goldman N, Yang Z. A codon-based model of nucleotide substitution for protein-coding DNA sequences. Mol Biol Evol. 1994; 11: 725-736. doi.org/10.1093/oxfordjournals-.molbev.a040153 PMID: 7968486

70. Drummond A J, Rambaut A, Shapiro B, Pybus O G. Bayesian coalescent inference of past population dynamics from molecular sequences. Mol Biol Evol. 2005; 22: 1185-1192. doi.org/10.1093/molbev/msi103 PMID: 15703244
71. Josse J, Husson F, Others. missMDA: a package for handling missing values in multivariate data analysis. J Stat Softw. 2016; 70: 1-31.

72. Lê S, Josse J, Husson F. FactoMineR: an R package for multivariate analysis. J Stat Softw. 2008. http://citeseerx-.ist.psu.edu/viewdoc/download?doi=10.1.1.422.7829&rep=rep1&type=pdf. [cited 9 Mar. 2018].

73. Troppy S, Haney G, Cocoros N, Cranston K, DeMaria A Jr. Infectious disease surveillance in the 21st century: an integrated web-based surveillance and case management system. Public Health Rep. 2014; 129: 132-138. doi.org/10.1177/003335491412900206 PMID: 24587547
74. R Core Team. R: A Language and Environment for Statistical Computing. In: R Foundation for Statistical Computing [Internet]. www.R-project.org. [cited 9 Mar. 2018].
75. Henle G, Henle W. Isolation of mumps virus from human beings with induced apparent or inapparent infections. J Exp Med. 1948; 88: 223-232. doi.org/10.1084/jem.88.2.223 PMID: 18873870
76. Ennis F A, Jackson D. Isolation of virus during the incubation period of mumps infection. J Pediatr. 1968; 72: 536-537. doi.org/10.1016/s0022-3476(68)80347-6 PMID: 5647297
77. Polgreen P M, Bohnett L C, Cavanaugh J E, Gingerich S B, Desjardin L E, Harris M L, et al. The duration of mumps virus shedding after the onset of symptoms. Clin Infect Dis. 2008; 46: 1447-1449. doi.org/10.1086/587104 PMID: 18419451
78. Galazka A M, Robertson S E, Kraigher A. Mumps and mumps vaccine: a global review. Bull World Health Organ. 1999; 77: 3-14. PMID: 10063655
79. Dittrich S, Hahne'S, van Lier A, Kohl R, Boot H, Koopmans M, et al. Assessment of serological evidence for mumps virus infection in vaccinated children. Vaccine. 2011; 29: 9271-9275. doi.org/10.1016/j.vaccine.2011.09.072 PMID: 21983156
80. Cardemil C V, Dahl R M, James L, Wannemuehler K, Gary H E, Shah M, et al. Effectiveness of a Third Dose of MMR Vaccine for Mumps Outbreak Control. N Engl J Med. 2017; 377: 947-956. doi.org/10.1056/NEJMoa1703309 PMID: 28877026

81. Jombart T, Cori A, Didelot X, Cauchemez S, Fraser C, Ferguson N. Bayesian reconstruction of disease outbreaks by combining epidemiologic and genomic data. PLoS Comput Biol. 2014; 10(1): e1003457.doi.org/10.1371/joumal.pcbi.1003457 PMID: 24465202

82. Vink M A, Bootsma M C J, Wallinga J. Serial intervals of respiratory infectious diseases: a systematic review and analysis. Am J Epidemiol. 2014; 180: 865-875. doi.org/10.1093/aje/kwu209 PMID:25294601
83. Bedford T, Riley S, Barr I G, Sroor S, Chadha M, Cox N J, et al. Global circulation patterns of seasonal influenza viruses vary with antigenic drift. Nature. 2015; 523: 217-220. doi.org/10.1038/nature14460 PMID: 26053121
84. Lemey P, Rambaut A, Drummond A J, Suchard M A. Bayesian phylogeography finds its roots. PLoS Comput Biol. 2009; 5(9): e1000520. doi.org/10.1371/journal.pcbi.1000520 PMID: 19779555
85. Gong L I, Suchard M A, Bloom J D. Stability-mediated epistasis constrains the evolution of an influenza protein. Elife. 2013; 2: e00631. doi.org/10.7554/eLife.00631 PMID: 23682315
86. Minin V N, Suchard M A. Fast, accurate and simulation-free stochastic mapping. Philos Trans R Soc Lond B Biol Sci. 2008; 363: 3985-3995. doi.org/10.1098/rstb.2008.0176 PMID: 18852111
87. Bedford T. Posterior Analysis of Coalescent Trees (PACT). github.com/trvrb/PACT. [cited 14 Jan. 2018].
88. Rota J S, Rosen J B, Doll M K, McNall R J, McGrew M, Williams N, et al. Comparison of the sensitivity of laboratory diagnostic methods from a well-characterized outbreak of mumps in New York city in 2009. Clin Vaccine Immunol. 2013; 20: 391-396. doi.org/10.1128/CVI.00660-12 PMID: 23324519

What is claimed is:

1. A computer-implemented method to use aggregated data to provide a population informed assessment of infection, comprising:

receiving, by one or more computing systems and from a user computing device associated with a user, a communication comprising user data;

identifying, by the one or more computing systems, a sub-set of users from a plurality of other users having a connectivity score above a threshold connectivity score and based in part on comparing user data with aggregated data from the plurality of other users;

identifying, by the one or more computing systems, common attributes from the user data from the sub-set of other users;

receiving, by the user computing device, a broadcast wireless communication from a proximate second user computing device of a second user;

broadcasting, by the user computing device, a second broadcast wireless communication to the proximate second user computing device of the second user;

determining, by the user computing device, a length of time of the contact of the user computing device to the proximate second user computing device and a distance between the user computing device and the proximate second user computing device during the contact;

registering, by the user computing device, contact of the user computing device to the proximate second user computing device based on the length of time of the contact of the user computing device to the proximate second user computing device and the distance between the user computing device and the proximate second user computing device;

communicating, by the user computing device, the registered contact to the one or more computing systems;

determining, by the one or more computing systems, a population informed risk of infection of the user based at least in part on the registered contact, the connectivity score, the common attributes, and from a population model of a disease event; and communicating, by the one or more computing systems and to the user computing device, recommendations for further diagnostics and/or treatment based on the population informed risk of infection of the user and instructions to display the recommendations on a user interface of the user computing device.

2. The computer-implemented method of claim 1, wherein the population model determines a rate of infectivity for COVID-19.

3. The computer-implemented method of claim 1, wherein the population model determines a rate of infectivity for a given geographic region.

4. The computer-implemented method of claim 1, wherein the model is generated via a machine-learning function.

5. The computer-implement method of claim 1, wherein the model is a compartmental model, a Partially Observed Markov Process (POMP)-based model, or a combination thereof.

6. The computer-implemented method of claim 1, wherein the user data comprises user attributes comprising social network connectivity, contact information, dwelling, place of employment, school of enrollment, or a combination thereof.

7. The computer-implemented method of claim 1, wherein user data comprises health data comprising medical history, a genetic profile, a current symptoms profile, diagnostic results, or a combination thereof.

8. The computer-implemented method of claim 1, wherein the health data comprises a partial or whole genomic sequence of a SARS-Cov-2 isolated from the user.

9. The computer-implemented method of claim 8 where the partial or whole genomic sequence is used to determine a pathogen transmission chain.

10. The computer-implemented method of claim 1, further comprising communicating, by the one or more computing systems, a status of a user to the user computing device to display to the user.

11. The computer-implemented method of claim 1, wherein the user computing device broadcasts a location and identity via a wireless communication technology.

12. The computer-implemented method of claim 11, wherein the user computing device broadcasts via Bluetooth.

13. The computer-implemented method of claim 1, wherein identification of the sub-set of users is based on one or more of location data of the user computing device and contact data from the user computing device.

14. The computer-implemented method of claim 1, wherein identification of the sub-set of users is based at least in part on a list of contacts from one or more of a contact application and a social media application.

15. The computer-implemented method of claim 1, further comprising generating, by the one or more computing systems, a simulation of response to one or more simulated actions to be taken by a user.

16. The computer-implemented method of claim 1, further comprising communicating, by the one or more computing systems, instructions to the user computing device, the instructions comprising a recommendation for further diagnostics and/or treatment based on the health status of the user.

17. The computer-implemented method of claim 15, wherein the simulated actions comprise quarantining and/or treatment.

18. The computer-implemented method of claim 15, further comprising generating, by the one or more computing systems, a simulation of response to one or more simulated actions to be taken by one or more users of a population.

19. The computer-implemented method of claim 1, further comprising displaying, by the user computing device, a map illustrating areas in which a contagious illness is prevalent.

20. The computer-implemented method of claim 1, wherein the user data is input into the user computing device via an application operating on the user computing device.

21. A system to use aggregated health data and outbreak models to provide risk assessments to user computing devices, the system comprising:
   a diagnostic kit, comprising:
   components sufficient to allow a user to be tested to determine if the user has contracted an infectious disease;
   a storage device; and
   a processor communicatively coupled to the storage device, wherein the processor executes application code instructions that are stored in the storage device to cause the system to:
   receive, from a user computing device, a communication comprising user data, the user data comprising a registered contact with a broadcast wireless communication from a second user computing device, the registered contact being based on a length of time of the contact of the user computing device to the proximate second user computing device and a distance between the user computing device and the proximate second user computing device during the contact;
   identify a sub-set of users from a plurality of other users having a connectivity score above a threshold connectivity score and based in part on the registered contact and based on comparing user data with aggregated data from the plurality of other users;
   identify common attributes from the user data from the sub-set of other users;
   determine a population informed risk of infection of the user based at least in part on the connectivity score and common attributes and from a population model of a disease event; and
   communicating, to the user computing device, recommendations for further diagnostics and/or treatment based on the population informed risk of infection of the user and instructions to display the recommendations on a user interface of the user computing device.

22. The system of claim 21, wherein the population model determines a rate of infectivity for COVID-19.

23. The system of claim 21, wherein the population model determines a rate of infectivity for a given geographic region.

24. The system of claim 21, wherein the population model is generated via a machine-learning function.

25. The system of claim 21, wherein the population model is a compartmental model, a Partially Observed Markov Process (POMP)-based model, or a combination thereof.

26. The system of claim 21, wherein the user data comprises user attributes comprising location history, social network connectivity, contact information, dwelling, place of employment, school of enrollment, or a combination thereof.

27. The system of claim 21, wherein user data comprises health data comprising medical history, a genetic profile, a current symptoms profile, diagnostic results, or a combination thereof.

28. The system of claim 21, further comprising simulation of response to one or more simulated actions to be taken by one or more user(s) in a population.

29. The system of claim 21, further comprising communicating instructions to the user computing device, the instructions comprising a recommendation for further diagnostics and/or treatment based on the health status of the user.

30. The method of claim 1, wherein the common attributes are based at least in part on GPS location data history of the user computing device.

\* \* \* \* \*

UNITED STATES PATENT AND TRADEMARK OFFICE
CERTIFICATE OF CORRECTION

PATENT NO. : 11,600,392 B2  
APPLICATION NO. : 17/102901  
DATED : March 7, 2023  
INVENTOR(S) : Sabeti et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 8 days.

Signed and Sealed this  
Seventh Day of January, 2025

Derrick Brent  
*Acting Director of the United States Patent and Trademark Office*

SEQUENCE LISTING

```
<160> NUMBER OF SEQ ID NOS: 4

<210> SEQ ID NO 1
<211> LENGTH: 171
<212> TYPE: DNA
<213> ORGANISM: Mumps Virus

<400> SEQUENCE: 1
ggatcgatgc tacagtgtac taatccaggc ttgggtgatg gtctgtaaat gtatgacagc      60
gtacgaccaa cctgctggat ctgctgatcg gcgatttgcg aaataccagc agcaaggtcg     120
cctggaagca agatacatgc tgcagccaga agcccaaagg ttgattcaaa c              171

<210> SEQ ID NO 2
<211> LENGTH: 20
<212> TYPE: DNA
<213> ORGANISM: Artificial Sequence
<220> FEATURE:
```

```
<223> OTHER INFORMATION: Synthetic

<400> SEQUENCE: 2
gggttcagaa cgtcgtgaga                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
cccgcttaga tgctttcagc                                              20

<210> SEQ ID NO 4
<211> LENGTH: 214
<212> TYPE: DNA
<213> ORGANISM: Streptococcus Sp.

<400> SEQUENCE: 4
agcggcacgc gagctgggtt cagaacgtcg tgagacagtt cggtccctat ccgtcgcggg  60
cgtaggaaat ttgagaggat ctgctcctag tacgagagga ccagagtgga cttaccgctg  120
gtgtaccagt tgtctcgcca gaggcatcgc tgggtagcta tgtagggaag ggataaacgc  180
tgaaagcatc taagtgtgaa acccacctca agat                              214
```